(12) United States Patent
Rao et al.

(10) Patent No.: US 9,512,104 B2
(45) Date of Patent: *Dec. 6, 2016

(54) QUINOLONE INHIBITORS OF LIPOPROTEIN-ASSOCIATED PHOSPHOLIPASE A2

(71) Applicant: Auspex Pharmaceuticals, Inc., La Jolla, CA (US)

(72) Inventors: Tadimeti Rao, San Diego, CA (US); Chengzhi Zhang, San Diego, CA (US)

(73) Assignee: Auspex Pharmaceuticals, Inc., LaJolla, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/043,624

(22) Filed: Oct. 1, 2013

(65) Prior Publication Data

US 2015/0094331 A1    Apr. 2, 2015

Related U.S. Application Data

(63) Continuation of application No. 12/845,384, filed on Jul. 28, 2010, now Pat. No. 8,575,348.

(60) Provisional application No. 61/229,025, filed on Jul. 28, 2009.

(51) Int. Cl.
| | |
|---|---|
| *A61K 31/4375* | (2006.01) |
| *C07D 215/233* | (2006.01) |
| *C07D 401/12* | (2006.01) |

(52) U.S. Cl.
CPC ......... *C07D 401/12* (2013.01); *A61K 31/4375* (2013.01); *C07D 215/233* (2013.01)

(58) Field of Classification Search
CPC .................. C07D 215/233; A61K 31/4375
See application file for complete search history.

(56) References Cited

U.S. PATENT DOCUMENTS

| 6,221,335 | B1 | 4/2001 | Foster | |
|---|---|---|---|---|
| 6,440,710 | B1 | 8/2002 | Keinan et al. | |
| 6,603,008 | B1 | 8/2003 | Ando et al. | |
| 7,517,990 | B2 | 4/2009 | Ito et al. | |
| 8,575,348 | B2 * | 11/2013 | Rao et al. | 546/159 |
| 2002/0013372 | A1 | 1/2002 | Ekins | |
| 2004/0063753 | A1 * | 4/2004 | Hickey et al. | 514/312 |
| 2007/0082929 | A1 | 4/2007 | Gant et al. | |
| 2007/0197695 | A1 | 8/2007 | Potyen et al. | |
| 2008/0033011 | A1 | 2/2008 | Tung | |
| 2008/0287774 | A1 | 11/2008 | Katz-Brull | |
| 2009/0022706 | A1 * | 1/2009 | Gant et al. | 424/94.64 |
| 2010/0069399 | A1 * | 3/2010 | Gant et al. | 514/253.07 |
| 2010/0284970 | A1 * | 11/2010 | Rao et al. | 424/85.7 |
| 2011/0136861 | A1 * | 6/2011 | Rao et al. | 514/312 |
| 2011/0206780 | A1 * | 8/2011 | Gant et al. | 424/715 |
| 2011/0206782 | A1 * | 8/2011 | Zhang | 424/722 |
| 2011/0257260 | A1 * | 10/2011 | Rao et al. | 514/465 |
| 2011/0306552 | A1 * | 12/2011 | Rao et al. | 514/14.9 |
| 2011/0306596 | A1 * | 12/2011 | Rao et al. | 514/212.07 |

FOREIGN PATENT DOCUMENTS

| WO | 9526325 | A2 | 10/1995 |
|---|---|---|---|
| WO | 2002030904 | A1 | 4/2002 |
| WO | 02083144 | A1 | 10/2002 |
| WO | 2006086978 | A2 | 8/2006 |
| WO | 2006086978 | A3 | 8/2006 |
| WO | 2007052274 | A2 | 5/2007 |
| WO | 2007052274 | A3 | 5/2007 |

OTHER PUBLICATIONS

"Measurement of Deuterium Kinetic Isotope Effects in Organic Reactions by Natural-Abundance Deuterium NMR Spectroscopy" by Pascal et al., J. Am. Chem. Soc. 106, 5377-78 (1984).*
"Pharmacological uses and perspectives of heavy water and deuterated compounds," by Kushner et al., Can. J. Physiol. Pharmacol. 77, 79-88 (1999).*
Kushner, D.J. et. al.; Pharmacological uses and perspectives of heavy water and deuterated compounds; Canadian Journal of Physiology and Pharmacology (1999), 77(2), 79-88.
Bauer, LA et. al.; Influence of long-term infusions on lidocaine kinetics; Clin. Pharmacol. Ther. 1982, 433-7.
Borgstrom, L. et. al; Comparative Pharmacokinetics of Unlabeled and Deuterium-Labeled Terbutaline: Demonstration of a Small Isotope Effect; Pharm Sci, 1988, 77(11), 952-4.
Browne, T.R.; Isotope effect: implications for pharmaceutical investigations; Pharmacochemistry Library (1997), 26 (Stable Isotopes in Pharmaceutical Research), 13-18.
Browne, TR et. al.; Pharmacokinetic Equivalence of Stable-Isotope-Labeled and Unlabeled Drugs. Phenobarbital in Man; J Clin Pharmacol, 1982, 22, 309-315.

(Continued)

*Primary Examiner* — Theodore R West
(74) *Attorney, Agent, or Firm* — Baker & Hostetler, LLP

(57) ABSTRACT

The present invention relates to new quinolone inhibitors of lipoprotein-associated phospholipase A2 activity, pharmaceutical compositions thereof, and methods of use thereof.

16 Claims, No Drawings

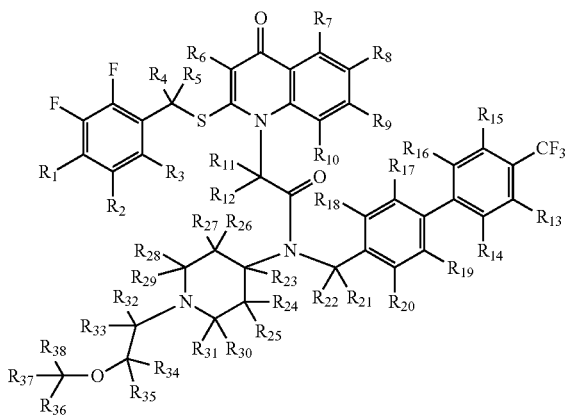

Formula I

(56) References Cited

OTHER PUBLICATIONS

Burm, AGL et. al.; Pharmacokinetics of Lidocaine and bupivacaine and stable isotope-labeled analogs: a study in healthy volunteers; Biopharmaceutics and Drug Disposition, 1988, 9, 85-95.
Elison, C.; Effect of deuteration of N—CH3 group on potency and enzymatic N-demethylation of morphine; Science, 1961, 134(3485), 1078-9.
Farmer, PB et. al.; Synthesis, Metabolism, and Antitumor Activity of Deuterated Analogues of 1-(2-Choloroethyl)-3-cyclohexyl-1-nitrosourea; Journal of Medicinal Chemistry, 1978, vol. 21, No. 6, 514-20.
Fisher, MB et. al.; The complexities inherent in attempts to decrease drug clearance by blocking sites of CYP-mediated metabolism; Curr Opin Drug Discov Develop; 2006, 9(1), 101-9.
Foster, A.B.; Deuterium isotope effects in studies of drug metabolism; Trends in Pharmacological Sciences (1984), 5 (12), 524-7.
Helfenbein, J. et. al.; Isotopic Effect Study of Propofol Deuteration on the Metabolism, Activity, and Toxicity of the Anesthetic; J. Med. Chem. 2002, 45, 5806-5808.
Lee, H. et. al.; Deuterium Magic Angle Spinning Studies of Substrates Bound to Cytochrome P450; Biochemistry 1999, 38, 10808-10813.
Mamada, K. et. al.; Pharmacokinetic Equivalence of Deuterium-Labeled and Unlabeled Phenytoin; Drug Metabolism and Disposition, 1986, 14(4), 509-11.
Nelson, SD et. al.; The Use of Deuterium Isotope Effect to Probe the Active Site Properties, Mechanism of Cytochrome P450-catalyzed Reactions, and Mechanisms of Metabolically Dependent Toxicity; Drug Metabolism and Disposition 31:1481-1498, 2003.
Nelson, SD et. al.; Primary and B-Secondary Deuterium Isotope Effects in N-Deethylation Reactions; Journal of Medicinal Chemistry, 1975, vol. 18, No. 11.
Pohl, L.R. et. al.; Determination of toxic pathways of metabolism by deuterium substitution; Drug Metabolism Reviews (1985), vol. Date 1984, 15(7), 1335-51.
Rampe, D. et. al.; Deuterated Analogs of verapamil and nifedipine. Synthesis and biological activity; Eur J Med Chem (1993) 28,259-263.
Baillie, Thomas, The Use of Stable Isotopes in Pharmaceutical Research, Pharmacological Reviews, 1981, 33(2), 81-132.
Browne, Thomas, Stable Isotope Techniques in Early Drug Development: An Economic Evaluation, J. Clin. Pharmacol., 1998, 38, 213-220.
Cherrah et al. Study of Deuterium Isotope Effects on Protein Binding by Gas Chromatography/Mass Spectrometry. Caffeine and Deuterated Isomers, Biomedical and Environmental Mass Spectrometry, 1987, 14, 653-657.
Dyck et al.,Effects of Deuterium Substitution on the Catabolism of Beta-Phenethylamine: An In Vivo Study, J. Neurochem., 1986, 46(2), 399-404.
Gouyette, Alain, Use of Deuterium-Labelled Elliptinium and Its Use in Metabolic Studies, Biomedical and Environmental Mass Spectrometry, 1988, 15, 243-247.
Haskins, NJ., The Application of Stable Isotopes in Biomedical Research, Biomedical Mass Spectrometry, 1982, 9(7), 269-277.
Honma et al., The Metabolism of Roxatidine Acetate Hydrochloride, Drug Metabolism and Disposition, 1987, 15(4), 551-559.
Pieiaszek et al., Moricizine Bioavailability Via Simultaneous, Dual, Stable Isotope Administration: Bioequivalence Implications, J. Clin. Pharmacol., 1999, 39, 817-825.
Tonn et al., Simultaneous Analysis of Diphenylhydramine and a Stable Isotope Analog (2H10) Diphenylhydramine Using Capillary Gas Chromatography With Mass Selective Detection in Biological Fluids From Chronically Instrumented Pregnant Ewes, Biomedical Mass Spectrometry, 1993, 22, 633-642.
Wolen et al., The Application of Stable Isotopes to Studies of Drug Bioavailibility and Bioequivalence, J. Clin. Pharmacol., 1986, 26, 419-424.
Foster AB, Deuterium Isotope Effects in the Metabolism of Drugs and Xenobiotics: Implications for Drug Design, Adv. Drug Res., Academic Press, London, GB, vol. 14, Jan. 1, 1985, pp. 1-40.
Rao et al., Pyrimidone Inhibitors of Lipoprotein-Associated Phospholipase A2, Auspex Pharmaceuticals, Inc., U.S. Appl. No. 12/840,725—Prosecution History, Downloaded Jun. 11, 2013.
Dekker N et al., Two-dimensional 1H-NMR studies of phospholipase-A2-inhibitor complexes bound to a micellar lipid-water interface, European Journal of Biochemistry, Aug. 1, 1991;199(3):601-607.

* cited by examiner

QUINOLONE INHIBITORS OF LIPOPROTEIN-ASSOCIATED PHOSPHOLIPASE A2

This application is a continuation of U.S. patent application Ser. No. 12/845,384, filed Jul. 28, 2010, which claims the benefit of priority of U.S. provisional application No. 61/229,025, filed Jul. 28, 2009, the disclosure of which is hereby incorporated by reference as if written herein in its entirety.

Disclosed herein are new substituted quinolone compounds, pharmaceutical compositions made thereof, and methods to inhibit lipoprotein-associated phospholipase A2 activity in a subject are also provided for, for the treatment of disorders such as coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, and asthma.

Rilapladib (SB-659032; CAS #412950-08-4), (2-[2-(2,3-difluorobenzylsulfanyl)-4-oxo-1,4-dihydroquinolin-1-yl]-N-[1-(2-methoxyethyl)piperidin-4-yl]-N-[4'-(trifluoromethyl)biphenyl-4-ylmethyl]acetamide), is a lipoprotein-associated phospholipase A2 inhibitor. Rilapladib is currently under investigation for the treatment of coronary disorders, atherosclerosis, and asthma (WO 2002030904).

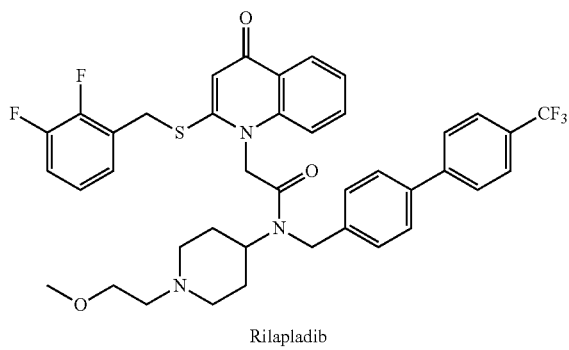 [SMILES: COCCN1CCC(N(Cc2ccc(-c3ccc(C(F)(F)F)cc3)cc2)C(=O)Cn2c(SCc3cccc(F)c3F)cc(=O)c3ccccc32)CC1]

Rilapladib

Deuterium Kinetic Isotope Effect

In order to eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-E_{act}/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1H$), a C-D bond is stronger than the corresponding C—$^1H$ bond. If a C—$^1H$ bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C—$^1H$ bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects.

Deuterium ($^2H$ or D) is a stable and non-radioactive isotope of hydrogen that has approximately twice the mass of protium ($^1H$), the most common isotope of hydrogen. Deuterium oxide ($D_2O$ or "heavy water") looks and tastes like $H_2O$, but exhibits different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Rilapladib is a lipoprotein-associated phospholipase A2 inhibitor. The carbon-hydrogen bonds of rilapladib contain a naturally occurring distribution of hydrogen isotopes, namely $^1$H or protium (about 99.9844%), $^2$H or deuterium (about 0.0156%), and $^3$H or tritium (in the range between about 0.5 and 67 tritium atoms per $10^{18}$ protium atoms). Increased levels of deuterium incorporation may produce a detectable Deuterium Kinetic Isotope Effect (DKIE) that could effect the pharmacokinetic, pharmacologic and/or toxicologic profiles of rilapladib in comparison with rilapladib having naturally occurring levels of deuterium.

Based on discoveries made in our laboratory, as well as considering the literature; rilapladib is likely to be metabolized in humans at the O-methyl group, the methoxyethyl methylene groups, the N-methylene groups, the piperidine ring, and the S-methylene group. The current approach has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the strong potential to slow the metabolism of rilapladib and attenuate interpatient variability.

Novel compounds and pharmaceutical compositions, certain of which have been found to inhibit lipoprotein-associated phospholipase A2 activity have been discovered, together with methods of synthesizing and using the compounds, including methods for the treatment of lipoprotein-associated phospholipase A2-mediated disorders by administering the compounds as disclosed herein.

In certain embodiments of the present invention, compounds have structural Formula I:

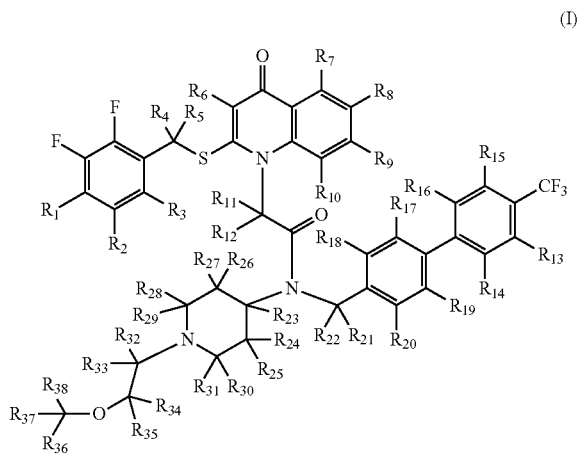

(I)

or a pharmaceutically acceptable salt thereof, wherein:
$R_1$-$R_{38}$ are independently selected from the group consisting of hydrogen and deuterium; and
at least one of $R_1$-$R_{38}$ is deuterium.

Certain compounds disclosed herein may possess useful lipoprotein-associated phospholipase A2 inhibiting activity, and may be used in the treatment or prophylaxis of a disorder in which lipoprotein-associated phospholipase A2 plays an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for inhibiting lipoprotein-associated phospholipase A2 activity. Other embodiments provide methods for treating a lipoprotein-associated phospholipase A2-mediated disorder, comprising administering to said patient a therapeutically effective amount of a compound or composition according to the present invention. Also provided is the use of certain compounds disclosed herein for use in the manufacture of a medicament for the prevention or treatment of a disorder ameliorated by inhibiting lipoprotein-associated phospholipase A2 activity.

The compounds as disclosed herein may also contain less prevalent isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen.

In certain embodiments, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a", "an", and "the" may refer to plural articles unless specifically stated otherwise.

The term "about", as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ ... to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium", when used to describe a given position in a molecule such as $R_1$-$R_{38}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S", depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The terms "treat", "treating", and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent", "preventing", and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "lipoprotein-associated phospholipase A2" refers to a member of the phospholipase A2 enzyme family, and is primarily found in blood and atherosclerotic plaque. Lipoprotein-associated phospholipase A2 is a potent pro-inflammatory mediator involved in the vascular inflammation process. It has been suggested that elevated lipoprotein-associated phospholipase A2 activity is partly responsible for the development and progression of atherosclerosis and cardiovascular disorders. Thus, inhibition of lipoprotein-associated phospholipase A2 activity is expected to be useful in the treatment of these disorders. Mechanistically, lipoprotein-associated phospholipase A2 preferentially cleaves LDL cholesterol to form lysophosphatidyl choline and oxidized fatty acids. These molecules lead to several atherogenic actions, including the expression of adhesion molecules and the attraction of macrophages and lymphocytes to the atherosclerotic lesion. These events lead to the build up of plaque within the arterial wall. The rupture of this unstable atherosclerotic plaque, is the primary cause of most heart attacks and strokes. Thus, it is hypothesized that inhibiting lipoprotein-associated phospholipase A2 activity will prevent and/or reverse the build up of these macrophage enriched lesions.

The term "lipoprotein-associated phospholipase A2-mediated disorder", refers to a disorder that is characterized by abnormal lipoprotein-associated phospholipase A2 activity, or normal lipoprotein-associated phospholipase A2 activity that when modulated ameliorates other abnormal biochemical processes. A lipoprotein-associated phospholipase A2-mediated disorder may be completely or partially mediated by modulating lipoprotein-associated phospholipase A2 activity. In particular, a lipoprotein-associated phospholipase A2-mediated disorder is one in which inhibition of lipoprotein-associated phospholipase A2 activity results in some effect on the underlying disorder e.g., administration of a lipoprotein-associated phospholipase A2 inhibitor results in some improvement in at least some of the patients being treated.

The term "lipoprotein-associated phospholipase A2 inhibitor", refers to the ability of a compound disclosed herein to alter the function of lipoprotein-associated phospholipase A2. A lipoprotein-associated phospholipase A2 inhibitor may block or reduce the activity of lipoprotein-associated phospholipase A2 by forming a reversible or irreversible covalent bond between the inhibitor and lipoprotein-associated phospholipase A2 or through formation of a noncovalently bound complex. Such inhibition may be manifest only in particular cell types or may be contingent on a particular biological event. The term "lipoprotein-associated phospholipase A2 inhibitor" also refers to altering the function of lipoprotein-associated phospholipase A2 by decreasing the probability that a complex forms between lipoprotein-associated phospholipase A2 and a natural substrate. In some embodiments, inhibiting lipoprotein-associated phospholipase A2 activity may be assessed using the methods described in WO 2002030904; Mohler et al., *J. Am. Coll. Cardiol* 2008, 51(17), 1632-41; and Wilensky et al., *Nature Medicine* 2008, 14(10), 1059-66.

The term "lipoprotein-associated phospholipase A2 inhibiting activity" or "inhibition of lipoprotein-associated phospholipase A2 activity" refers to altering the function of lipoprotein-associated phospholipase A2 by administering a lipoprotein-associated phospholipase A2 inhibitor.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The term "pharmaceutically acceptable carrier", "pharmaceutically acceptable excipient", "physiologically acceptable carrier", or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The terms "active ingredient", "active compound", and "active substance" refer to a compound, which is administered, alone or in combination with one or more pharmaceutically acceptable excipients or carriers, to a subject for treating, preventing, or ameliorating one or more symptoms of a disorder.

The terms "drug", "therapeutic agent", and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.*

1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The compounds disclosed herein can exist as therapeutically acceptable salts. The term "pharmaceutically acceptable salt", as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use," Stah and Wermuth, Ed., (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy,* supra; *Modified-Release Drug Deliver Technology*, Rathbone et al., Eds., Drugs and the Pharmaceutical Science, Marcel Dekker, Inc.: New York, N.Y. 2002; Vol. 126).

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a lipoprotein-associated phospholipase A2-mediated disorder comprising administering to a subject having or suspected of having such a disorder, a therapeutically effective amount of a compound as disclosed herein or a pharmaceutically acceptable salt, solvate, or prodrug thereof.

Lipoprotein-associated phospholipase A2-mediated disorders, include, but are not limited to, coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, asthma, and/or any disorder which can lessened, alleviated, or prevented by administering a lipoprotein-associated phospholipase A2 inhibitor.

In certain embodiments, a method of treating a lipoprotein-associated phospholipase A2-mediated disorder comprises administering to the subject a therapeutically effective amount of a compound as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome $P_{450}$ or monoamine oxidase isoform in the subject; (4) decreased metabolism via at least one polymorphically-expressed cytochrome $P_{450}$ isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described by Li et al. *Rapid Communications in Mass Spectrometry* 2005, 19, 1943-1950, and any references cited therein and any modifications thereof.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al., *British Journal of Clinical Pharmacology* 2000, 49, 343-351. The inhibition of the $MAO_A$ isoform is measured by the method of Weyler et al., *J. Biol Chem.* 1985, 260, 13199-13207. The inhibition of the $MAO_B$ isoform is measured by the method of Uebelhack et al., *Pharmacopsychiatry* 1998, 31, 187-192.

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to, reduced heart attacks and/or strokes, reduced coronary lesion development, and stabilization of atherosclerotic plaque.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of lipoprotein-associated phospholipase A2-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more medications in the treatment of coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, and asthma.

In certain embodiments, the compounds disclosed herein can be combined with one or more alpha adrenergic receptor antagonists, Angiotensin II receptor antagonists, angiotensin-converting enzyme inhibitors, anti-arrhythmics, anti-thrombotic agents, anti-platelet agents, beta adrenergic receptor antagonists, calcium channel blockers, fibrates, and HMG-CoA reductase inhibitors.

In certain embodiments, the compounds disclosed herein can be combined with one or more alpha adrenergic receptor antagonists known in the art, including, but not limited to, abanoquil, adimolol, ajmalicine, alfuzosin, amosulalol, arotinolol, atiprosin, benoxathian, buflomedil, bunazosin, carvedilol, CI-926, corynanthine, dapiprazole, DL-017, domesticine, doxazosin, eugenodilol, fenspiride, GYKI-12,743, GYKI-16,084, indoramin, ketanserin, L-765,314, labetalol, mephendioxan, metazosin, monatepil, moxisylyte (thymoxamine), naftopidil, nantenine, neldazosin, nicergoline, niguldipine, pelanserin, phendioxan, phenoxybenzamine, phentolamine, piperoxan, prazosin, quinazosin, ritanserin, RS-97,078, SGB-1,534, silodosin, SL-89.0591, spiperone, talipexole, tamsulosin, terazosin, tibalosin, tiodazosin, tipentosin, tolazoline, trimazosin, upidosin, urapidil, zolertine, 1-PP, adimolol, atipamezole, BRL-44408, buflomedil, cirazoline, efaroxan, esmirtazapine, fluparoxan, GYKI-12,743, GYKI-16,084, idazoxan, mianserin, mirtazapine, MK-912, NAN-190, olanzapine, phentolamine, phenoxybenzamine, piperoxan, piribedil, rauwolscine, rotigotine, SB-269,970, setiptiline, spiroxatrine, sunepitron, tolazoline, and yohimbine.

In certain embodiments, the compounds disclosed herein can be combined with one or more Angiotensin II receptor antagonists (AIIRA), including, but not limited to, candesartan, eprosartan, irbesartan, losartan, olmesartan, tasosartan, telmisartan, and valsartan.

In certain embodiments, the compounds disclosed herein can be combined with one or more angiotensin-converting enzyme inhibitors (ACE inhibitors), including, but not limited to, captopril, enalapril, lisinopril, perindopril, ramipril, quinapril, benazepril, cilazapril, fosinopril, trandolapril, spirapril, delapril, moexipril, temocapril, zofenopril, and imidapril.

In certain embodiments, the compounds disclosed herein can be combined with one or more anti-arrhythmics, including, but not limited to, quinidine, procainamide, disopyramide, sparteine, ajmaline, prajmaline, lorajmine, lidocaine, mexiletine, tocainide, aprindine, propafenone, flecainide, lorcainide, encainide, amiodarone, bretylium tosilate, bunaftine, dofetilide, ibutilidem, tedisamil, moracizine, and cibenzoline.

In certain embodiments, the compounds provided herein can be combined with one or more antithrombtics, including, but not limited to, dicoumarol, phenindione, warfarin, phenprocoumon, acenocoumarol, ethyl biscoumacetate, clorindione, diphenadione, tioclomarol, heparin, antithrombin III, dalteparin, enoxaparin, nadroparin, parnaparin, reviparin, danaparoid, tinzaparin, sulodexide, bemiparin, ditazole, cloricromen, picotamide, clopidogrel, ticlopidine, acetylsalicylic acid, dipyridamole, carbasalate calcium, epoprostenol, indobufen, iloprost, abciximab, aloxiprin, eptifibatide, tirofiban, triflusal, beraprost, treprostinil, prasugrel, streptokinase, alteplase, urokinase, fibrinolysin, brinase, reteplase, saruplase, ancrod, drotrecogin alfa (activated), tenecteplase, protein C, desirudin, lepirudin, argatroban, melagatran, ximelagatran, bivalirudin, dabigatran etexilate, defibrotide, dermatan sulfate, fondaparinux, and rivaroxaban.

In certain embodiments, the compounds provided herein can be combined with one or more antiplatelet agents, including, but not limited to, abciximab, eptifibatide, tirofiban, clopidogrel, prasugrel, ticlopidine, ticagrelor, beraprost, prostacyclin, iloprost, treprostinil, acetylsalicylic acid, aloxiprin, carbasalate calcium, indobufen, dipyridamole, picotamide, terutroban, cilostazol, dipyridamole, triflusal, cloricromen, and ditazole.

In certain embodiments, the compounds disclosed herein can be combined with one or more beta-adrenergic antagonists, including, but not limited to, acebutolol, adaprolol, adimolol, afurolol, alprenolol, alprenoxime, amosulalol, ancarolol, arnolol, arotinolol, atenolol, befunolol, betaxolol, bevantolol, bisoprolol, bopindolol, bormetolol, bornaprolol, brefonalol, bucindolol, bucumolol, bufetolol, buftiralol, bufuralol, bunitrolol, bunolol, bupranolol, burocrolol, butaxamine, butidrine, butofilolol, capsinolol, carazolol, carpindolol, carteolol, carvedilol, celiprolol, cetamolol, cicloprolol, cinamolol, cloranolol, cyanopindolol, dalbraminol, dexpropranolol, diacetolol, dichloroisoprenaline, dihydroalprenolol, dilevalol, diprafenone, draquinolol, dropranolol, ecastolol, epanolol, ericolol, ersentilide, esatenolol, esmolol, esprolol, eugenodilol, exaprolol, falintolol, flestolol, flusoxolol, hydroxycarteolol, hydroxytertatolol, ICI-118,551, idropranolol, indenolol, indopanolol, iodocyanopindolol, iprocrolol, isoxaprolol, isamoltane, labetalol, landiolol, levobetaxolol, levobunolol, levocicloprolol, levomoprolol, medroxalol, mepindolol, metalol, metipranolol, metoprolol, moprolol, nadolol, nadoxolol, nafetolol, nebivolol, neraminol, nifenalol, nipradilol, oberadilol, oxprenolol, pacrinolol, pafenolol, pamatolol, pargolol, parodilol, penbutolol, penirolol, PhQA-33, pindolol, pirepolol, practolol, primidolol, procinolol, pronethalol, propafenone, propranolol, ridazolol, ronactolol, soquinolol, sotalol, spirendolol, SR 59230A, sulfinalol, TA-2005, talinolol, tazolol, teoprolol, tertatolol, terthianolol, tienoxolol, tilisolol, timolol, tiprenolol, tolamolol, toliprolol, tribendilol, trigevolol, xibenolol, and xipranolol.

In certain embodiments, the compounds disclosed herein can be combined with one or more calcium channel blockers, including, but not limited to amlodipine, felodipine, isradipine, nicardipine, nifedipine, nimodipine, nisoldipine, nitrendipine, lacidipine, nilvadipine, manidipine, barnidipine, lercanidipine, cilnidipine, benidipine, mibefradil, verapamil, gallopamil, diltiazem, fendiline, bepridil, lidoflazine, and perhexiline.

In certain embodiments, the compounds provided herein can be combined with one or more fibrates, including, but not limited to, clofibrate, bezafibrate, aluminium clofibrate, gemfibrozil, fenofibrate, simfibrate, ronifibrate, ciprofibrate, etofibrate, and clofibride.

In certain embodiments, the compounds disclosed herein can be combined with one or more HMG-CoA reductase inhibitors (statins), including, but not limited to, atorvastatin, cerivastatin, fluvastatin, lovastatin, mevastatin, pitavastatin, pravastatin, rosuvastatin, and simvastatin.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; squalene synthetase inhibitors; bile acid sequestrants, such as questran; niacin; anti-atherosclerotic agents, such as ACAT inhibitors; MTP Inhibitors; potassium channel activators; alpha-muscarinic agents; beta-muscarinic agents, such as carvedilol and metoprolol; diuretics, such as chlorothlazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as vinca alkaloids, epipodophyllotoxins, and taxanes; topoisomerase inhibitors; prenyl-protein transferase inhibitors; cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating lipoprotein-associated phospholipase A2-mediated disorders in a human or animal subject in need of such treatment comprising administering to said subject an amount of a compound disclosed herein effective to reduce or prevent said disorder in the subject, in combination with at least one additional agent for the treatment of said disorder. In a related aspect, certain embodiments provide therapeutic compositions comprising at least one compound disclosed herein in combination with one or more additional agents for the treatment of lipoprotein-associated phospholipase A2-mediated disorders.

General Synthetic Methods for Preparing Compounds

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described herein and routine modifications thereof, and/or procedures found in WO 2002030904, which are hereby incorporated in their entirety, and references cited therein and routine modifications thereof. Compounds as disclosed herein can also be prepared as shown in any of the following schemes and routine modifications thereof.

The following schemes can be used to practice the present invention. Any position shown as hydrogen may optionally be replaced with deuterium.

Scheme I

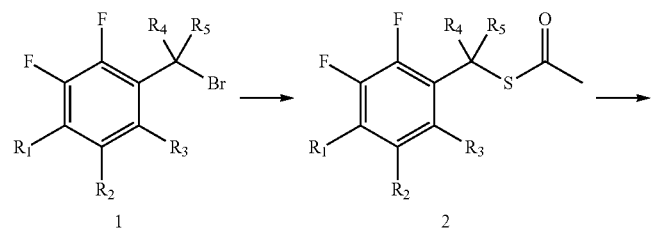

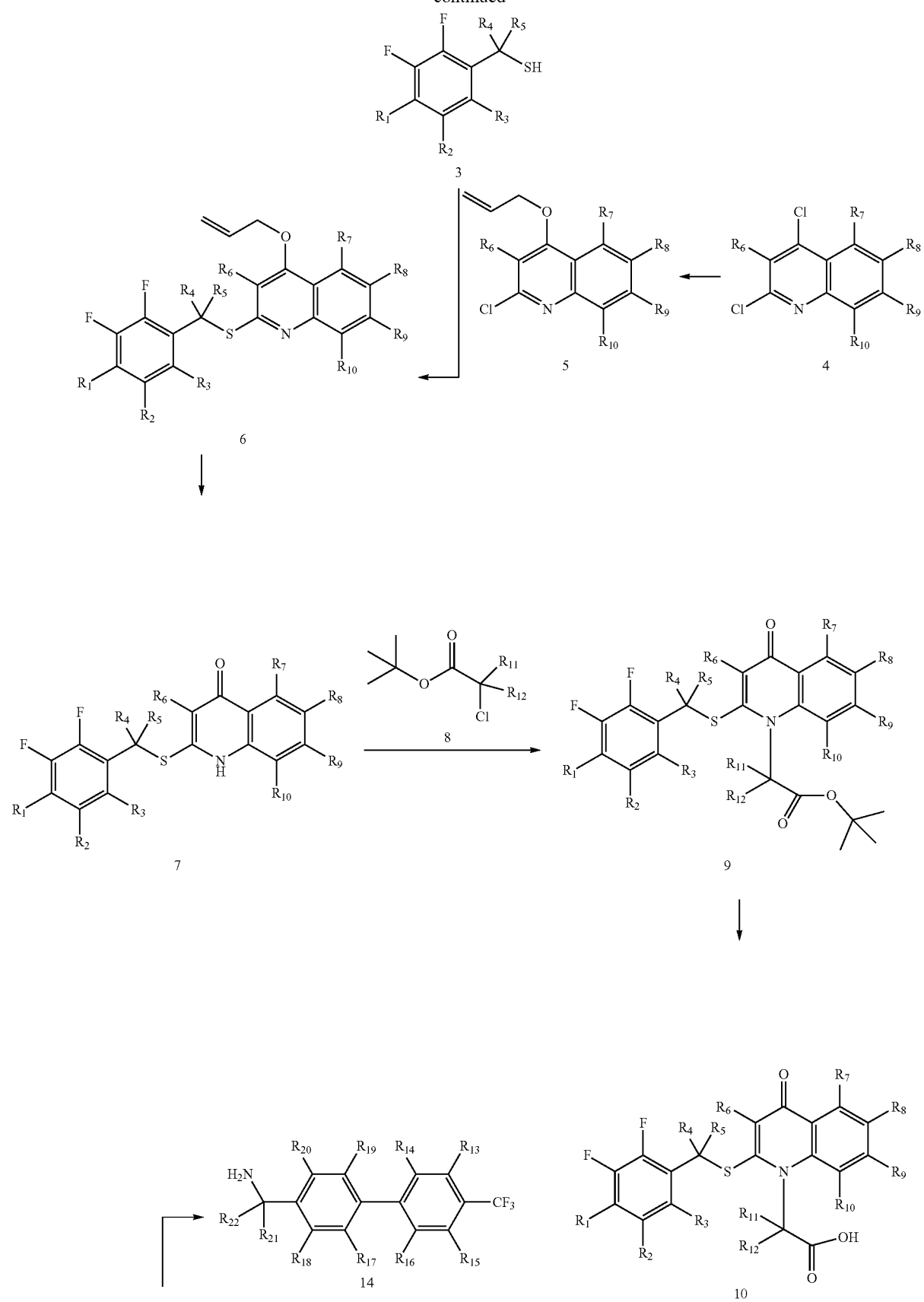

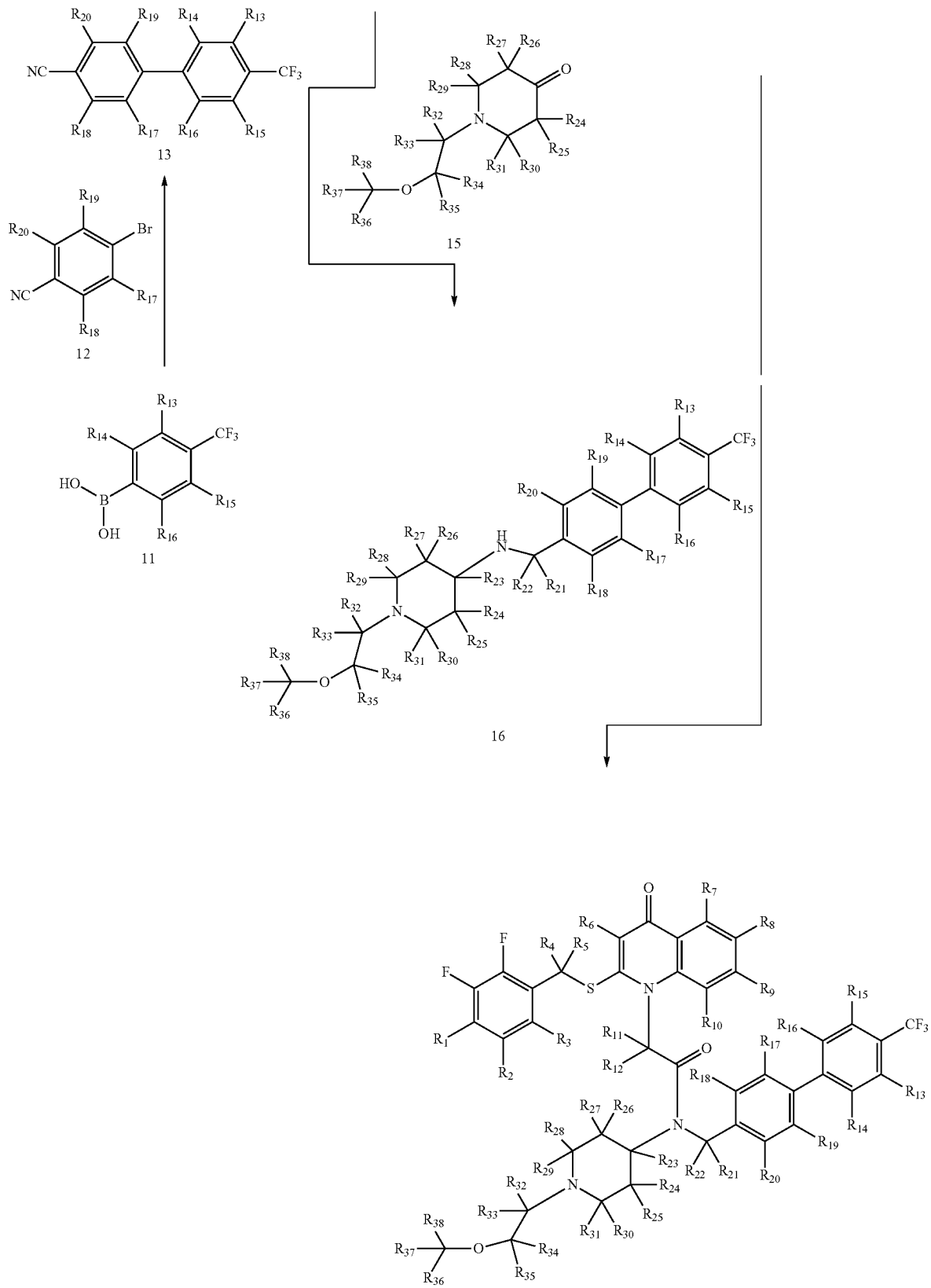

Compound 1 is reacted with an appropriate thioacetate, such as potassium thioacetate, in an appropriate solvent, such as N,N-dimethylformamide, to give compound 2. Compound 2 is hydrolyzed in the presence of an appropriate base, such as potassium carbonate, in an appropriate solvent, such as an appropriate mixture of methanol and water, to give compound 3. Compound 4 is reacted with allyl alcohol, in the presence of an appropriate base, such as sodium hydride, in an appropriate solvent, such as N,N-dimethylformamide, to give compound 5. Compound 5 is reacted with compound 3 in the presence of an appropriate base, such as sodium hydride, in an appropriate solvent, such as N,N-dimethylformamide, to give compound 6. Compound 6 is treated with an appropriate base, such as 1,4-diazobicyclo[2,2,2]octane, in the presence of an appropriate catalyst, such as triphenylphosphine rhodium(I) chloride, in an appropriate solvent, such as an appropriate mixture of water and ethanol, to give compound 7. Compound 7 is reacted with compound 8 in the presence of an appropriate base, such as n-butyllithium, in an appropriate solvent, such as tetrahydrofuran, to give compound 9. Compound 9 is treated with an appropriate acid, such as trifluoroacetic acid, in an appropriate solvent, such as dichloromethane, to give compound 10. Compound 11 is reacted with compound 12 in the presence of an appropriate catalyst, such as palladium acetate, in the presence of an appropriate base, such as sodium carbonate, in an appropriate solvent, such as 1,2-dimethoxyethane, to give compound 13. Compound 13 is treated with an appropriate reducing reagent, such as lithium aluminum hydride, in an appropriate solvent, such as anhydrous tetrahydrofuran, to give compound 14. Compound 14 is reacted with compound 15 in the presence of an appropriate acid, such as acetic acid, in the presence of an appropriate reducing reagent, such as sodium triacetoxyborohydride, in an appropriate solvent, such as dichloroethane, to give compound 16. Compound 16 is reacted with compound 10 in the presence of an appropriate base, such as N,N-diisopropylethylamine, in the presence of an appropriate coupling reagent, such as 0-(7-azabenzotriazol-1-yl)-N,N,N',N'-tetra-methyluronium hexafluorophosphate, in an appropriate solvent, such as N,N-dimethylformamide, to give compound 17 of Formula I.

Deuterium can be incorporated to different positions synthetically, according to the synthetic procedure as shown in Scheme I, by using appropriate deuterated intermediates. For example, to introduce deuterium at one or more positions of $R_1$-$R_5$, compound 1 with the corresponding deuterium substitutions can be used. To introduce deuterium at one or more positions of $R_6$-$R_{10}$, compound 4 with the corresponding deuterium substitutions can be used. To introduce deuterium at one or more positions of $R_{11}$-$R_{12}$, compound 8 with the corresponding deuterium substitutions can be used. To introduce deuterium at one or more positions of $R_{13}$-$R_{16}$, compound 11 with the corresponding deuterium substitutions can be used. To introduce deuterium at one or more positions of $R_{17}$-$R_{20}$, compound 12 with the corresponding deuterium substitutions can be used. To introduce deuterium at one or more positions of $R_{21}$-$R_{22}$, lithium aluminum deuteride can be used. To introduce deuterium at one or more positions of $R_{24}$-$R_{38}$, compound 15 with the corresponding deuterium substitutions can be used. To introduce deuterium at $R_{23}$, sodium triacetoxyborodeuteride can be used.

The following compounds can generally be made using the methods described above.

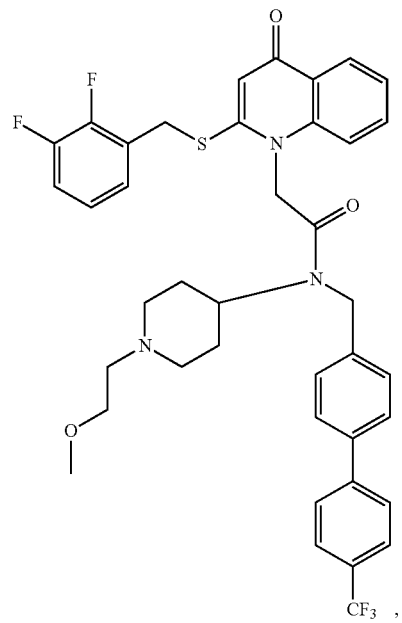

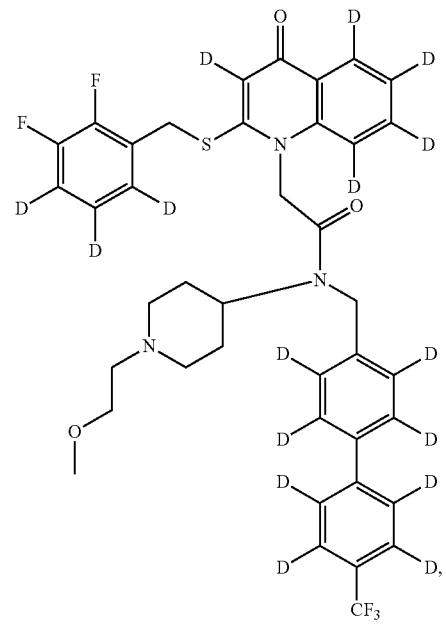

25
-continued
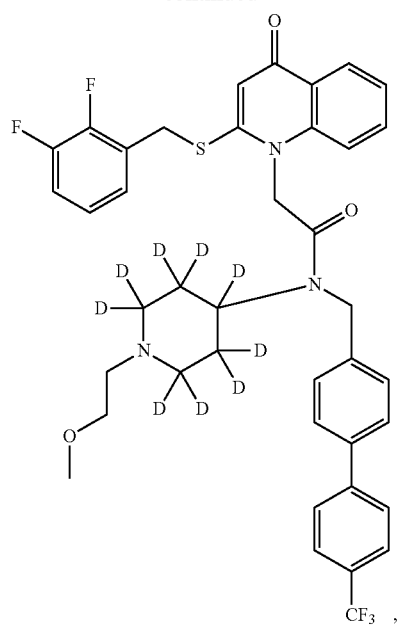
26
-continued
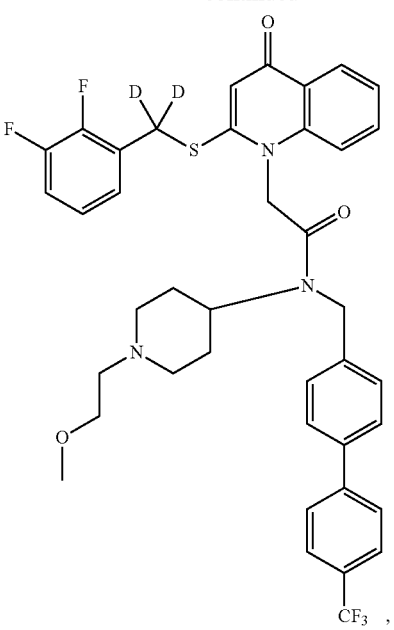
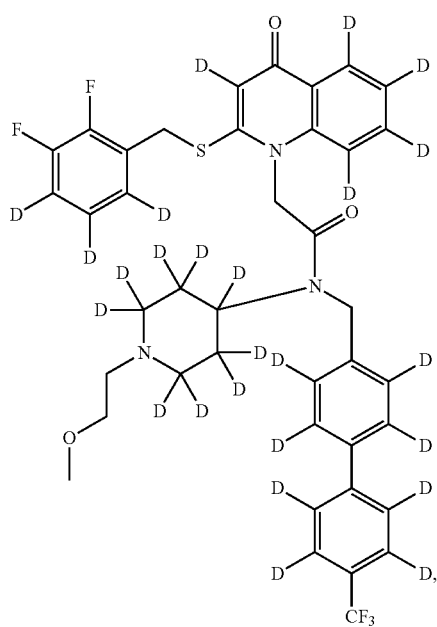
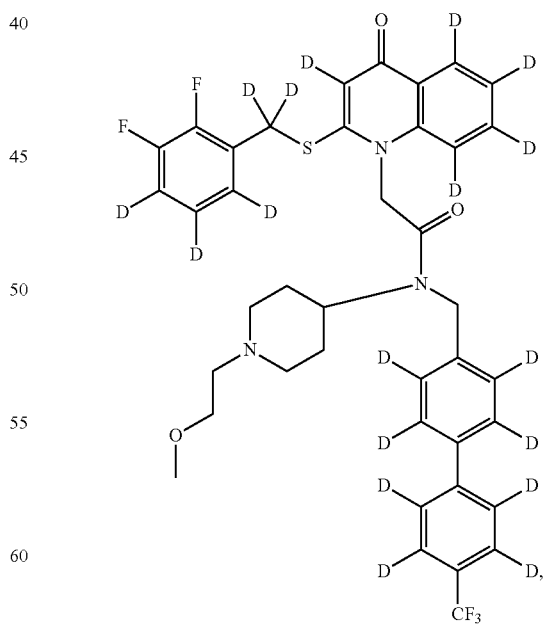

27
-continued
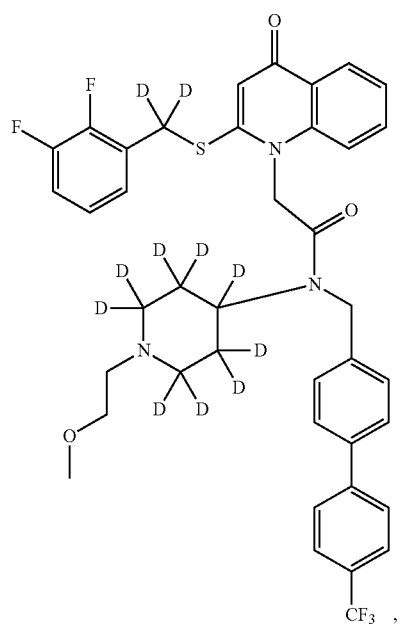
28
-continued
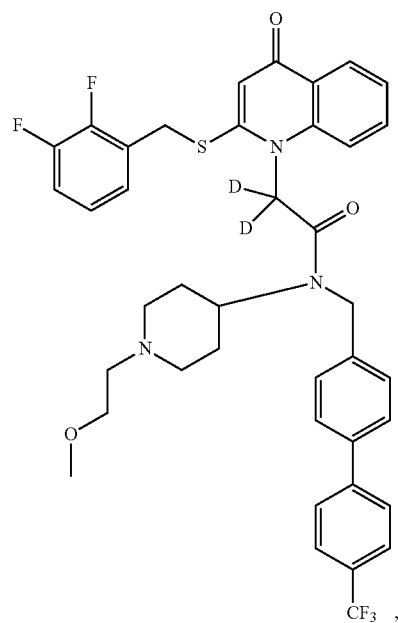
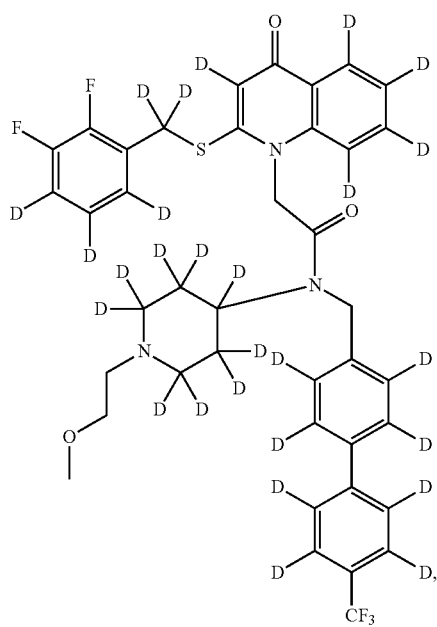
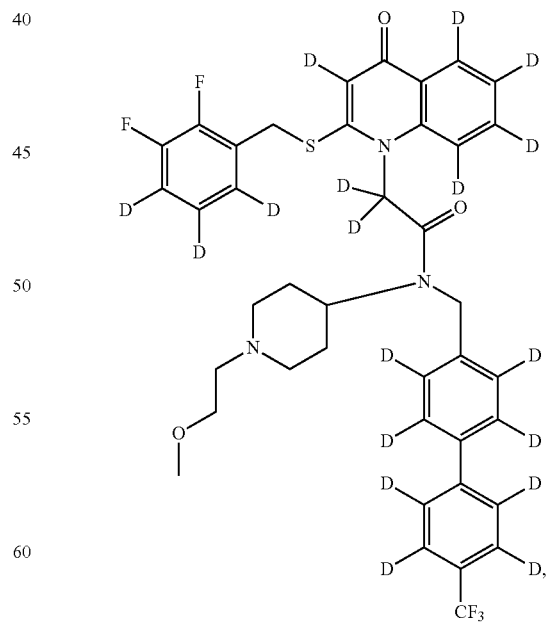

29
-continued
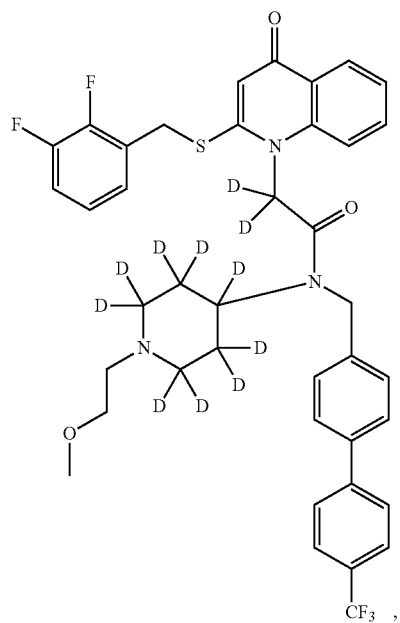
30
-continued
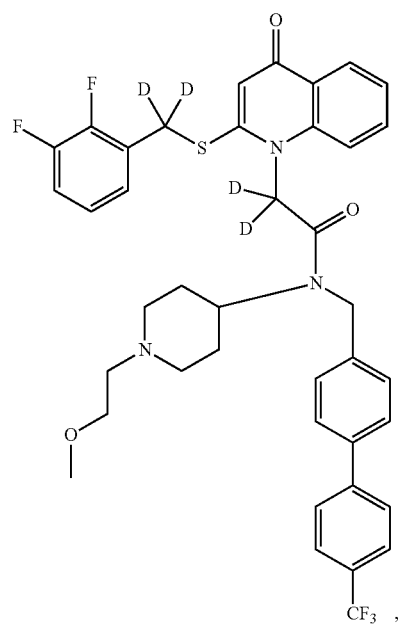
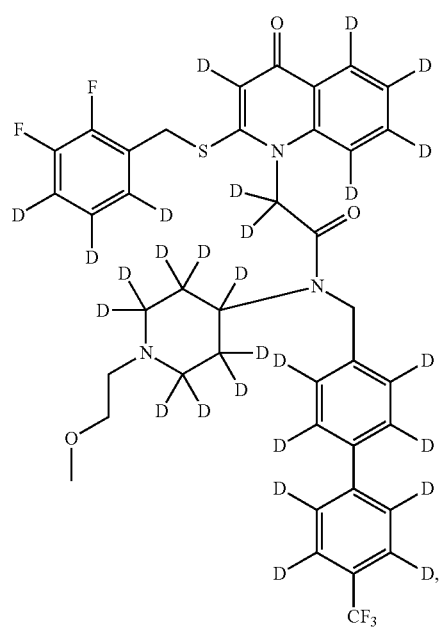
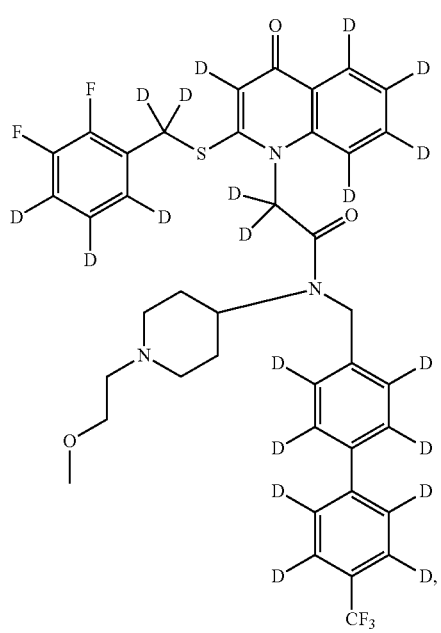

31
-continued
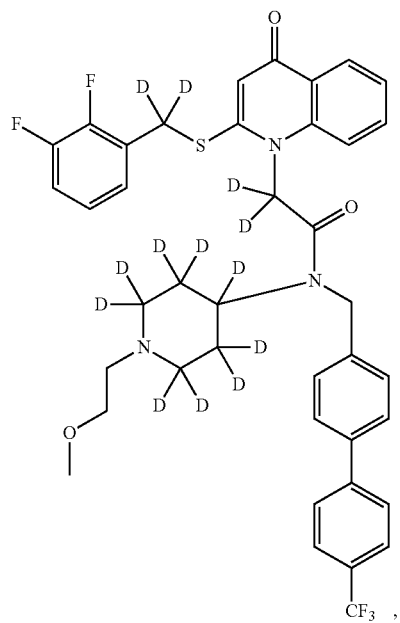
32
-continued
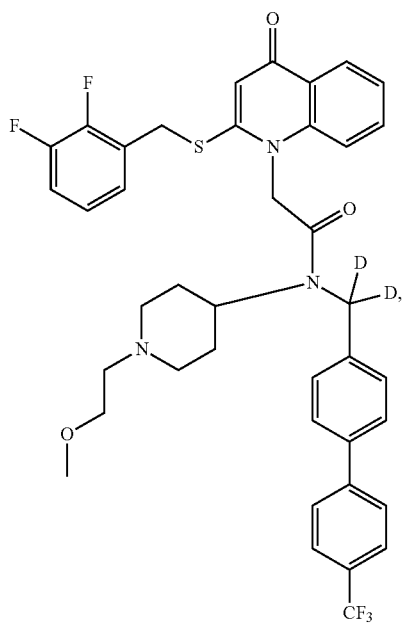
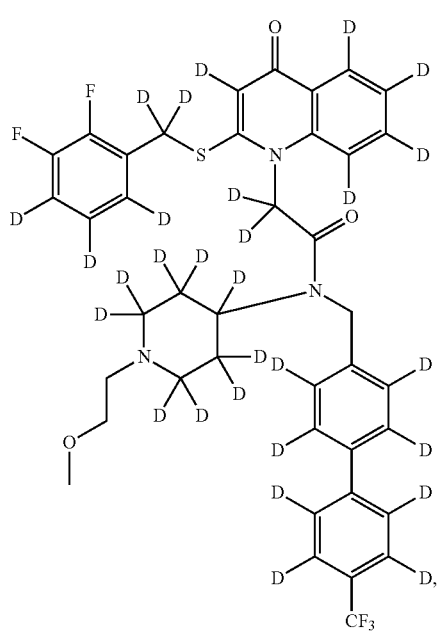
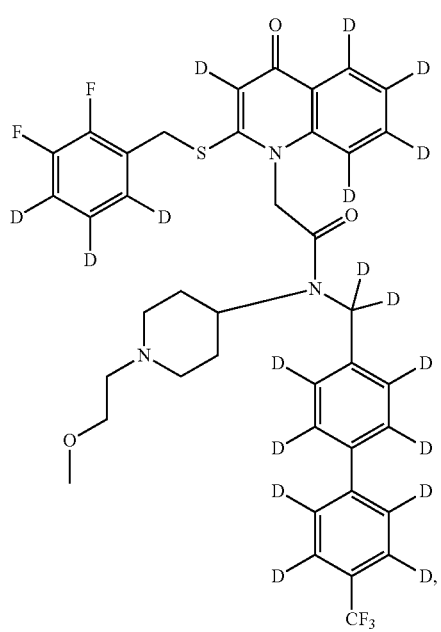

33
-continued
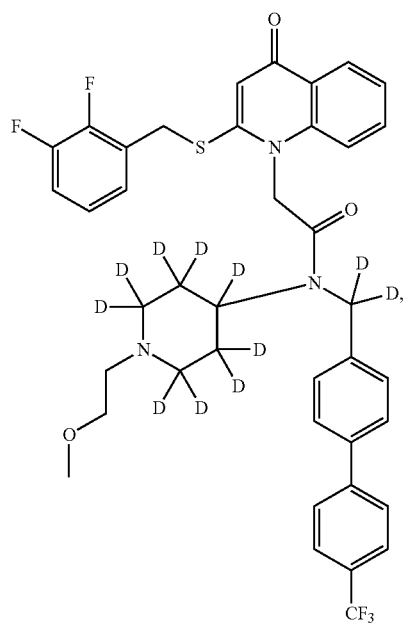
34
-continued
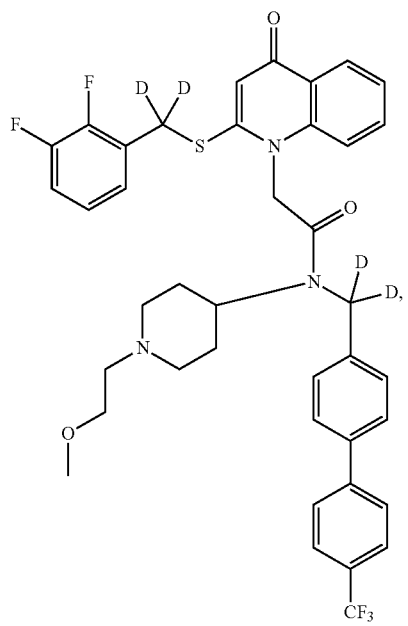
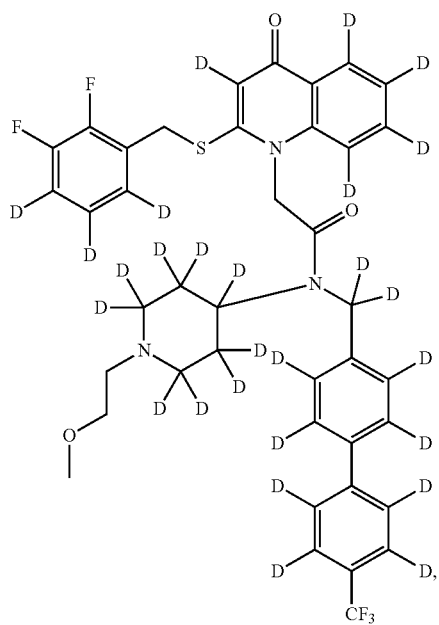
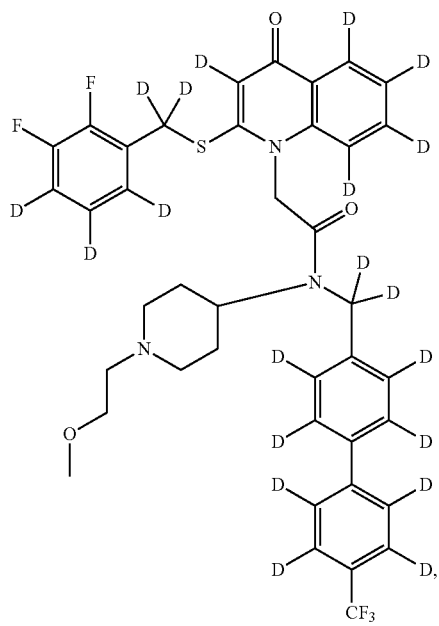

35
-continued
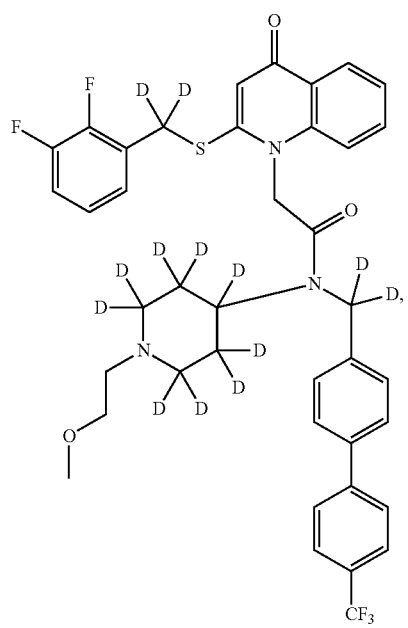
36
-continued
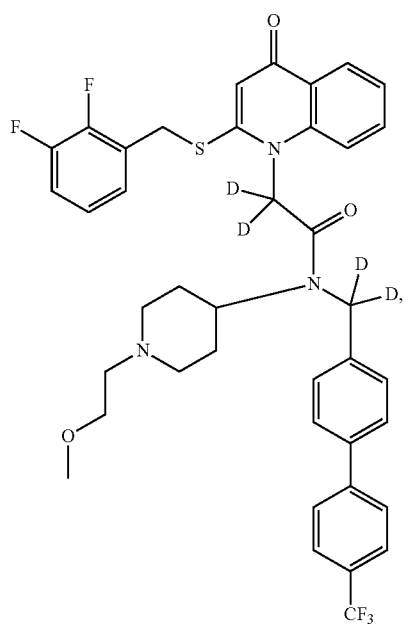
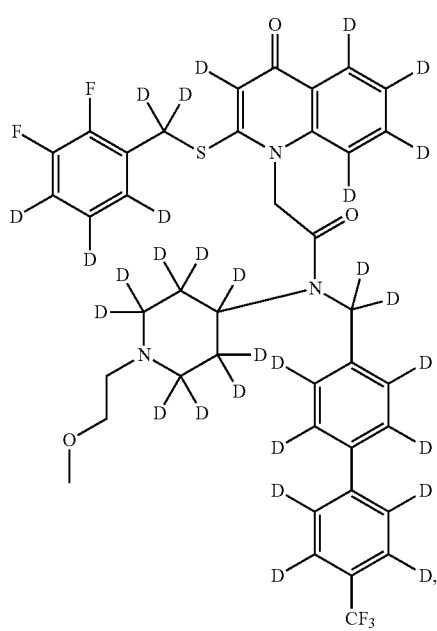
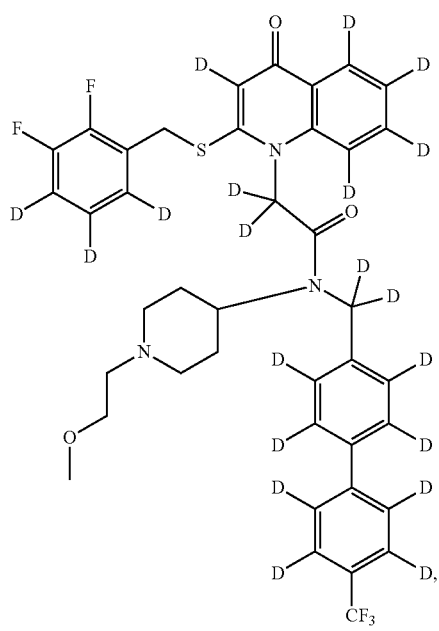

37
-continued
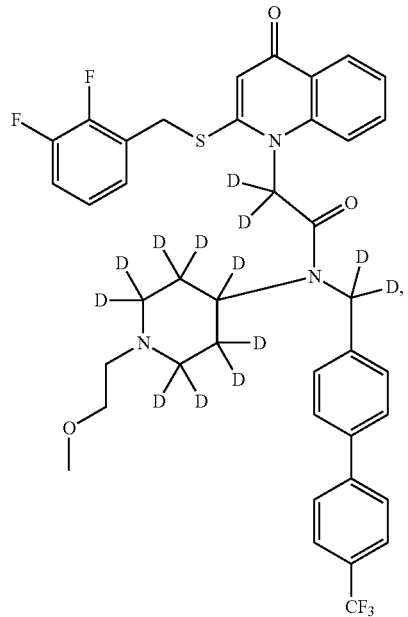
38
-continued
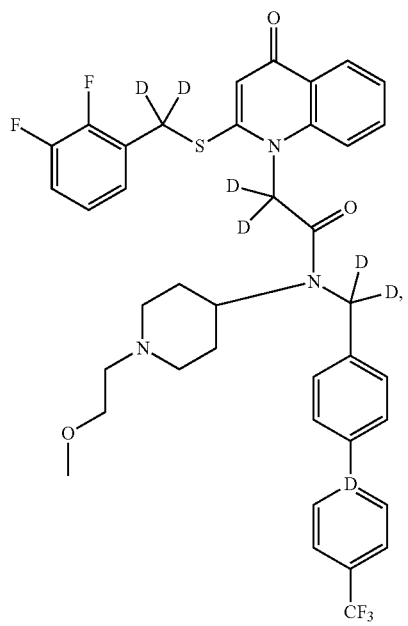
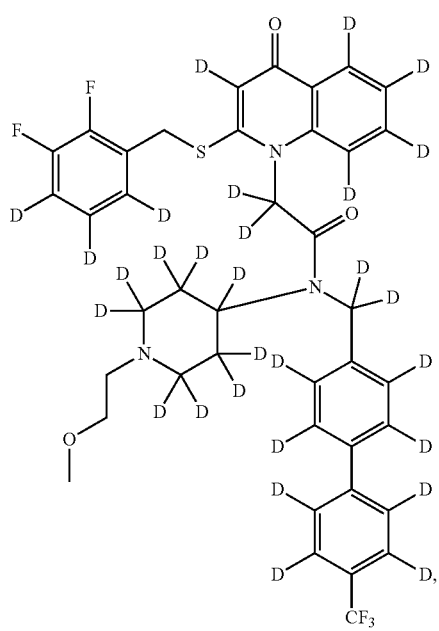
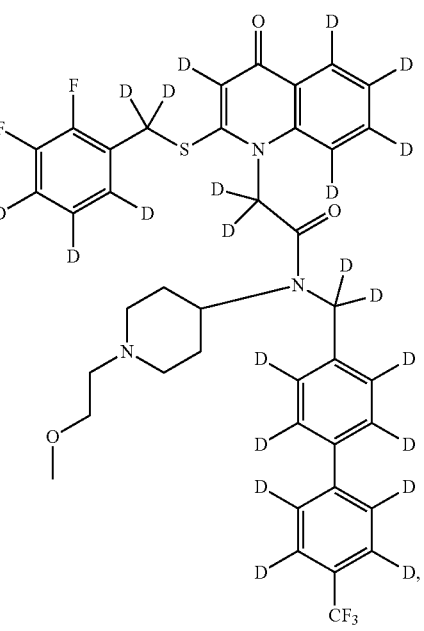

39
-continued
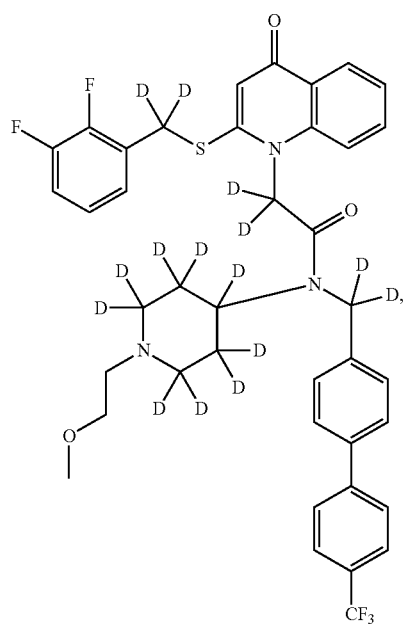
40
-continued
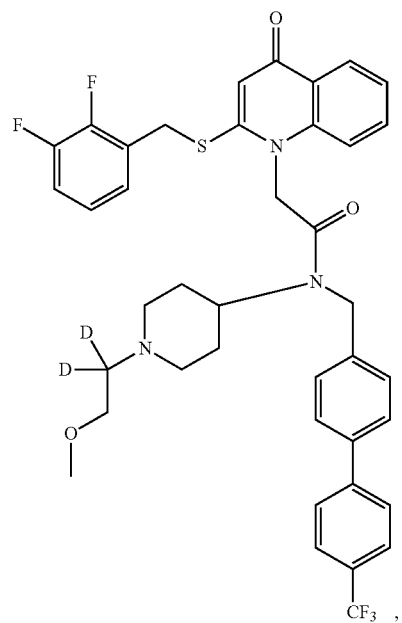
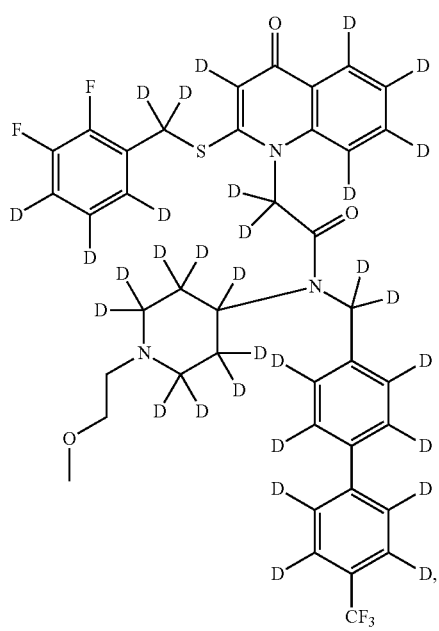
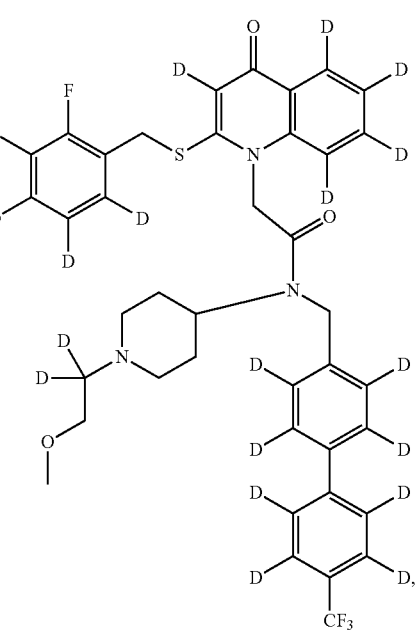

41
-continued
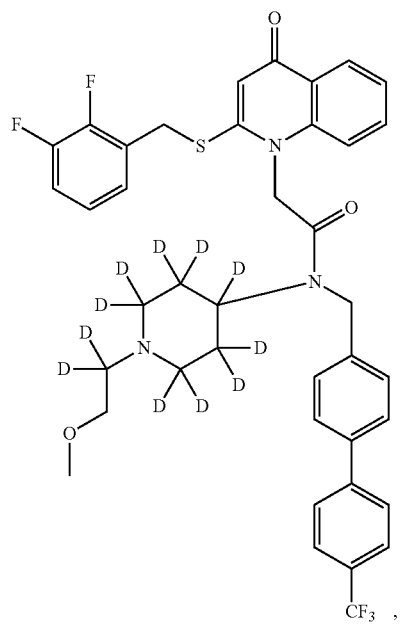
42
-continued
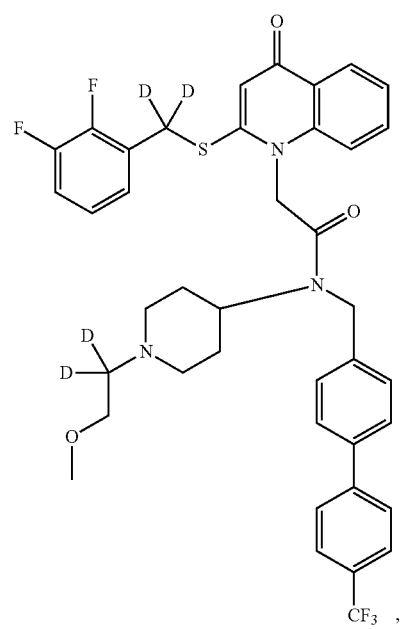
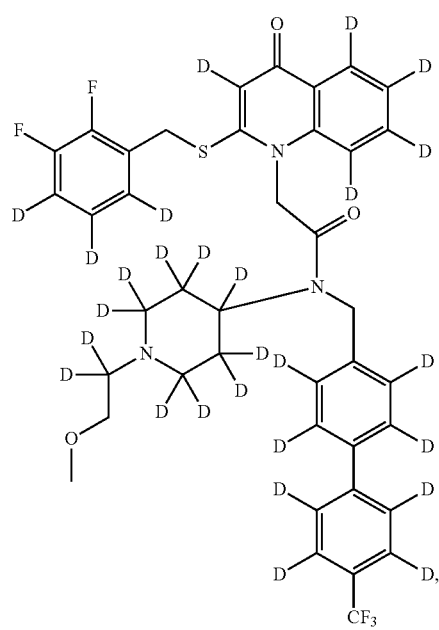
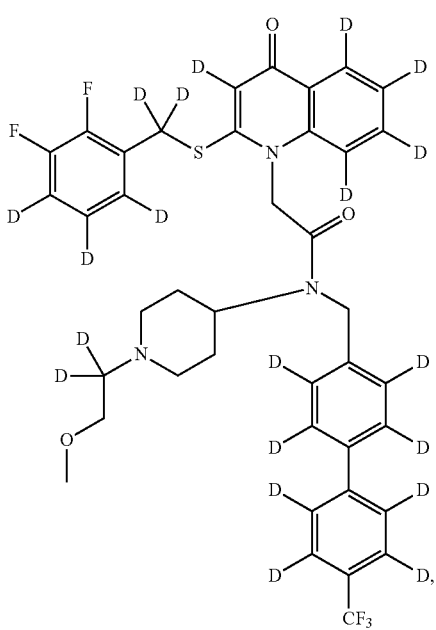

43
-continued
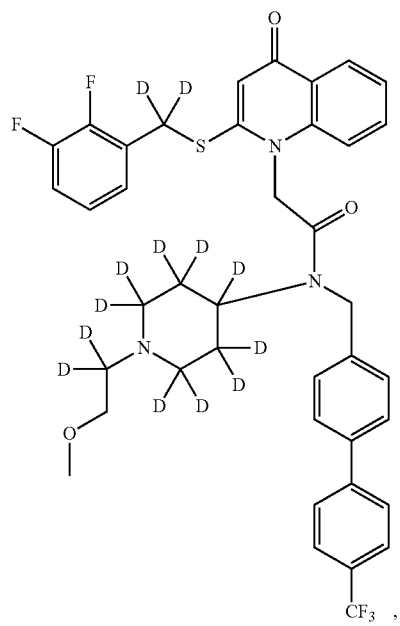
44
-continued
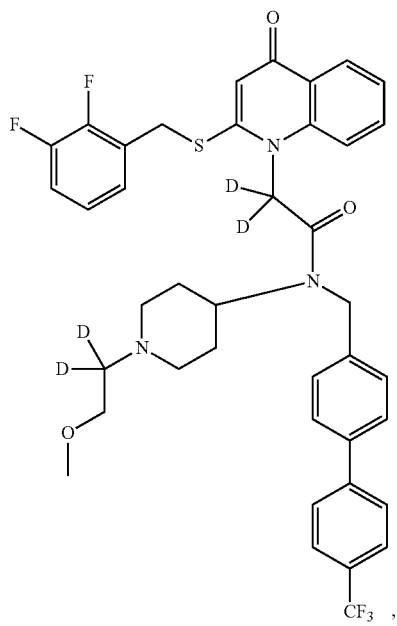
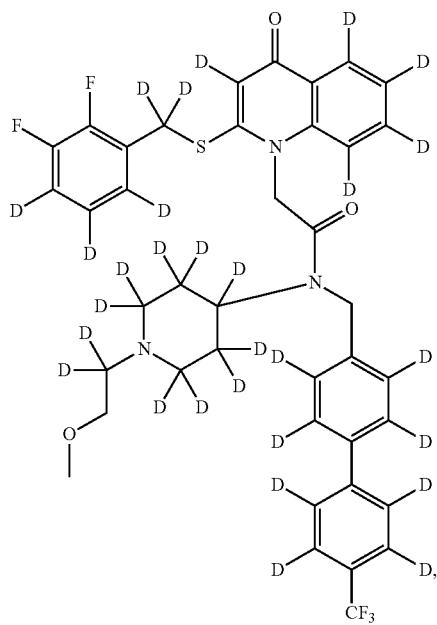
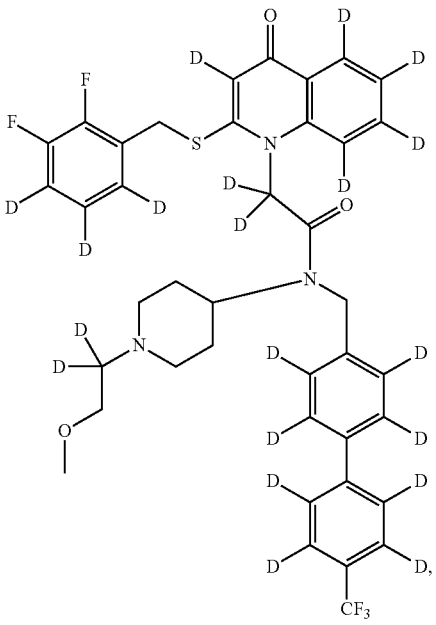

45
-continued
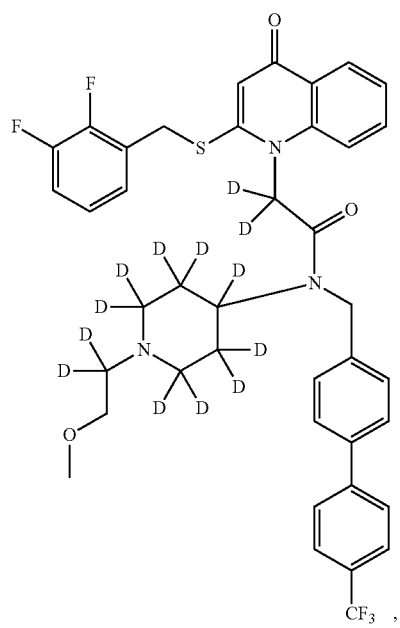
46
-continued
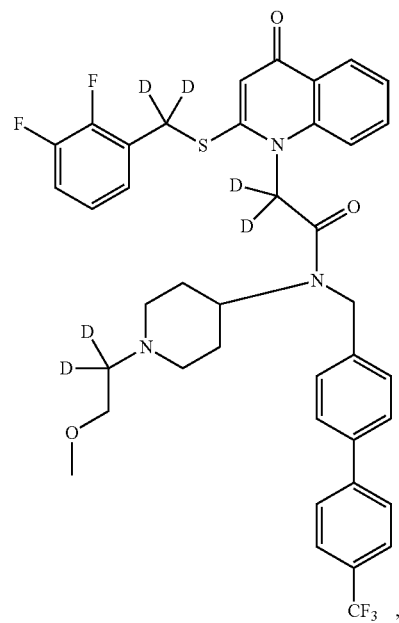
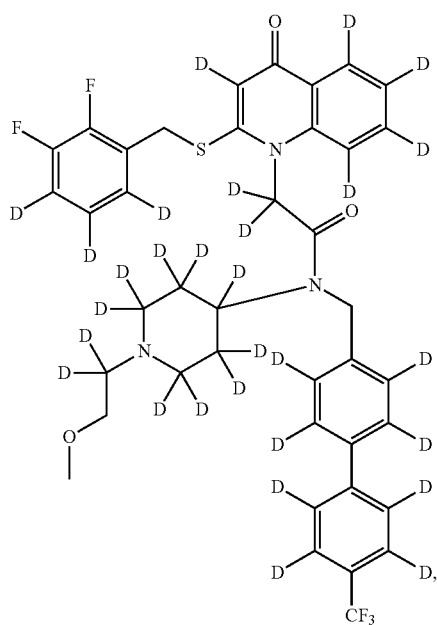
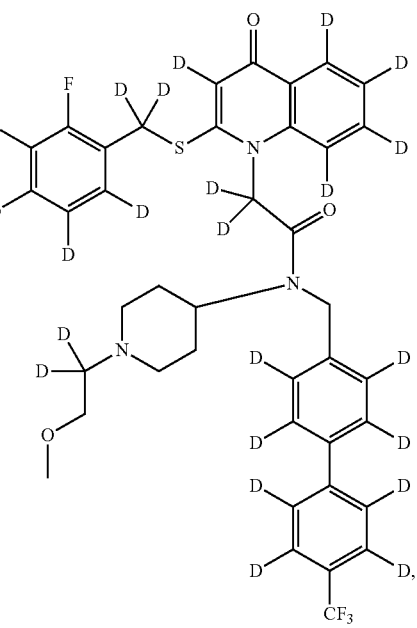

47
-continued
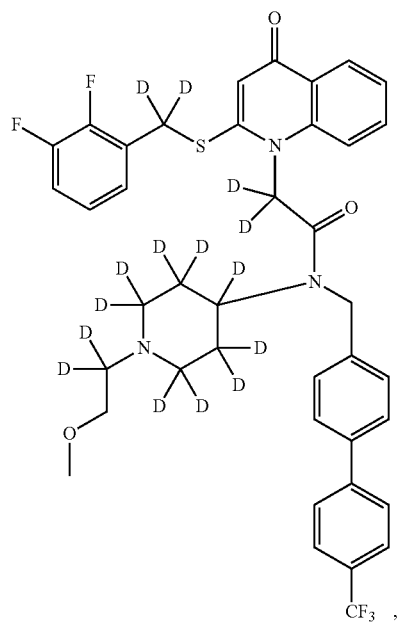
48
-continued
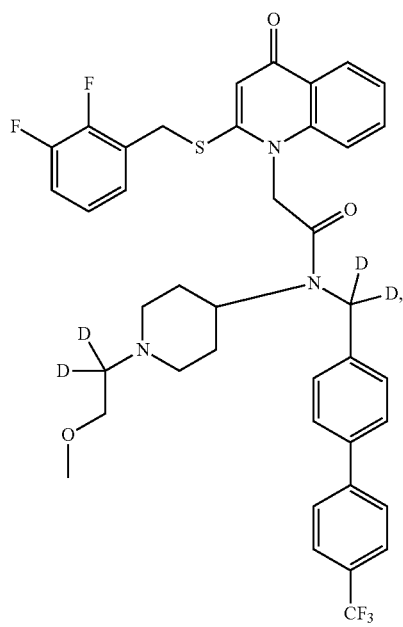
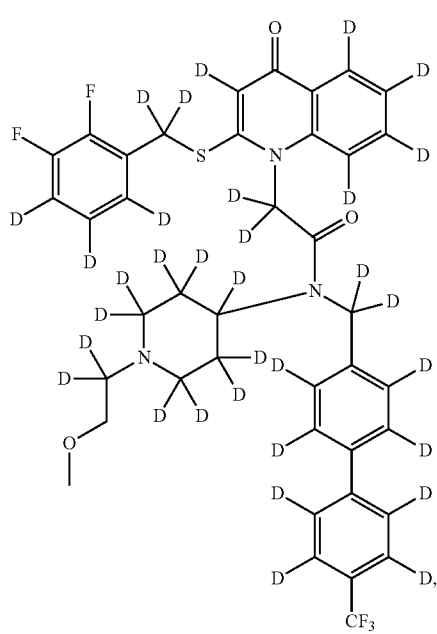
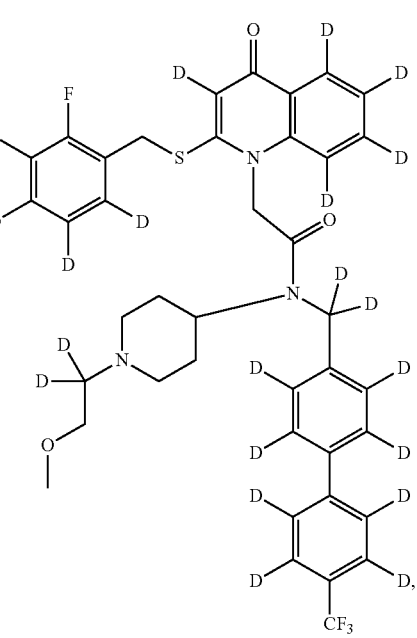

49
-continued
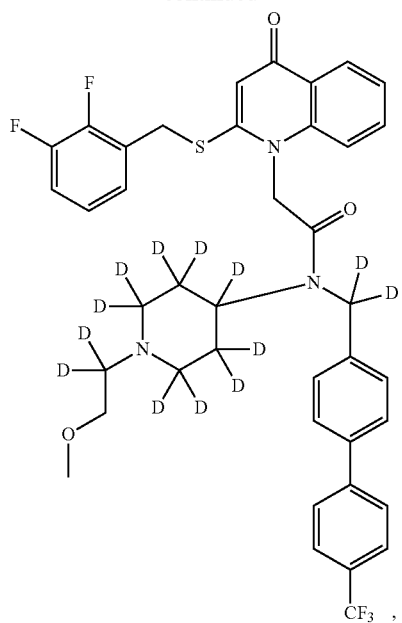
50
-continued
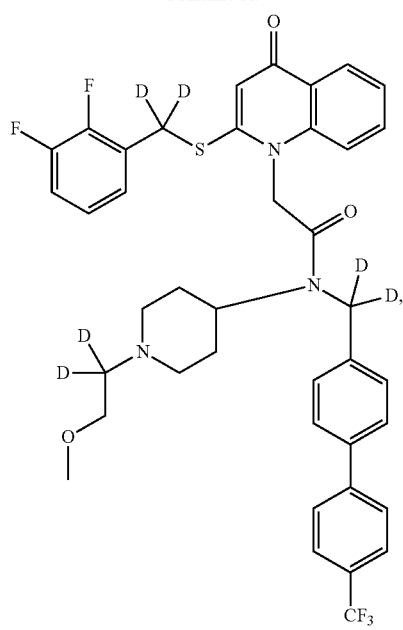
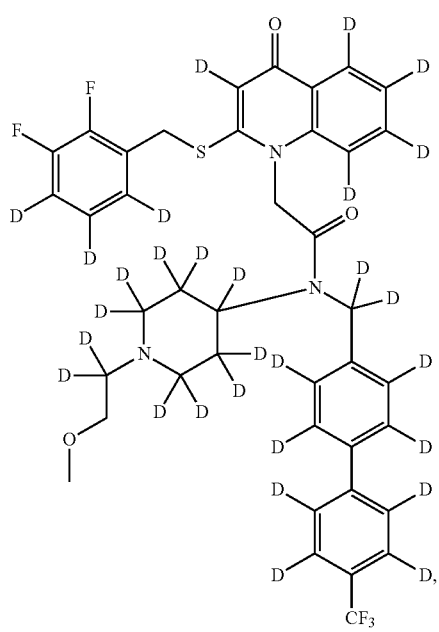
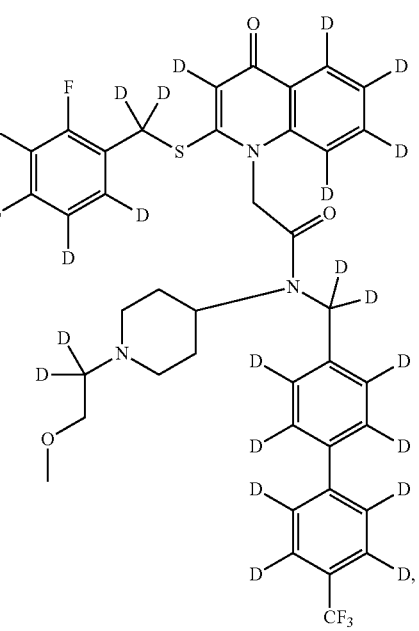

51
-continued
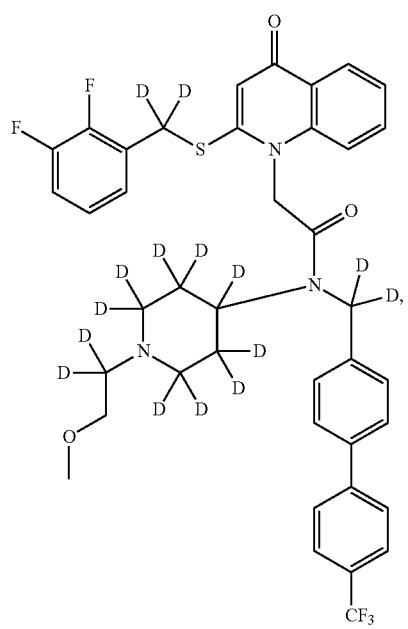
52
-continued
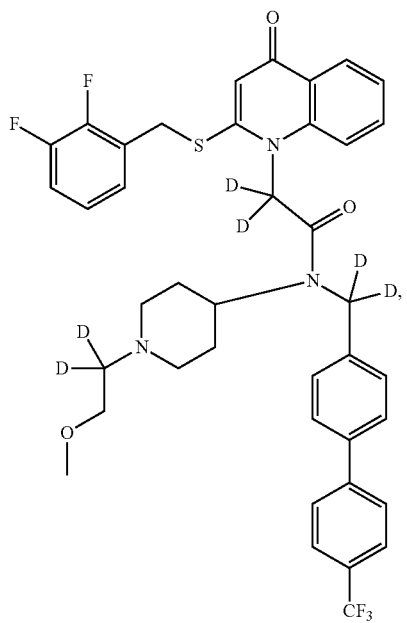
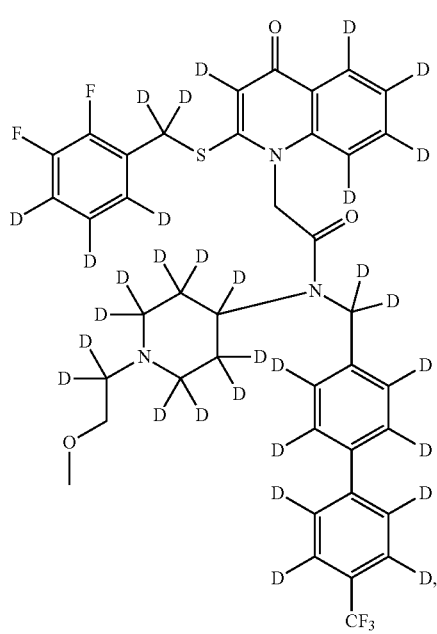
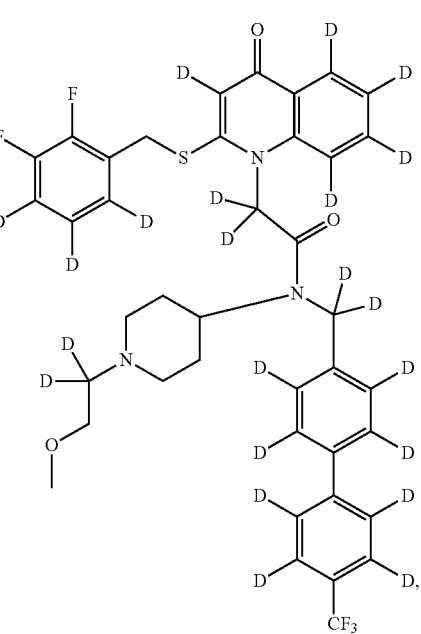

53
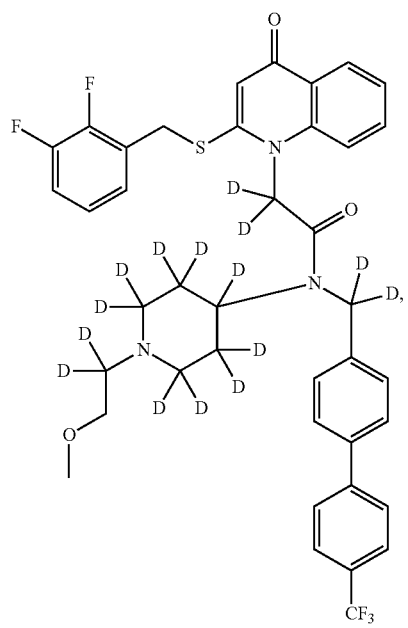
54
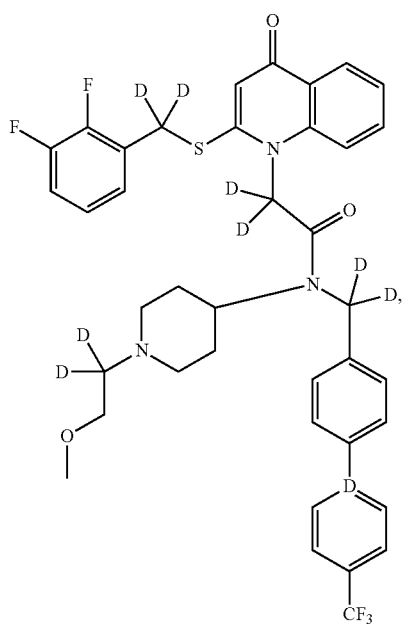
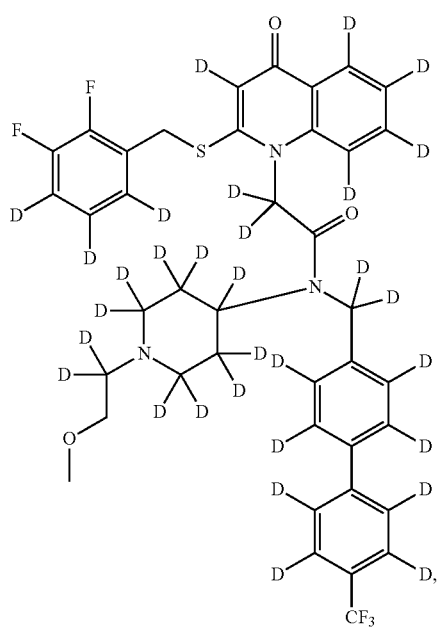
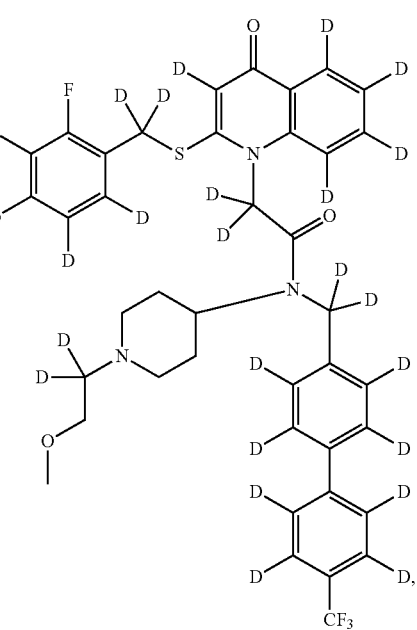

55
-continued
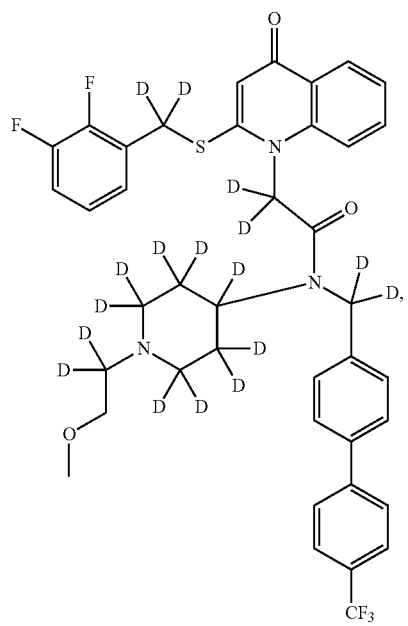
56
-continued
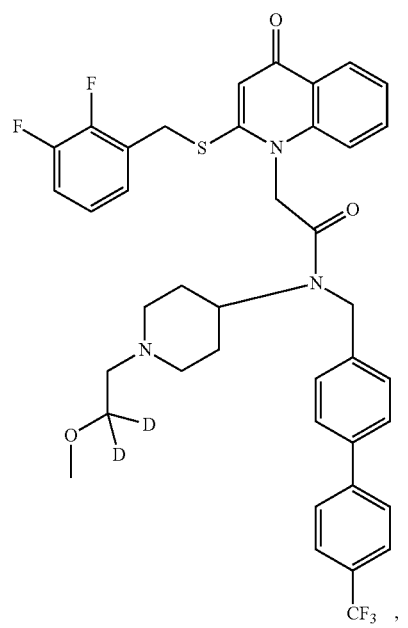
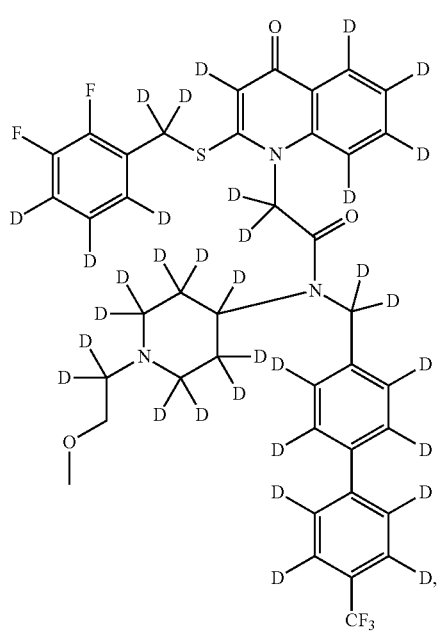
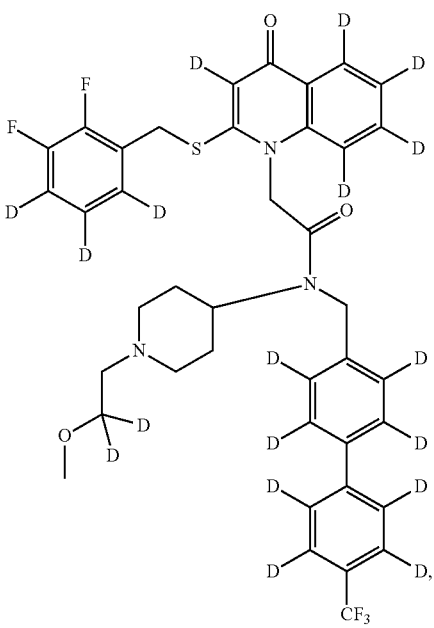

57
-continued
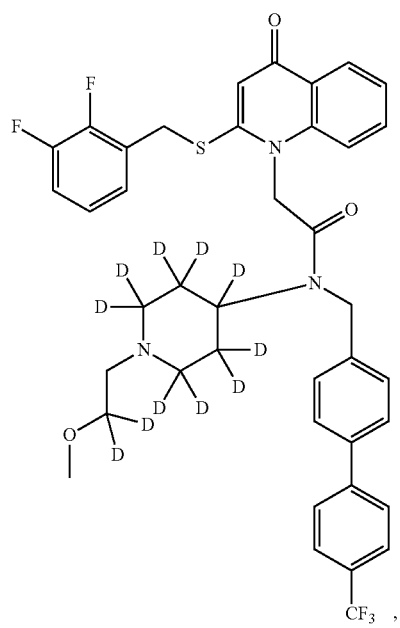
58
-continued
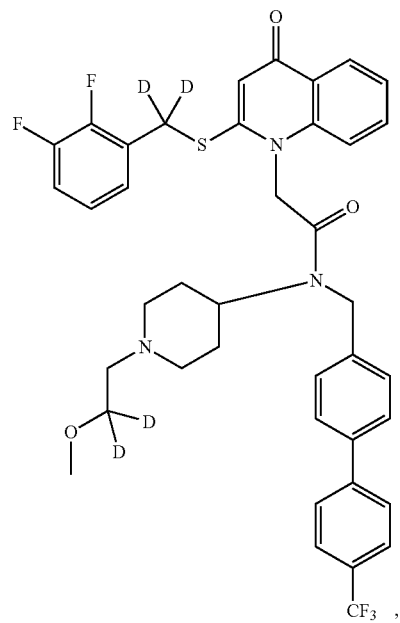
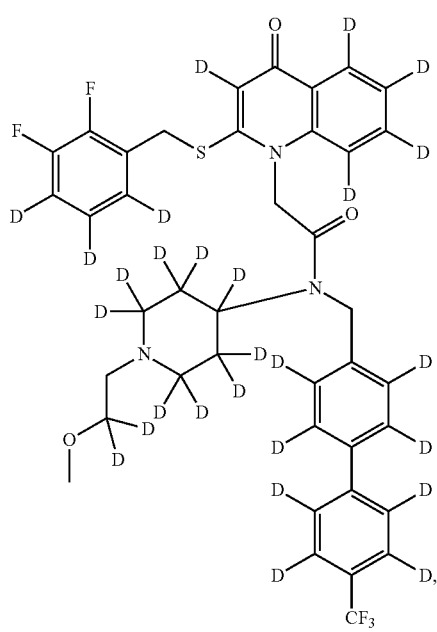
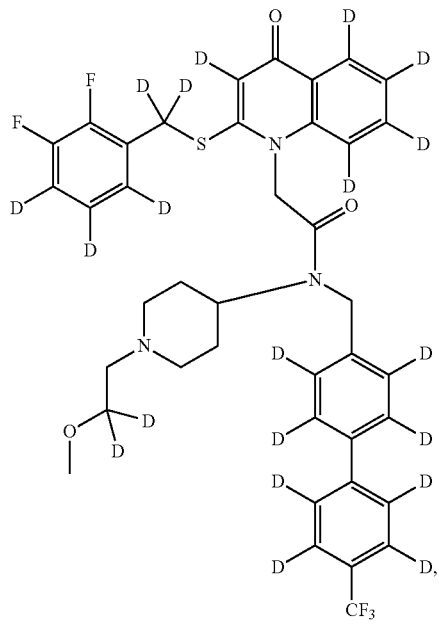

59
-continued
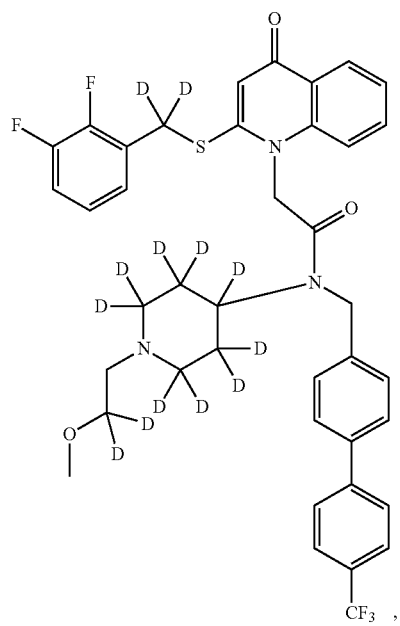
60
-continued
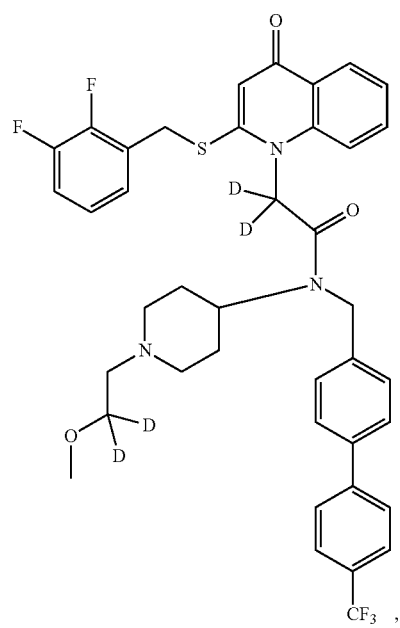

61
-continued
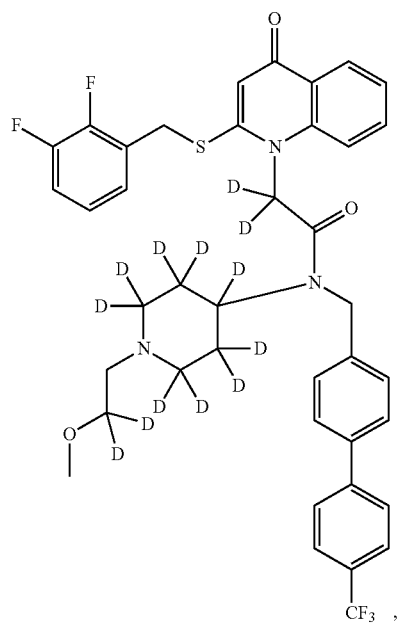
62
-continued
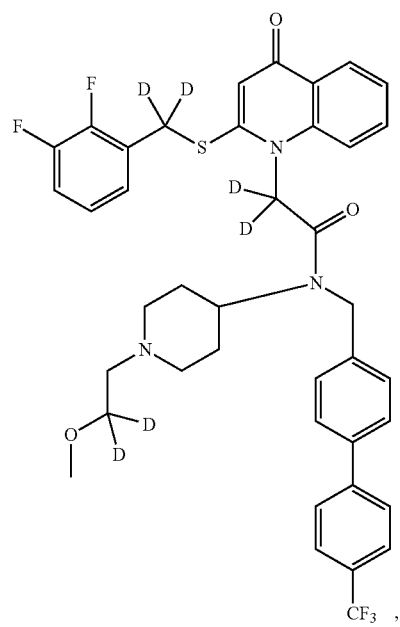

63
-continued
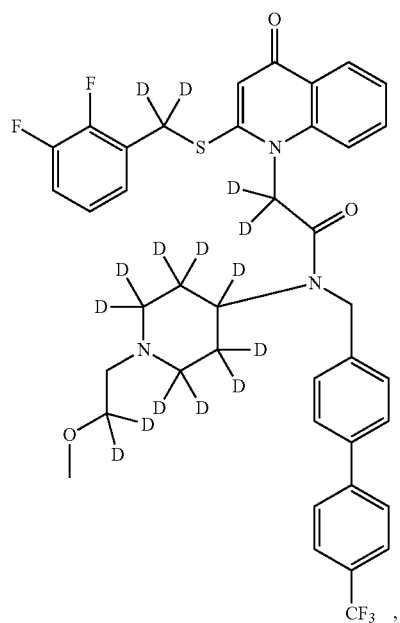
64
-continued
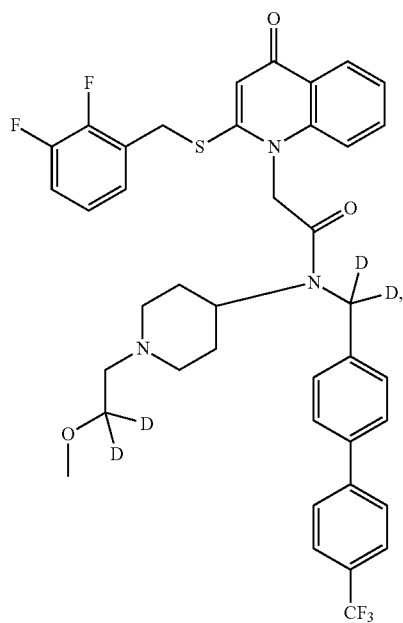
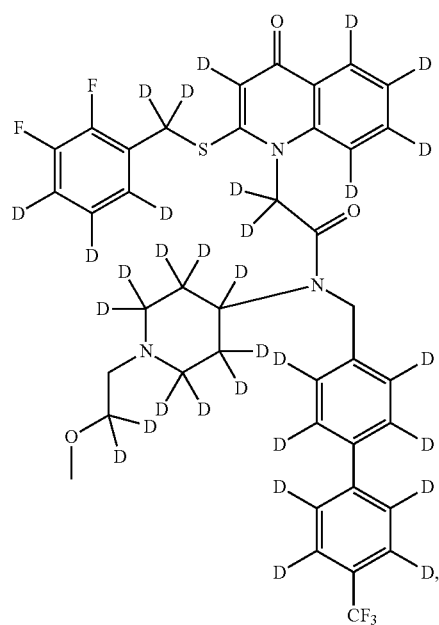
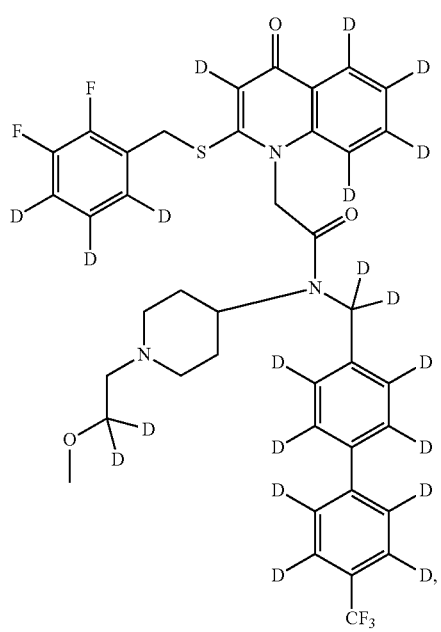

65
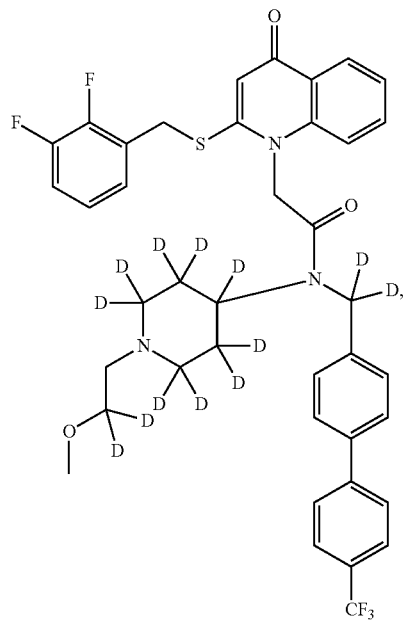
66
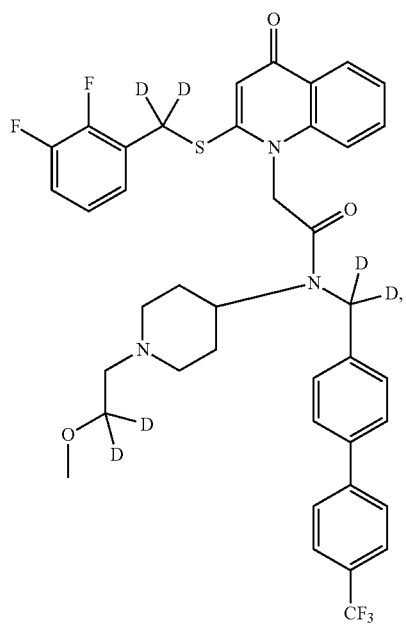
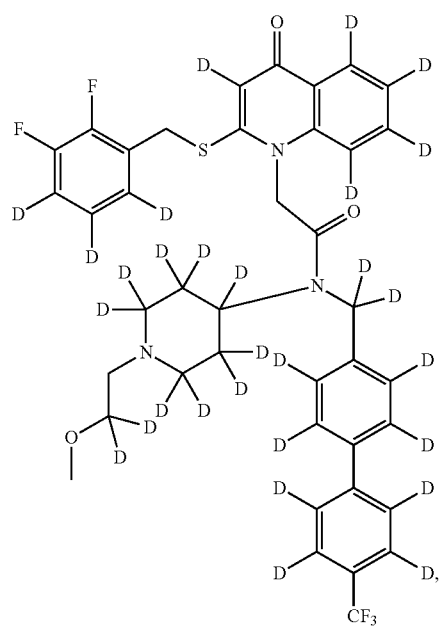
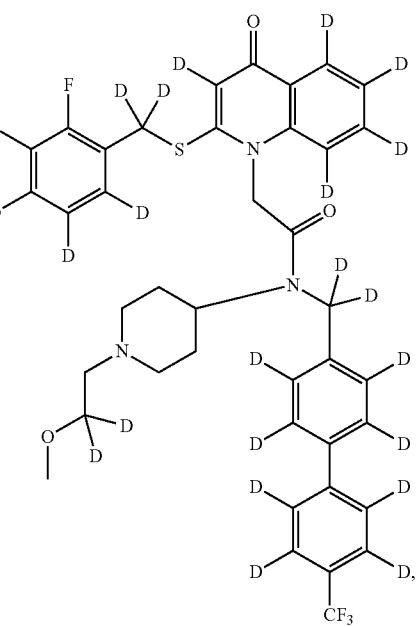

67
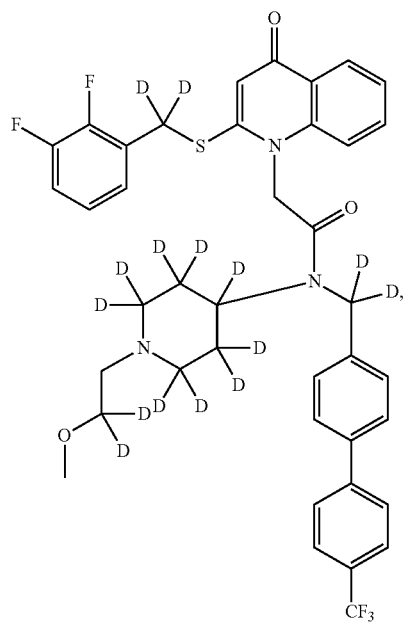
68
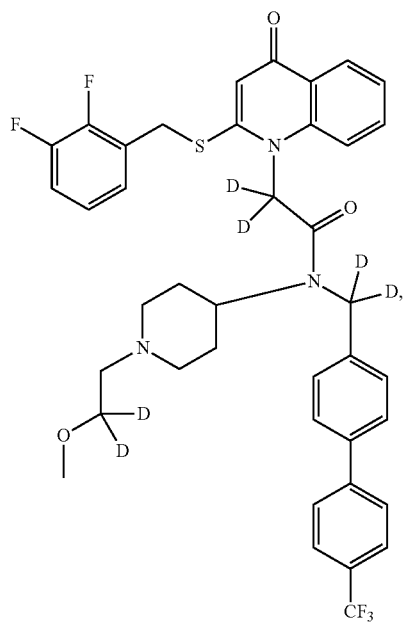
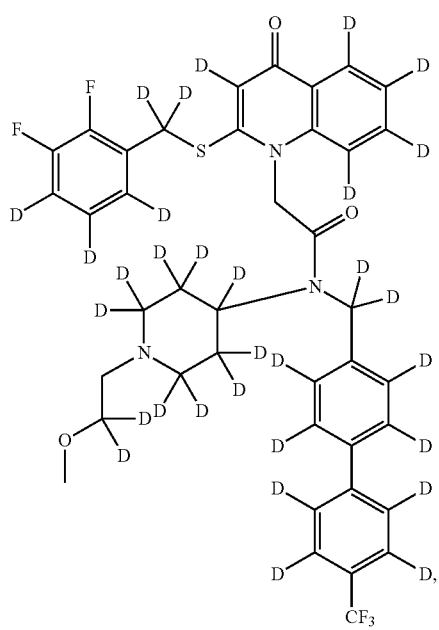
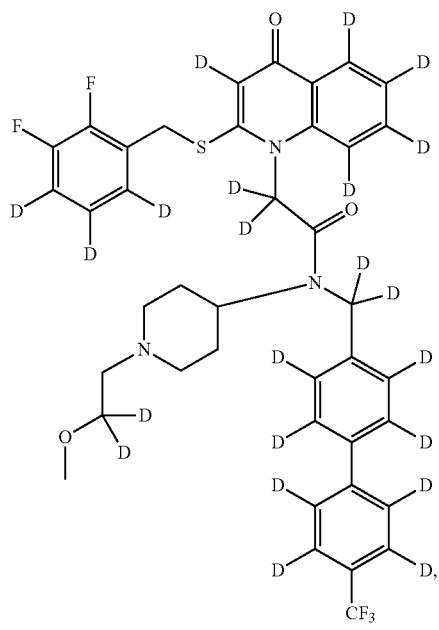

69
-continued
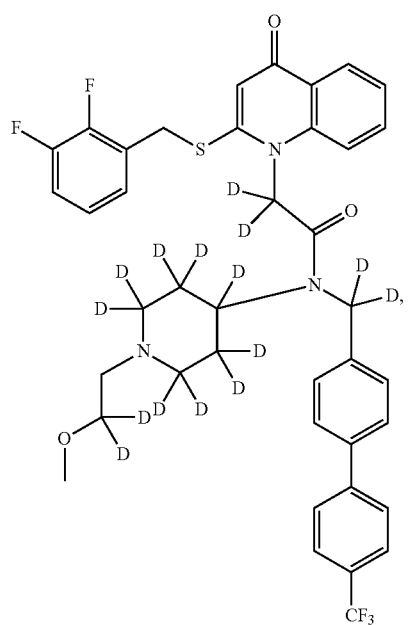
70
-continued
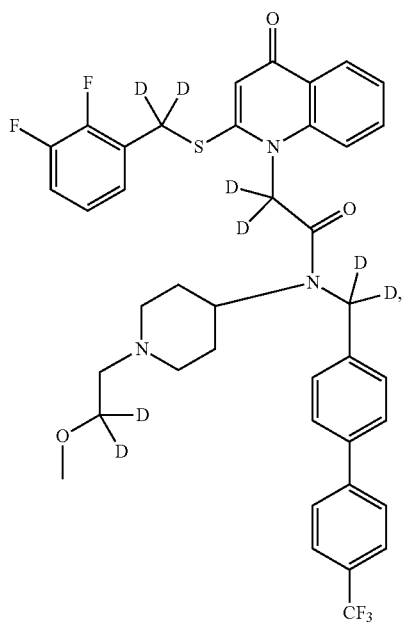

71
-continued
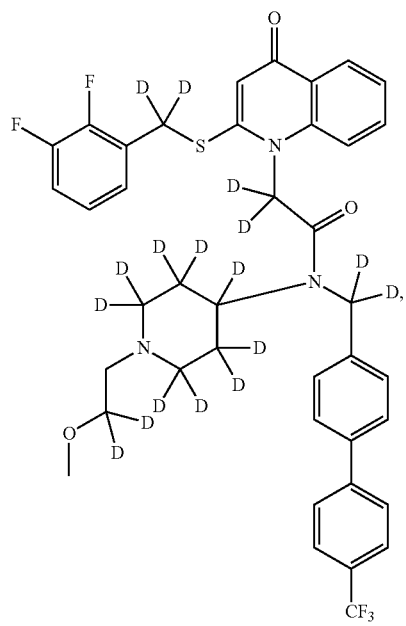
72
-continued
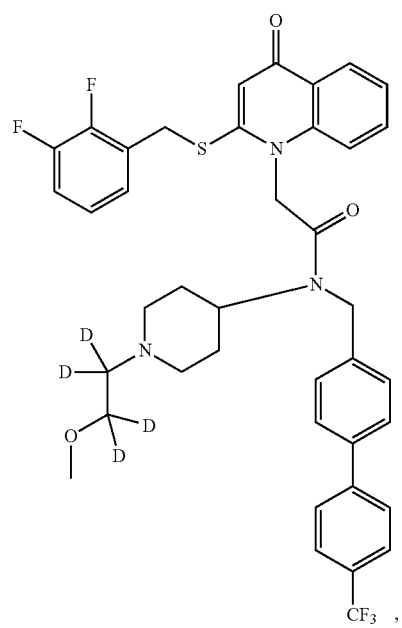
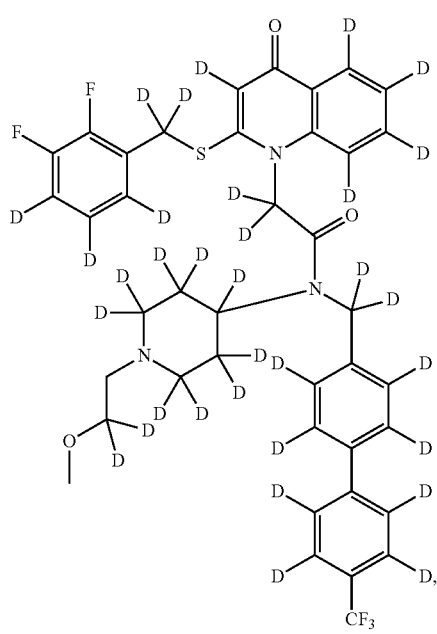
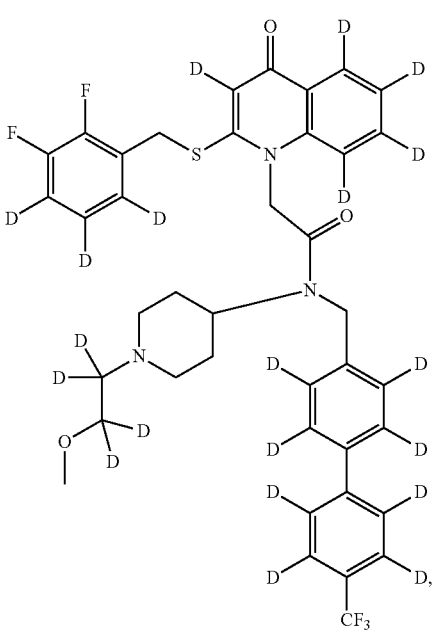

73
-continued
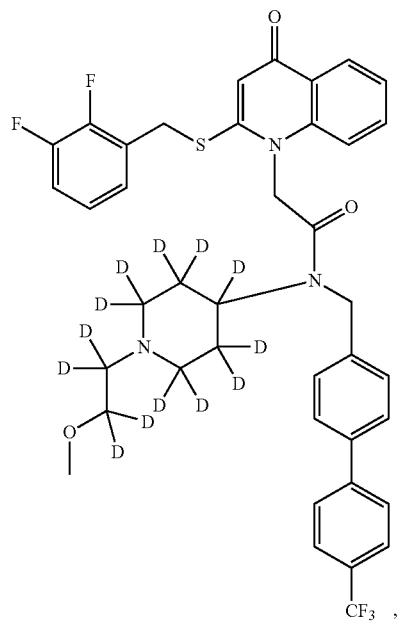
74
-continued
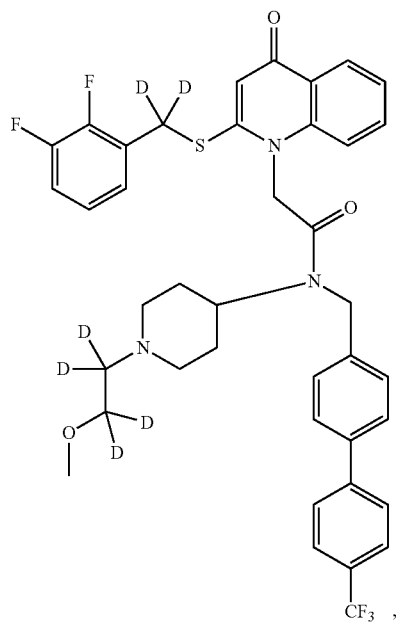
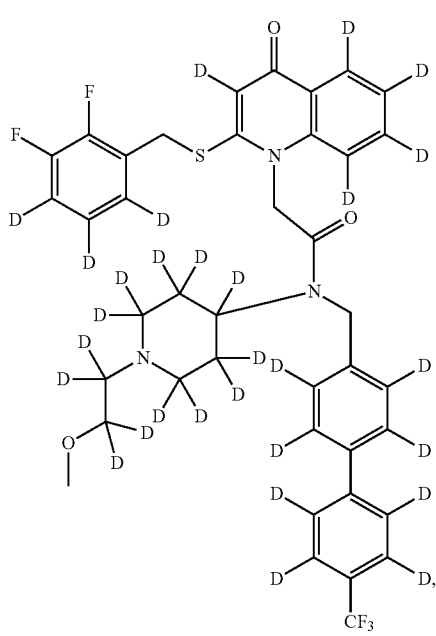
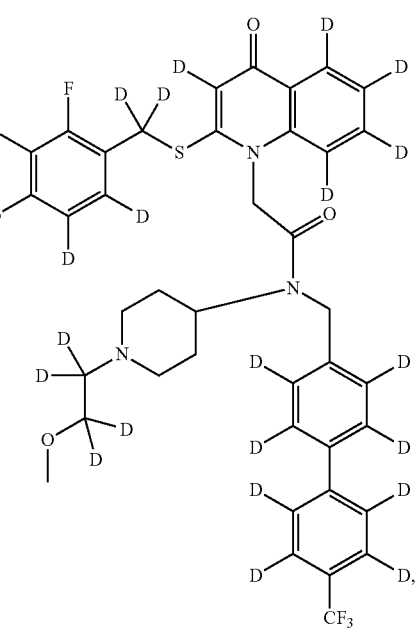

75
-continued
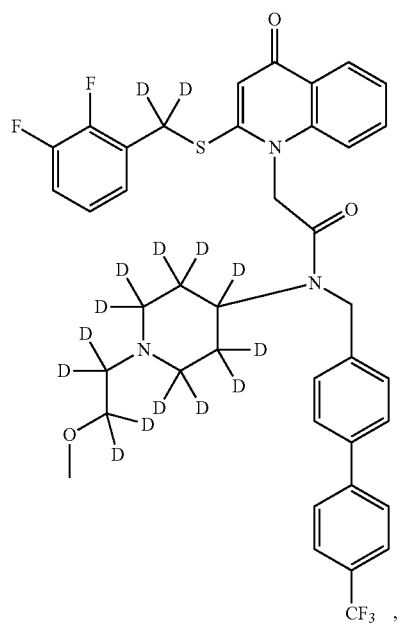
76
-continued
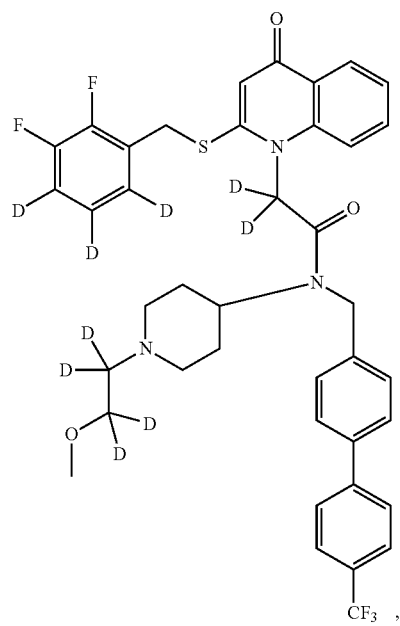
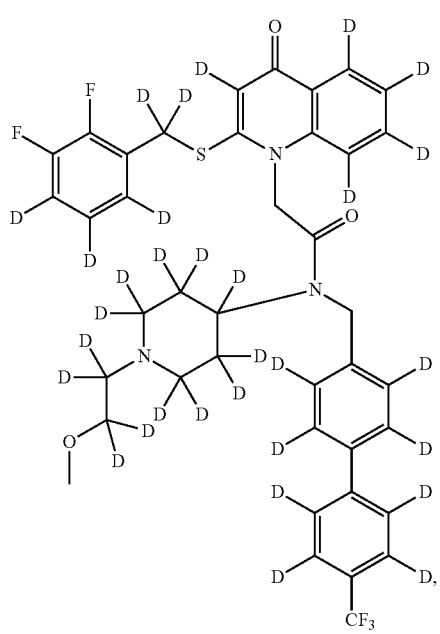
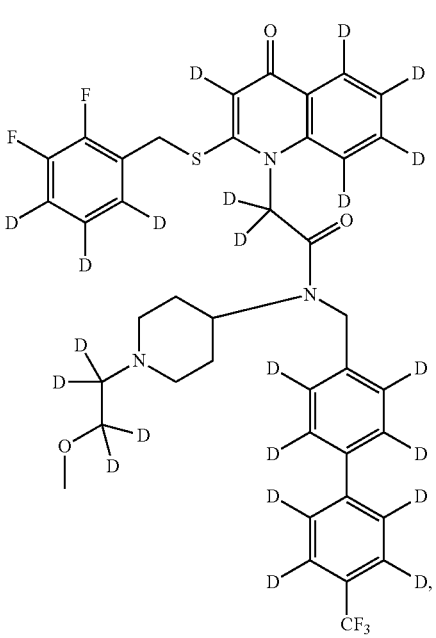

77
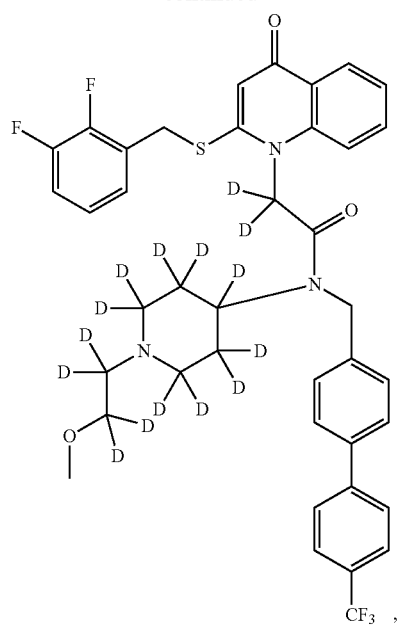
,
78
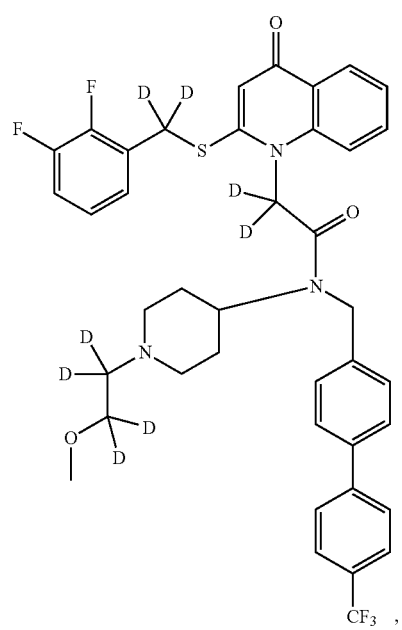
,
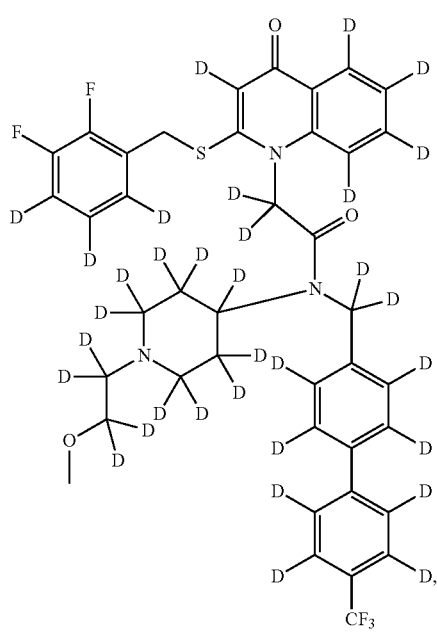
,
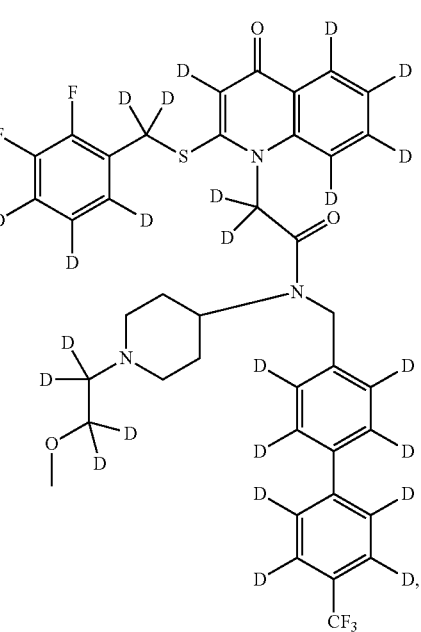
,

79
-continued
80
-continued
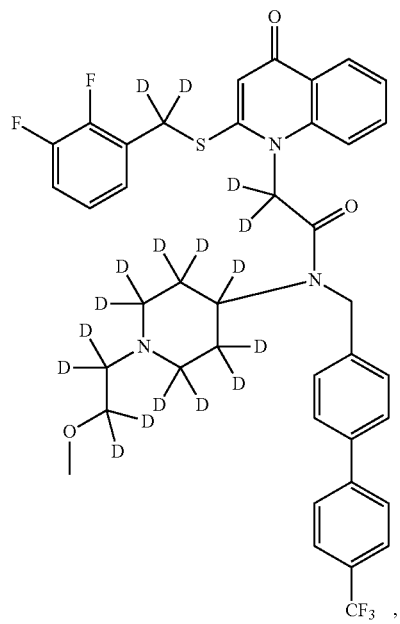
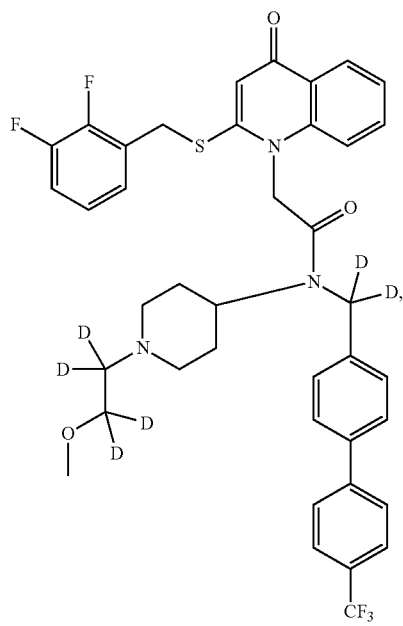

81
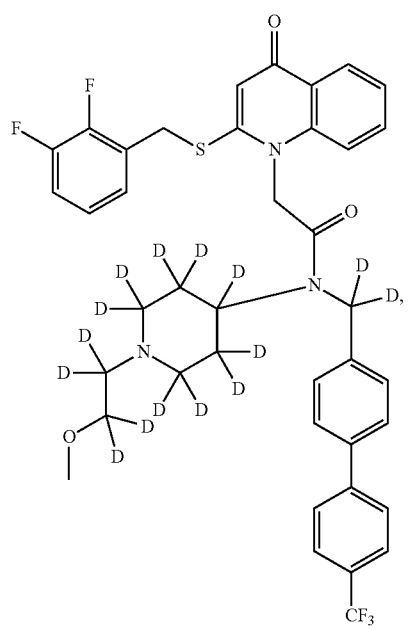
82
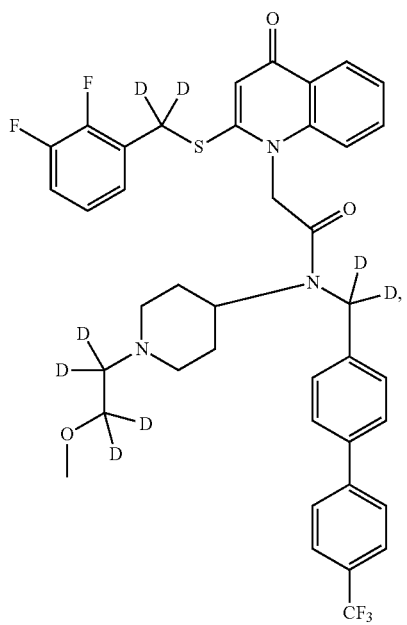
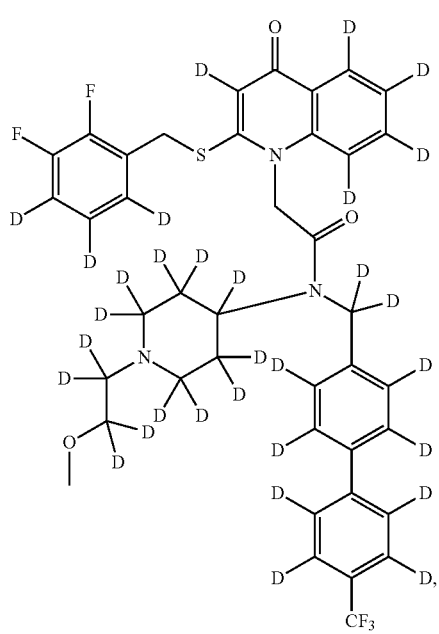
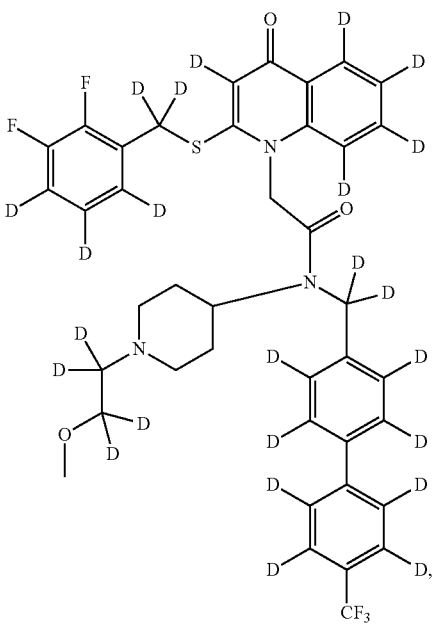

83
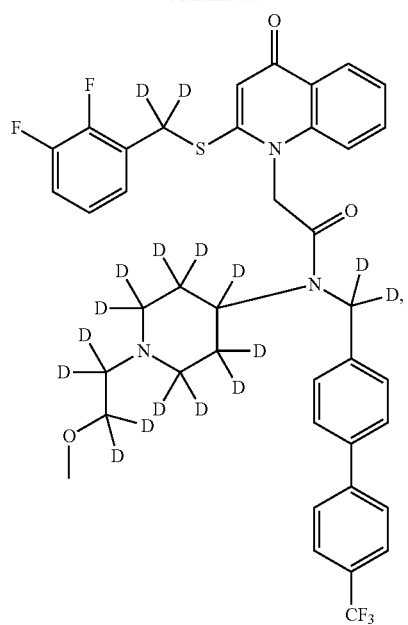
84
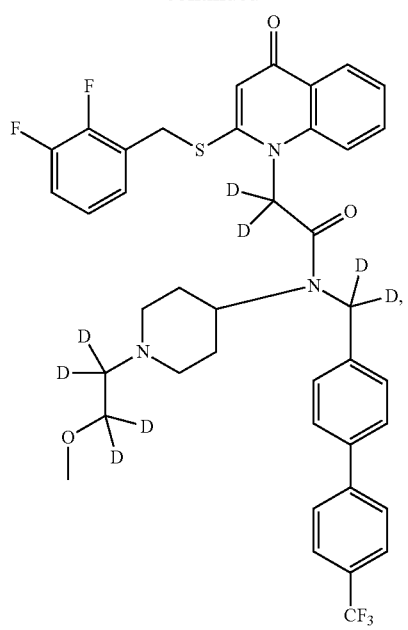
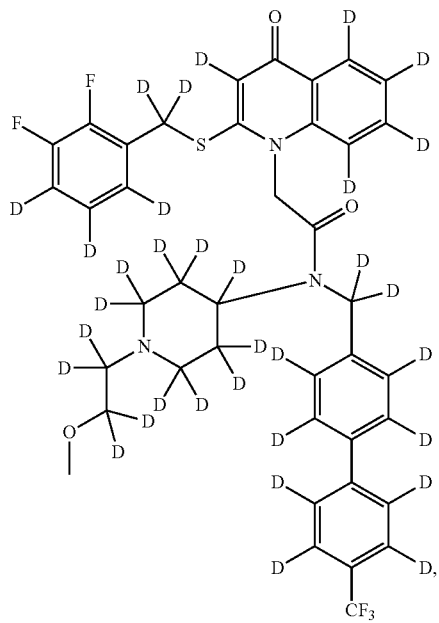
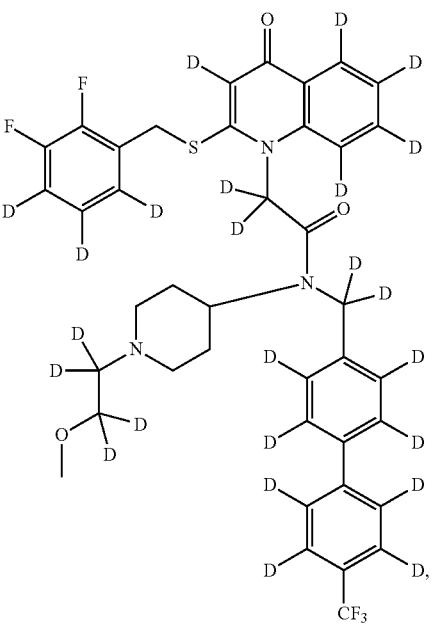

85
-continued
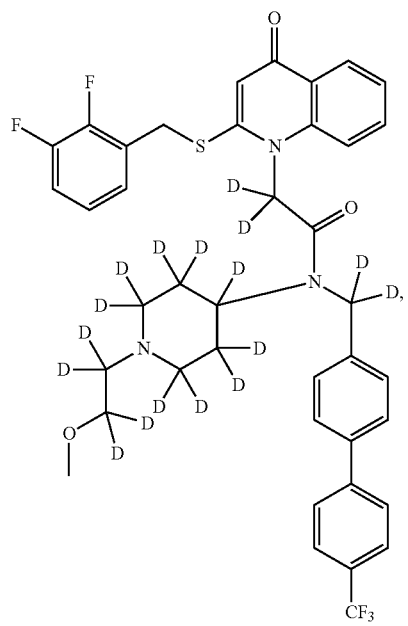
86
-continued
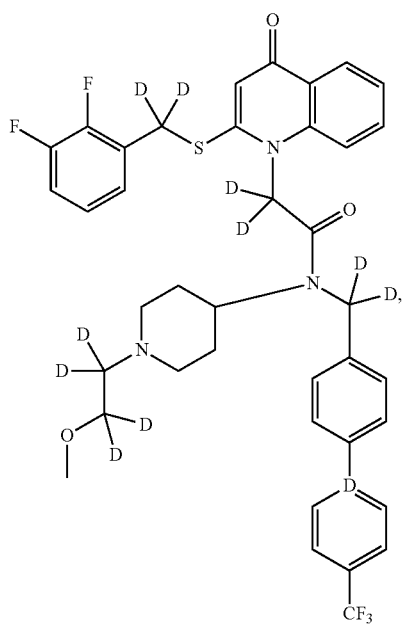
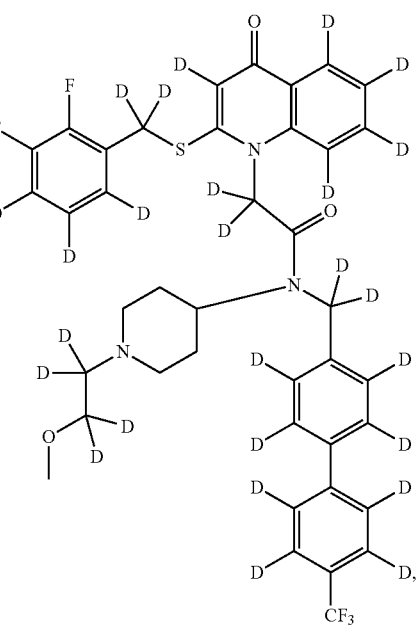

87
-continued
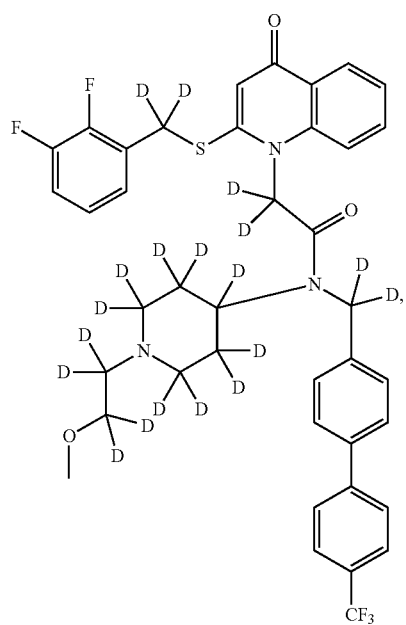
88
-continued
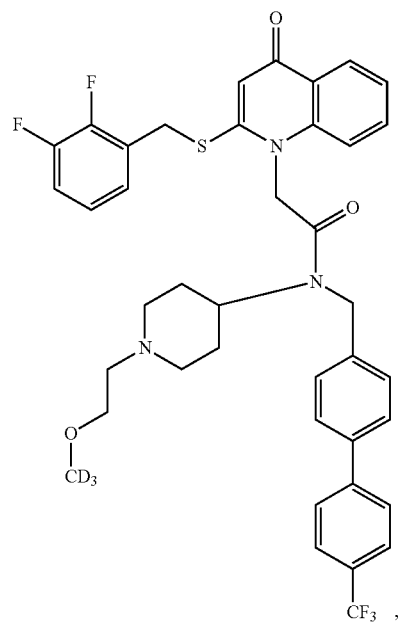
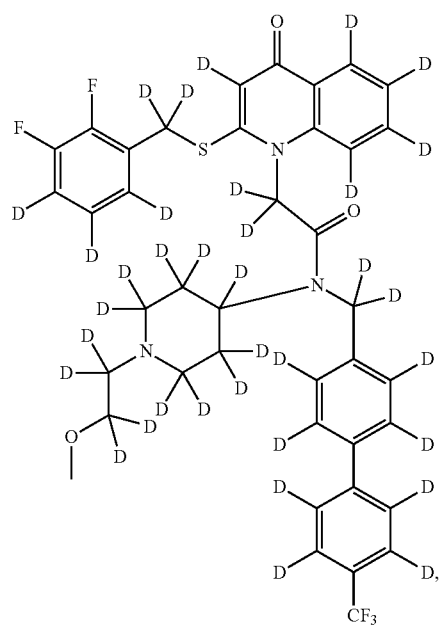
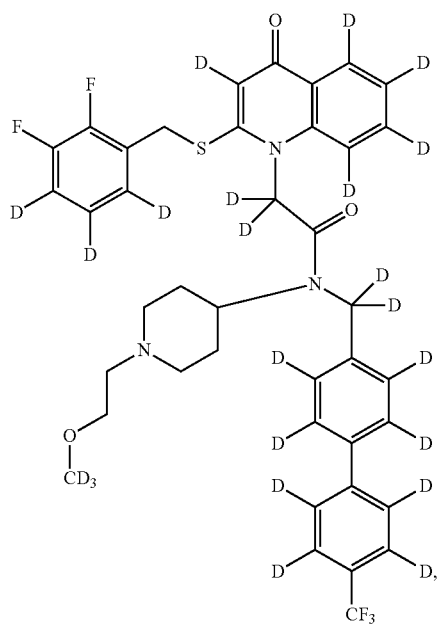

89
-continued
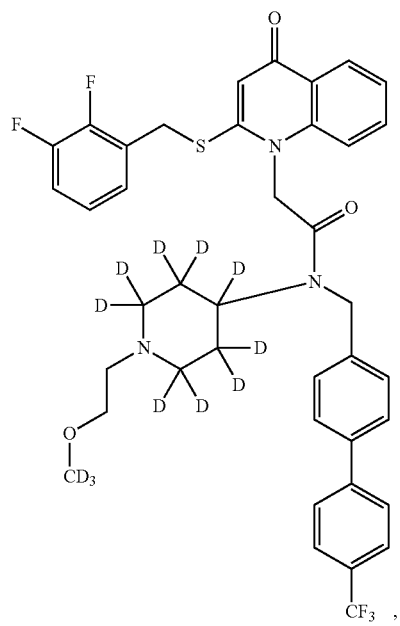
90
-continued
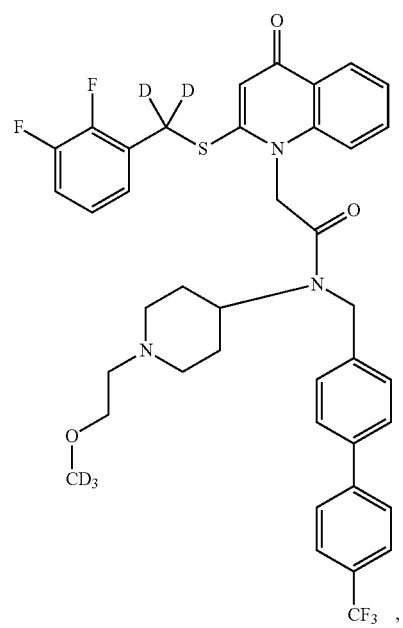
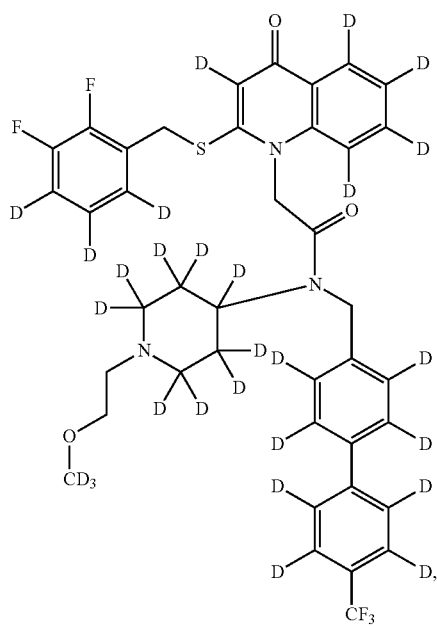
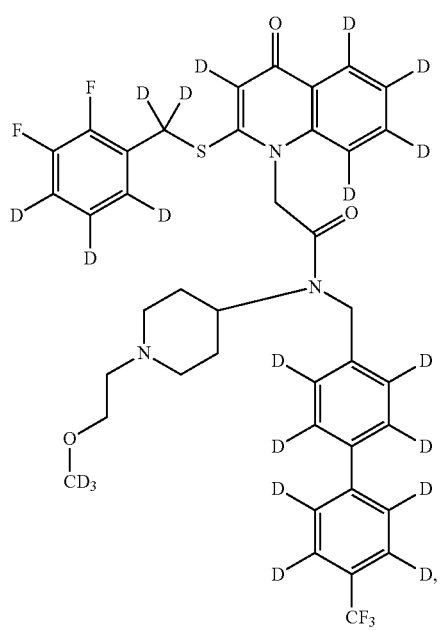

91
-continued
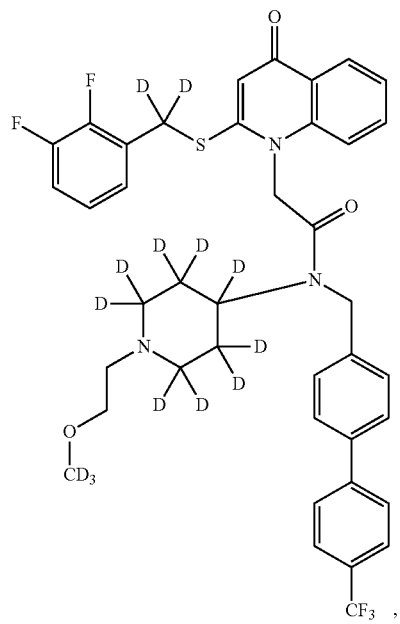
92
-continued
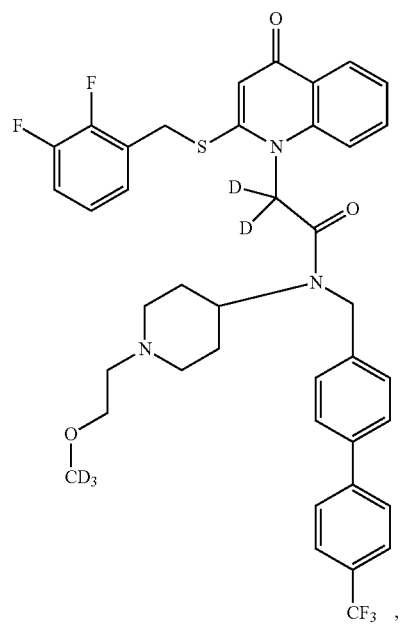
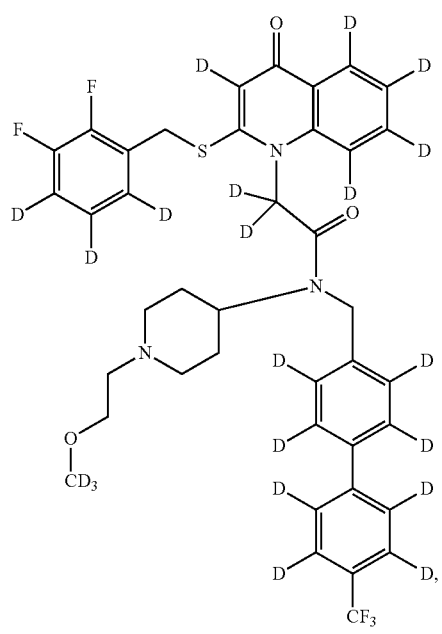

93
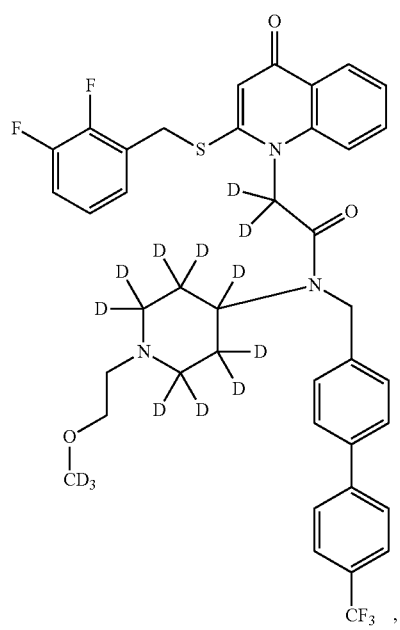
94
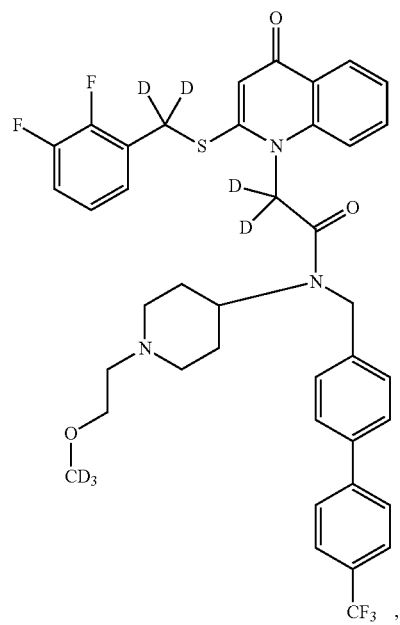
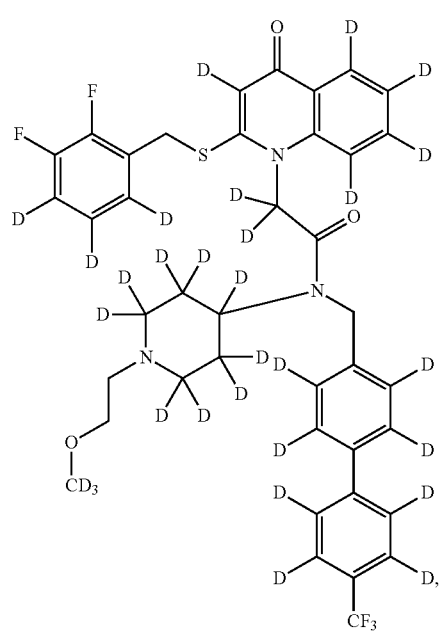
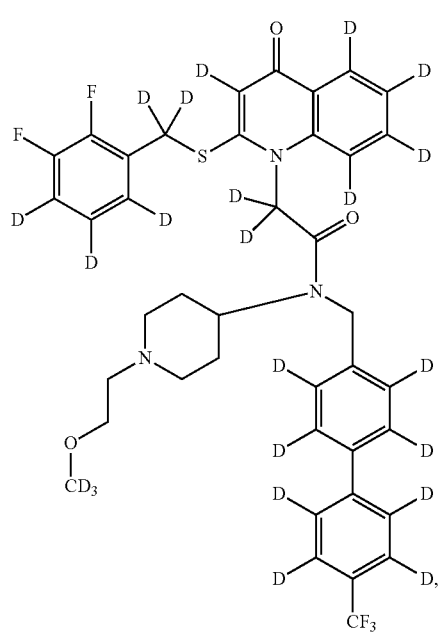

95
-continued
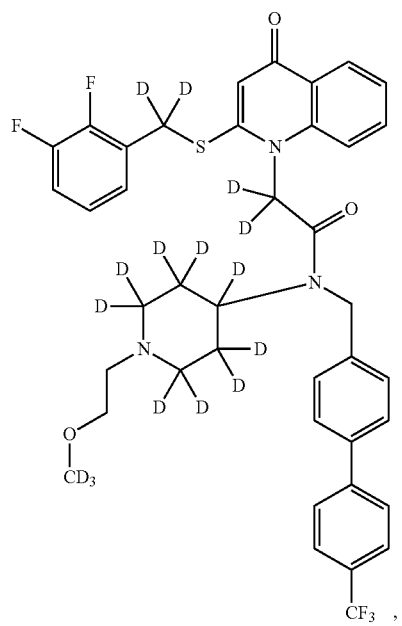
96
-continued
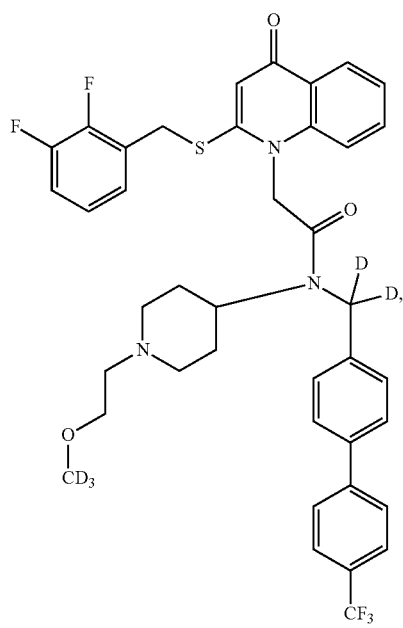
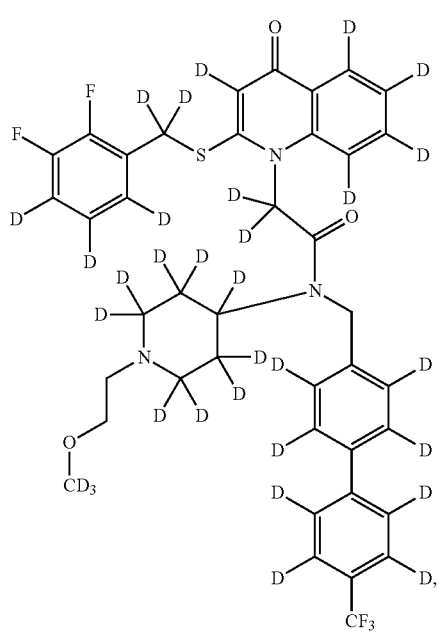
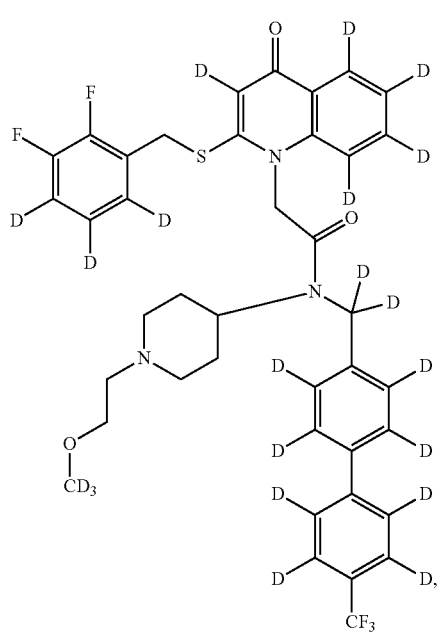

97
-continued
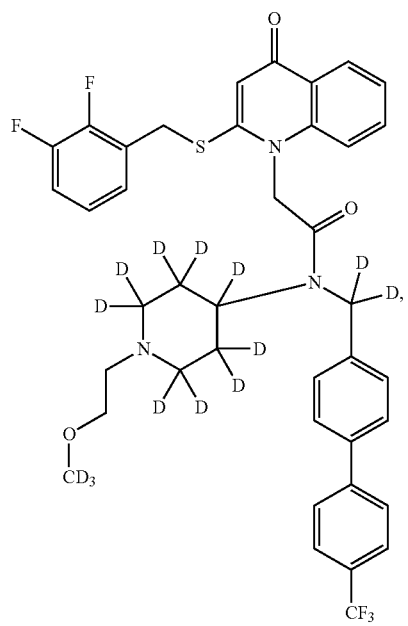
98
-continued
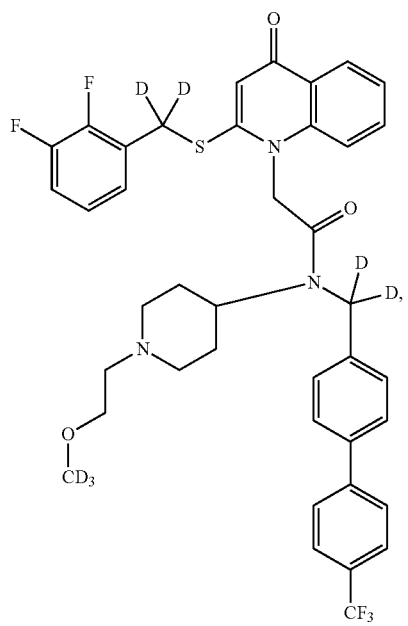
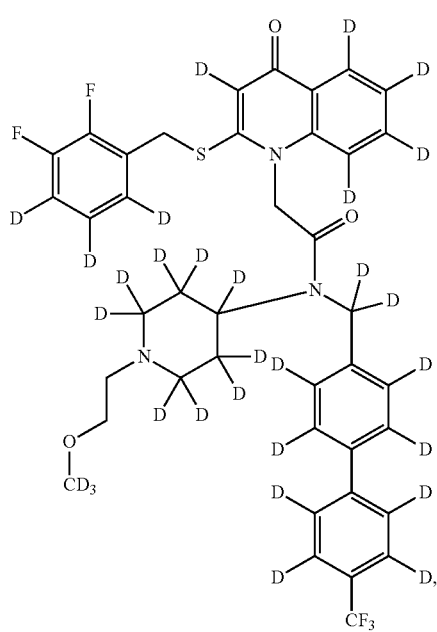
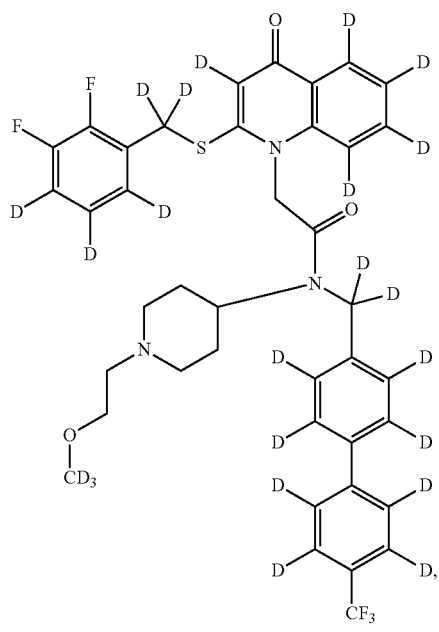

99
-continued
100
-continued
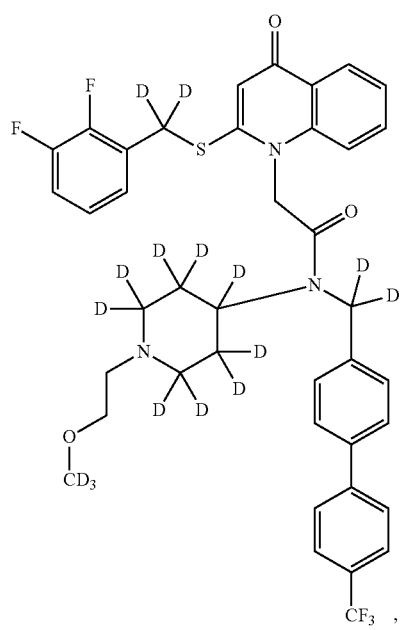
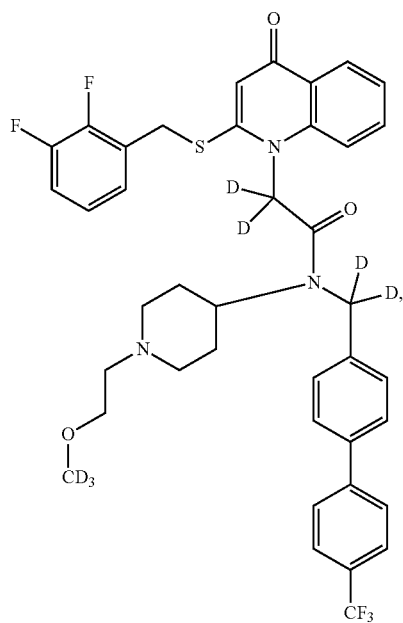
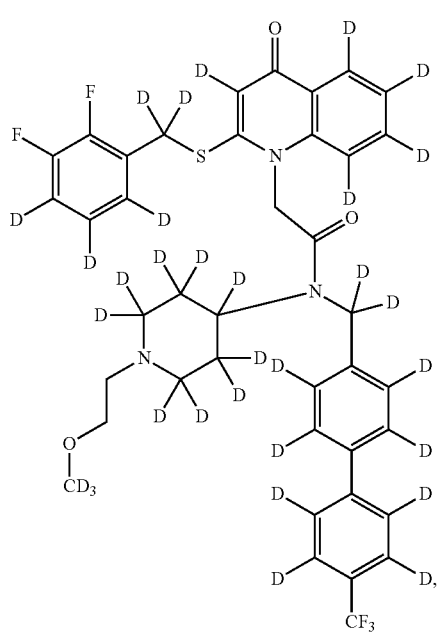

101
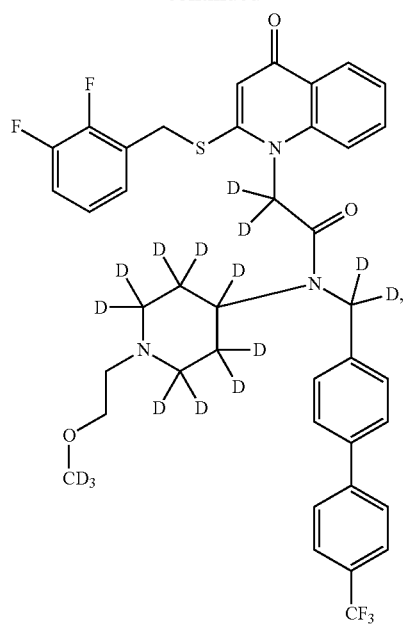
102
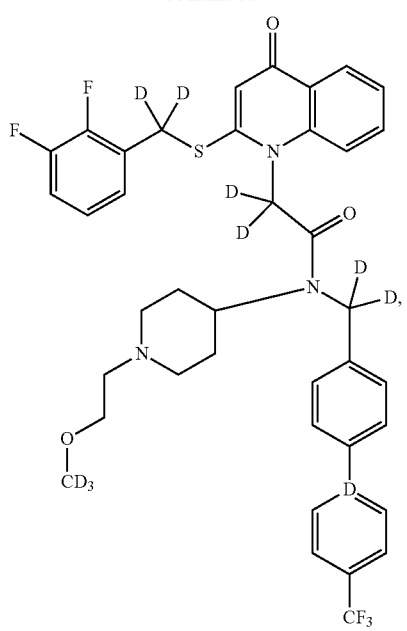
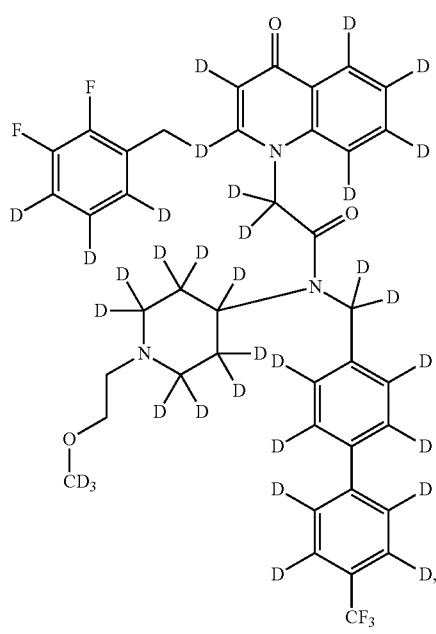
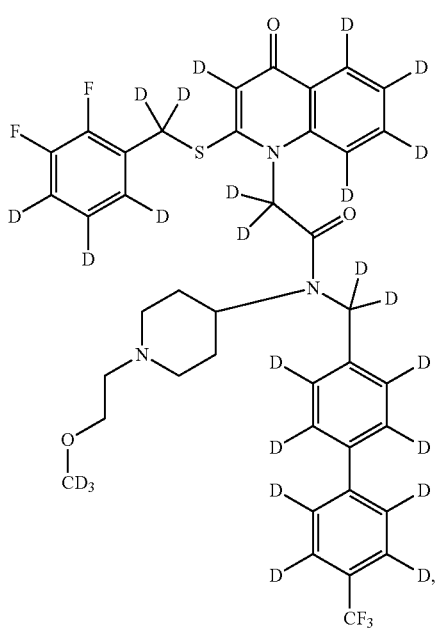

103
-continued
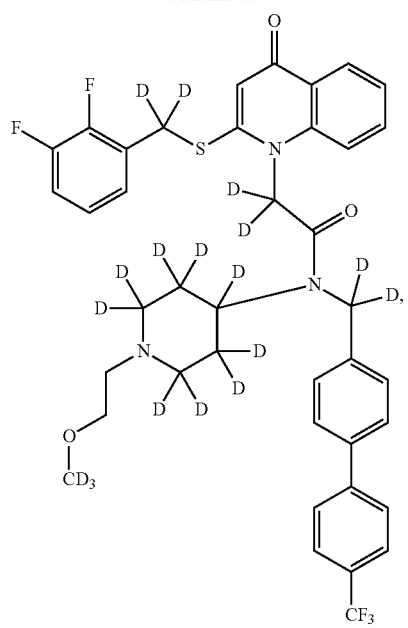
104
-continued
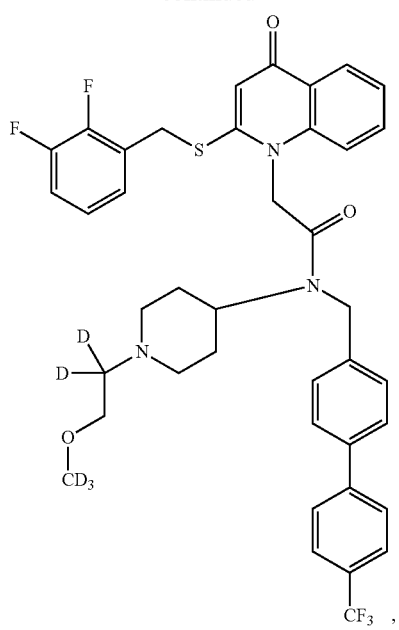
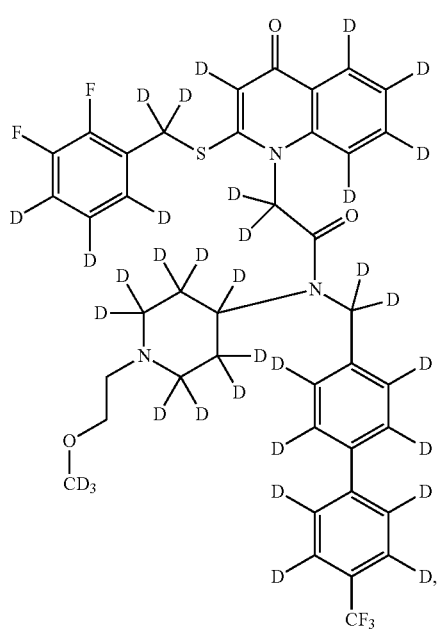
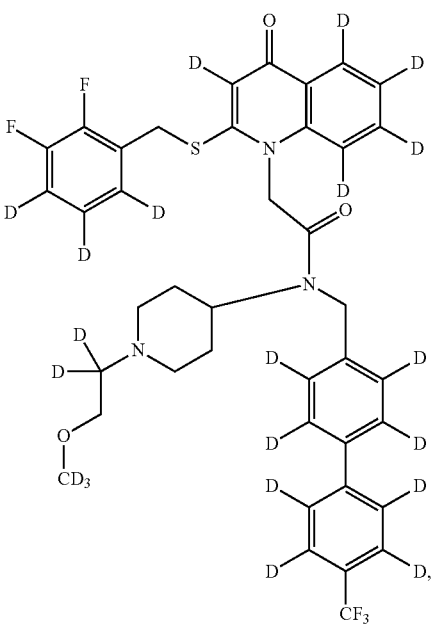

105
-continued
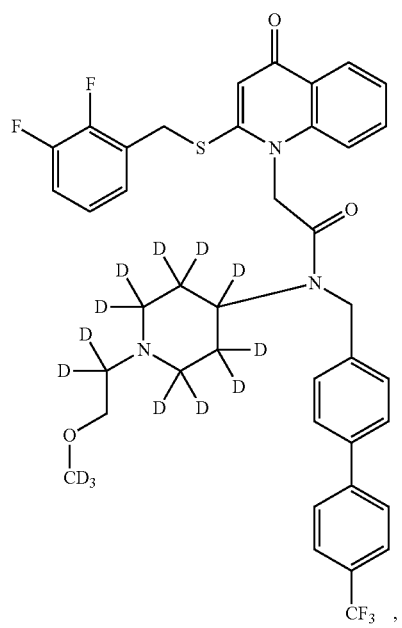
106
-continued
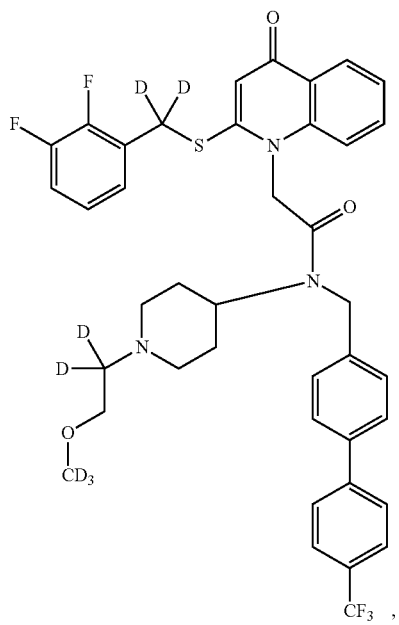
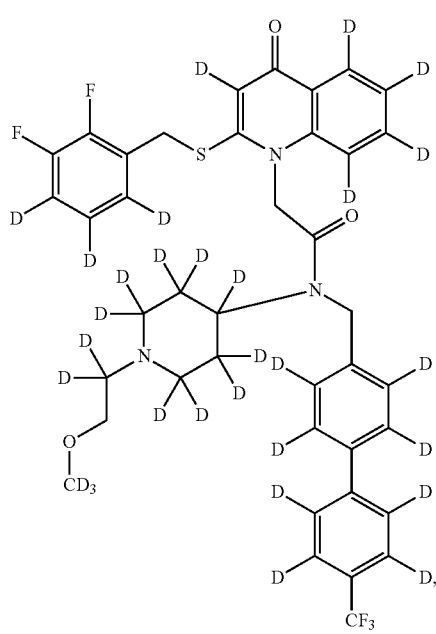
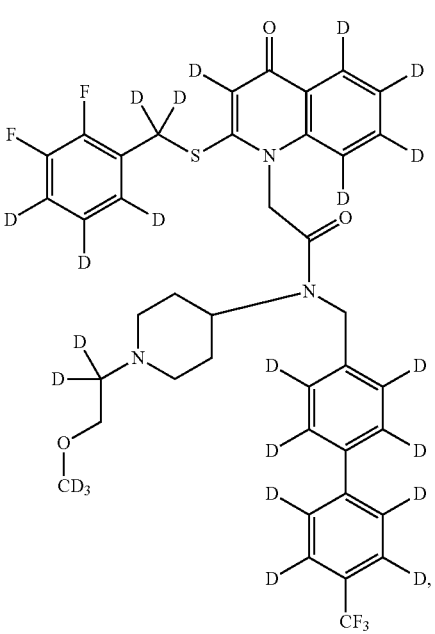

107
-continued
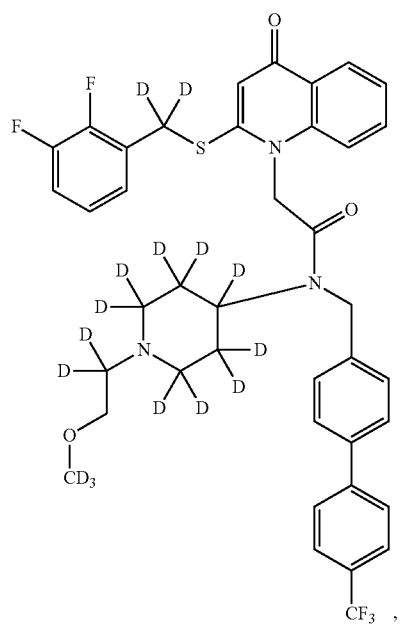
108
-continued
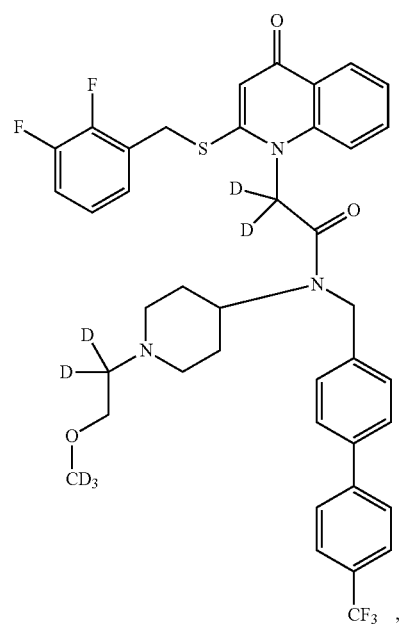
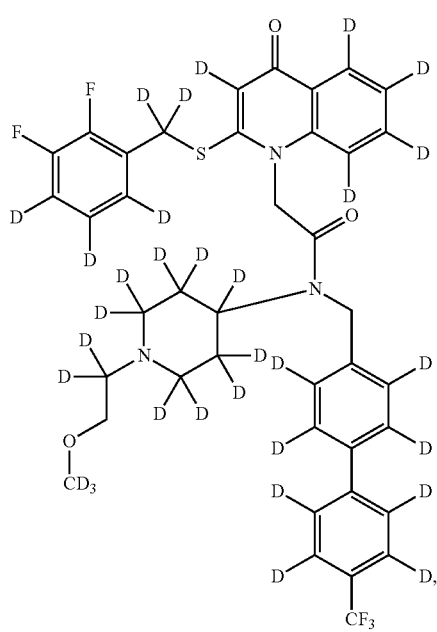
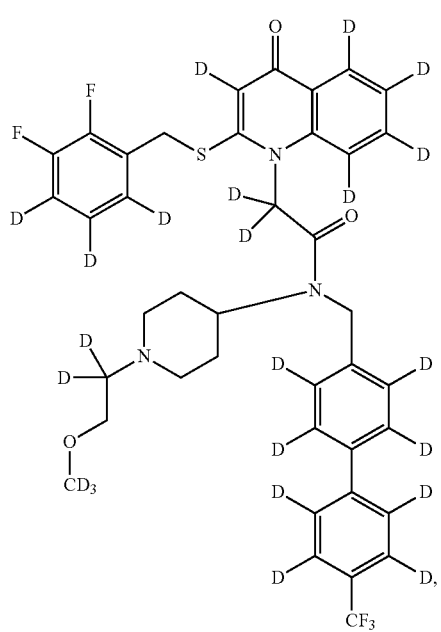

109
-continued
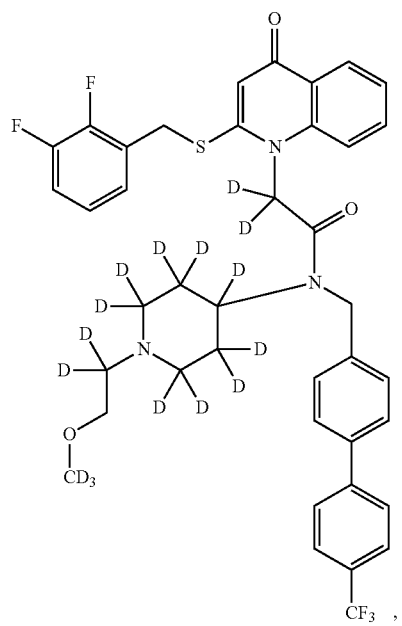
110
-continued
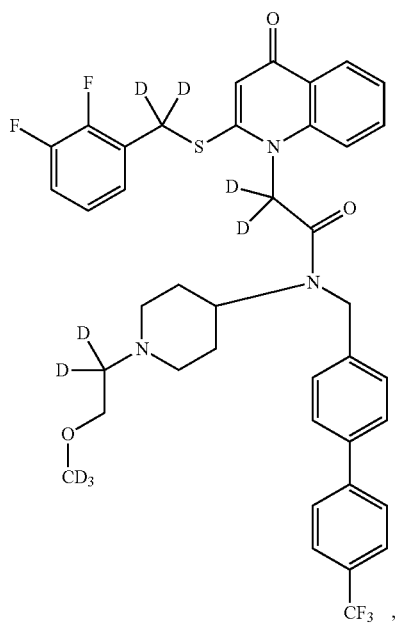
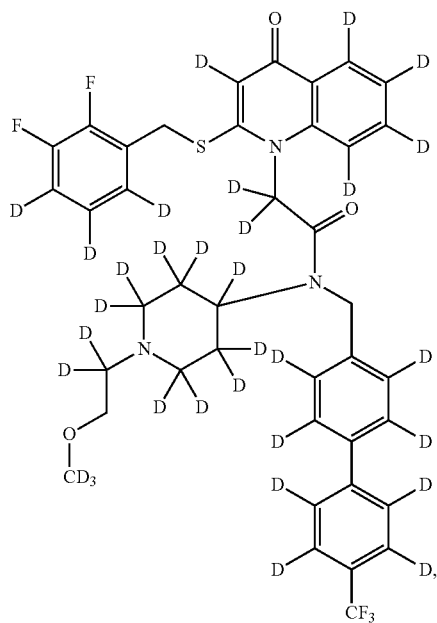
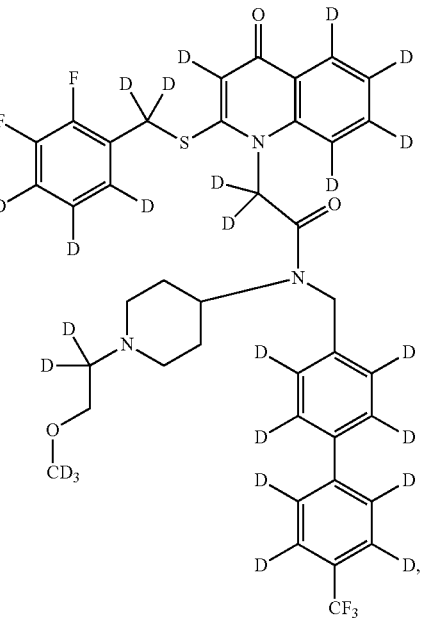

111
-continued
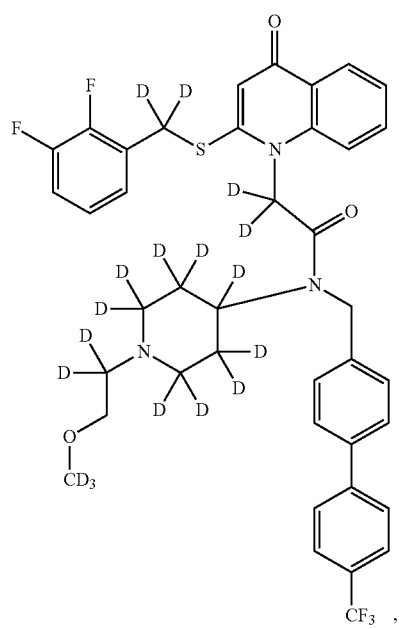
112
-continued
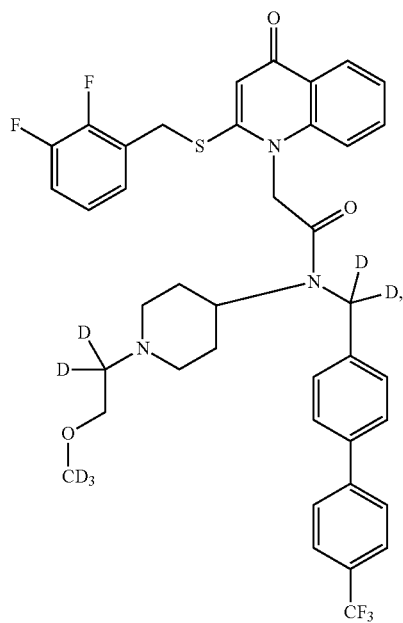
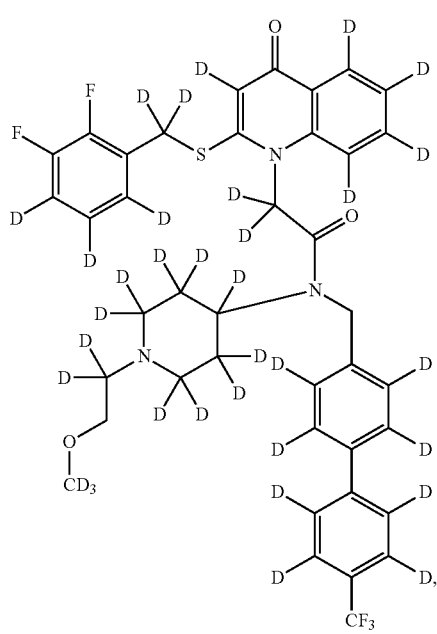,
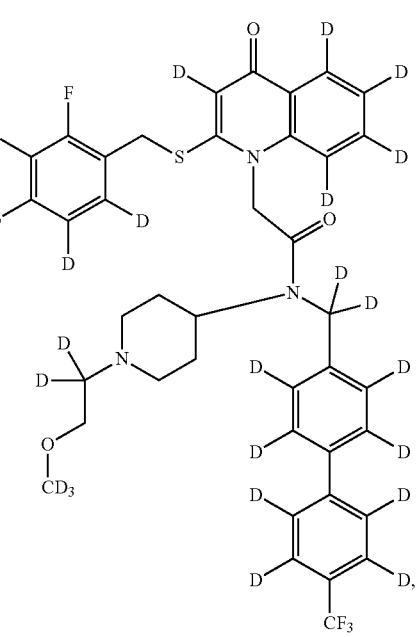

113
-continued
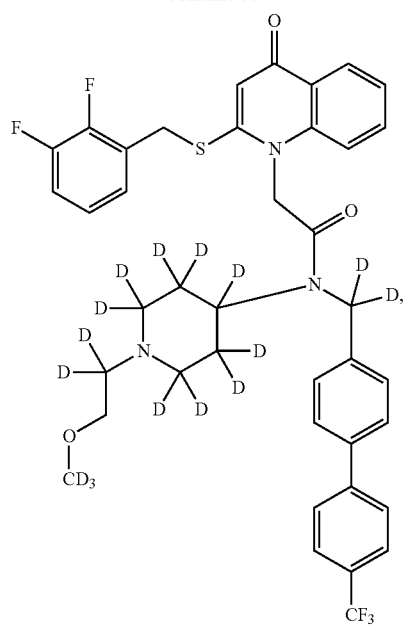
114
-continued
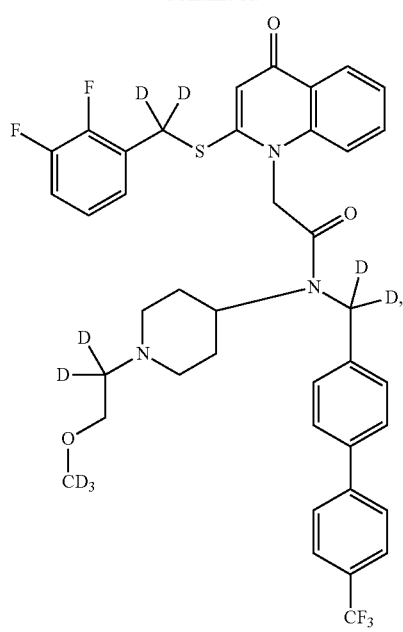
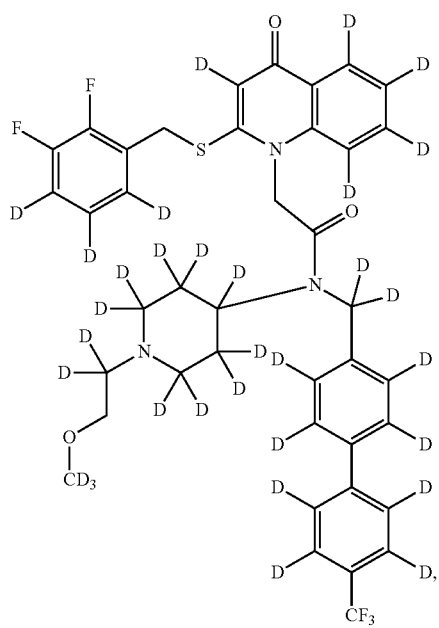
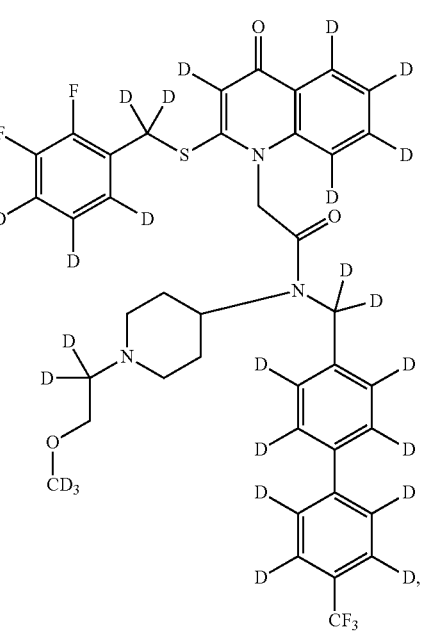

115
-continued
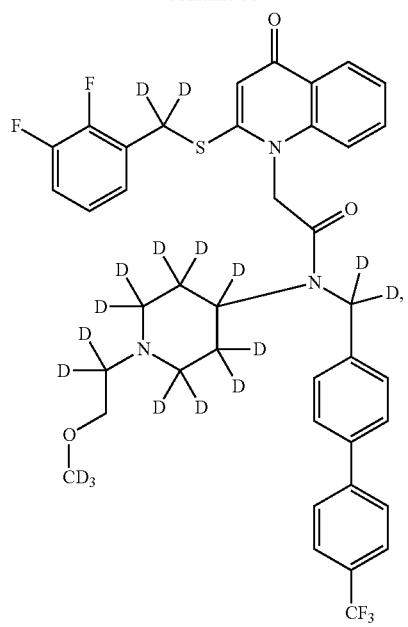
116
-continued
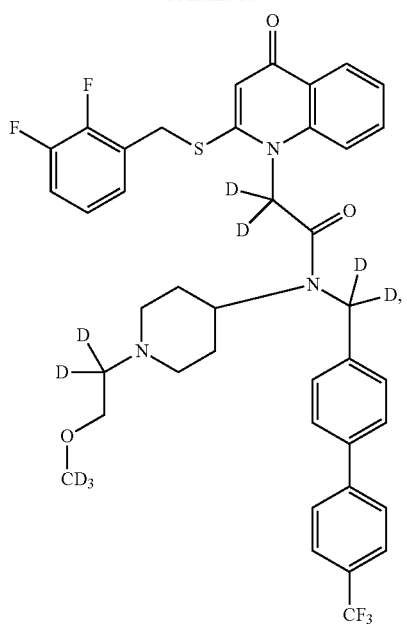
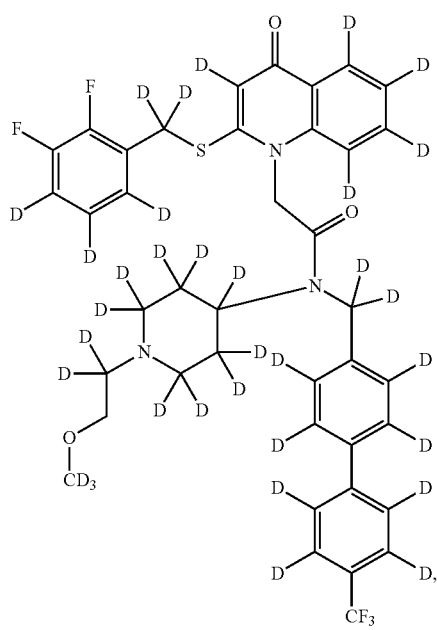
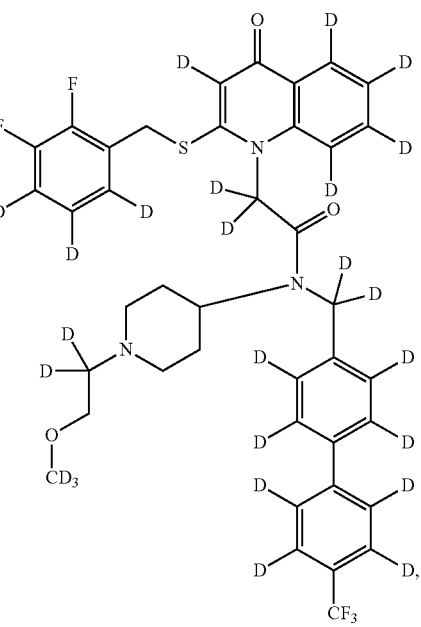

117
-continued
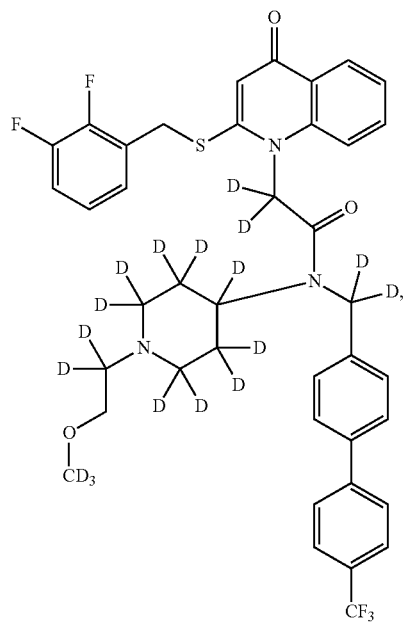
118
-continued
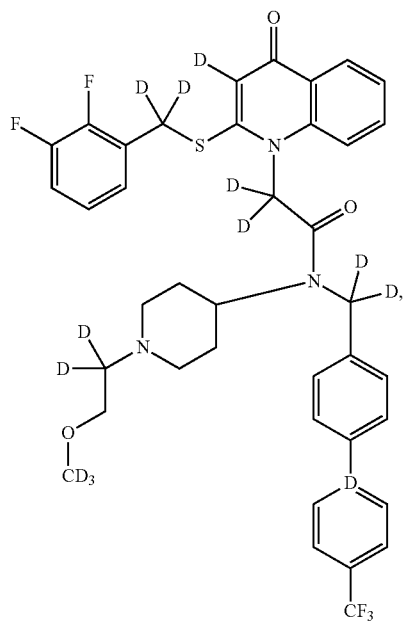
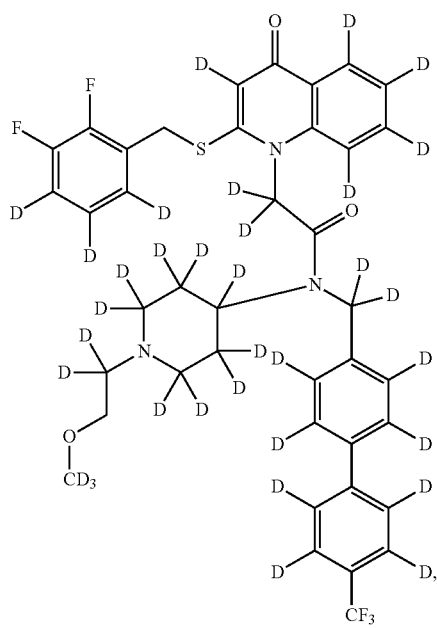
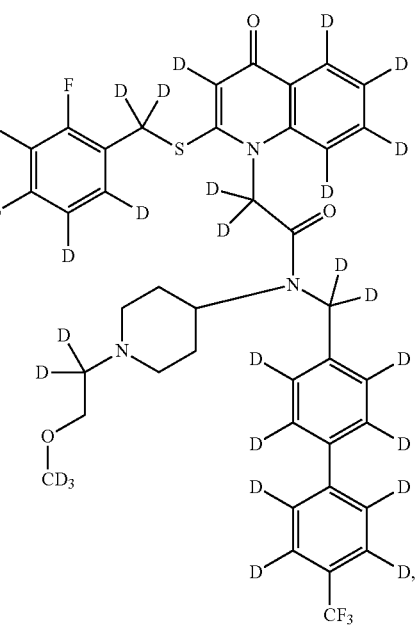

119
-continued
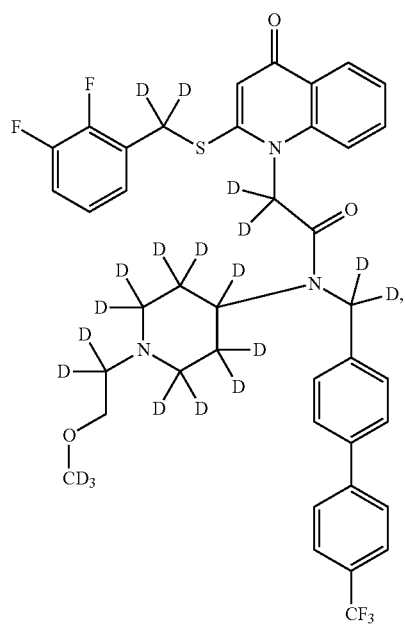
120
-continued
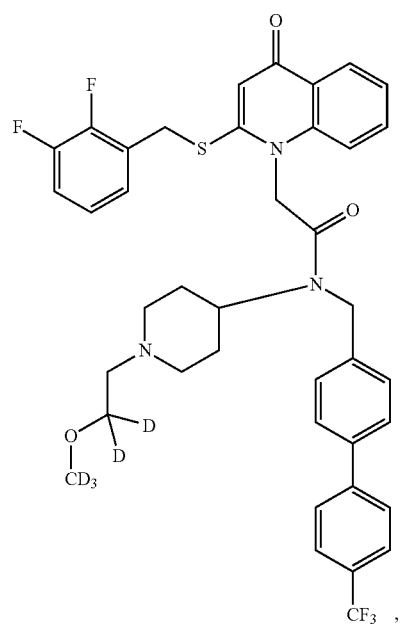

121
-continued
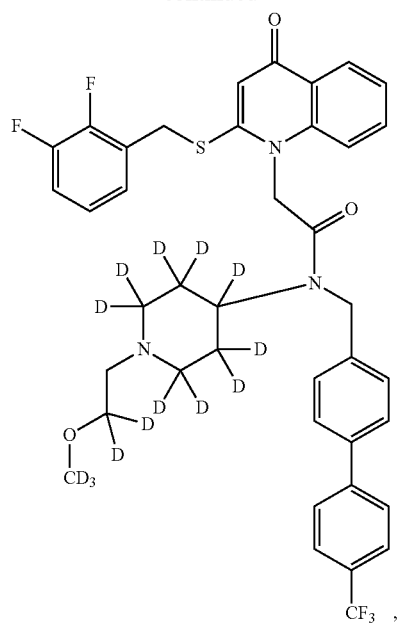
122
-continued
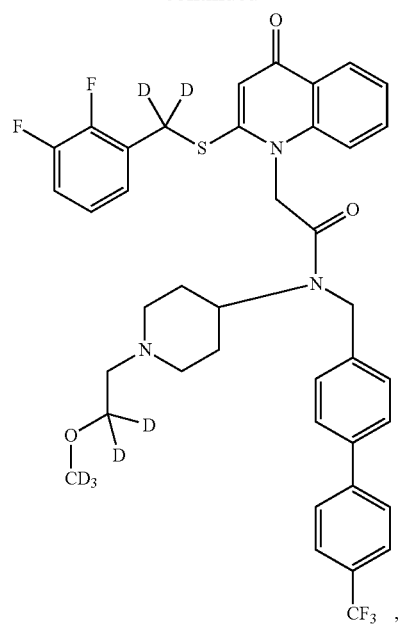
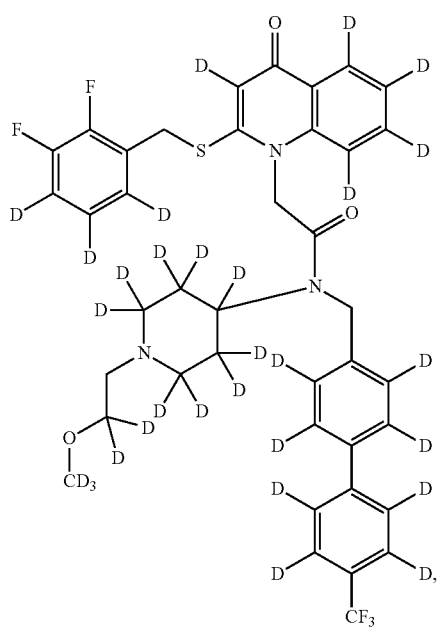
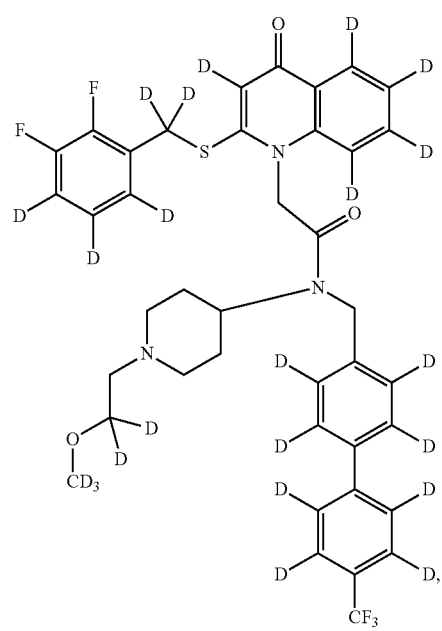

123
-continued
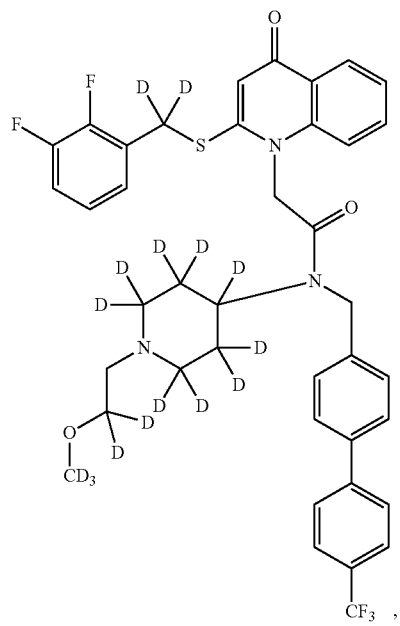
124
-continued
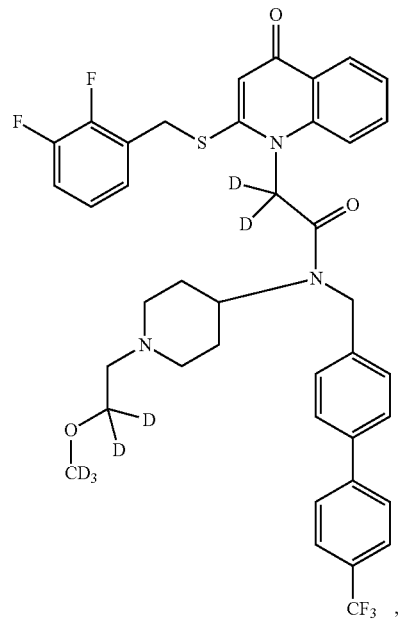
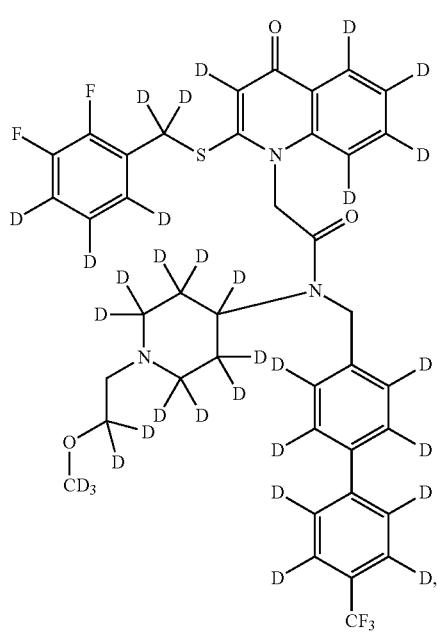
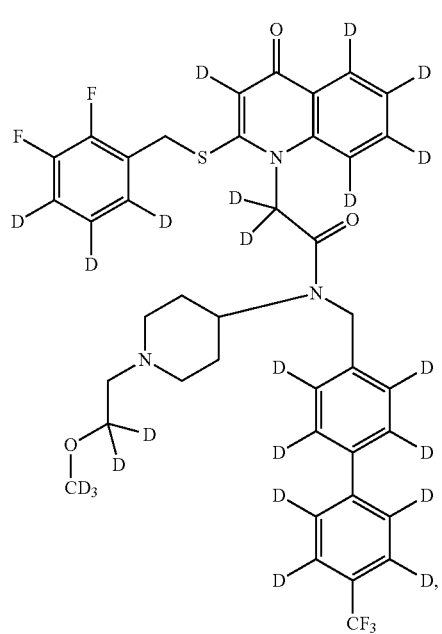

125
-continued
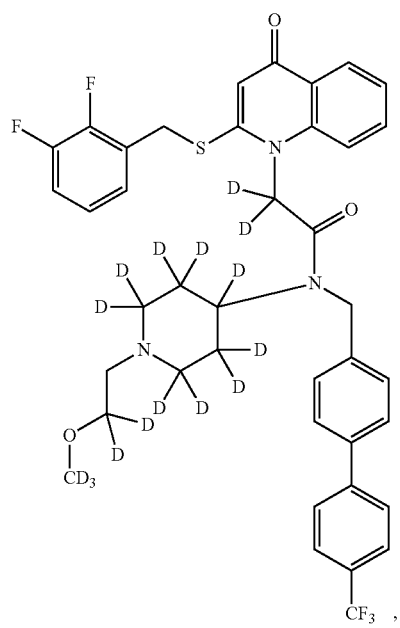
126
-continued
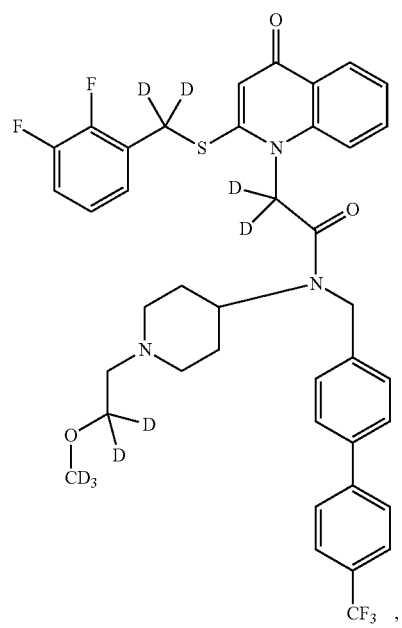
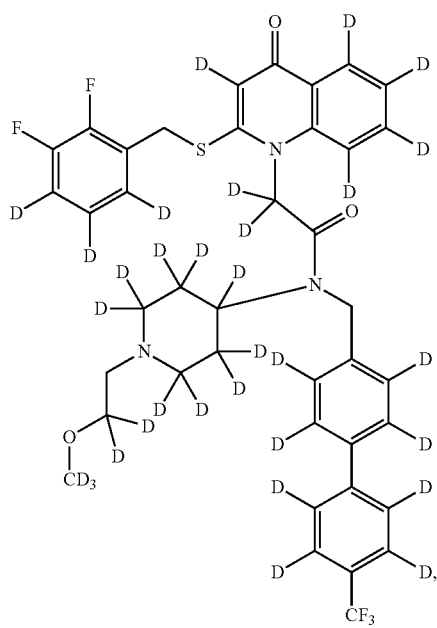
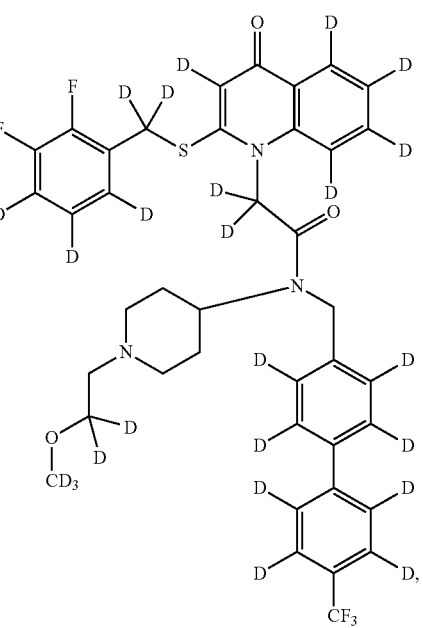

127
-continued
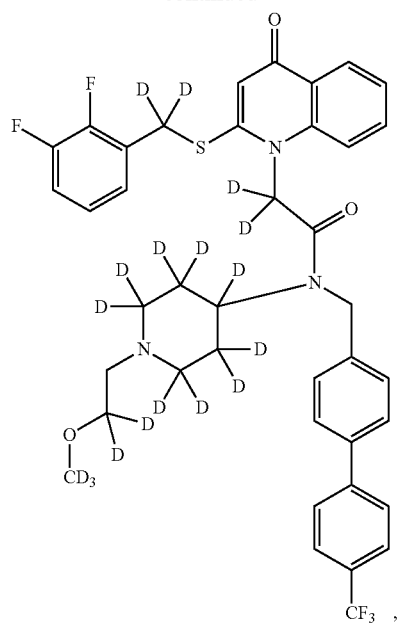
128
-continued
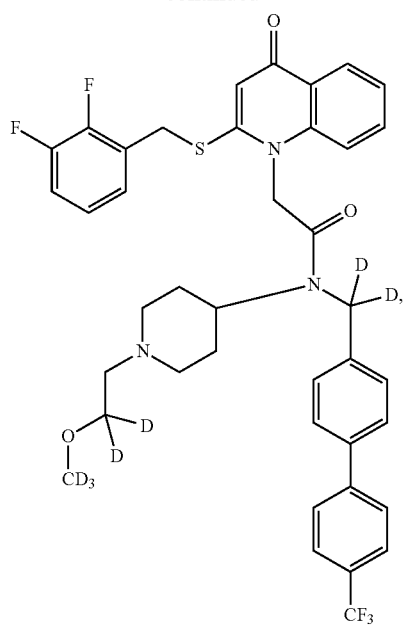
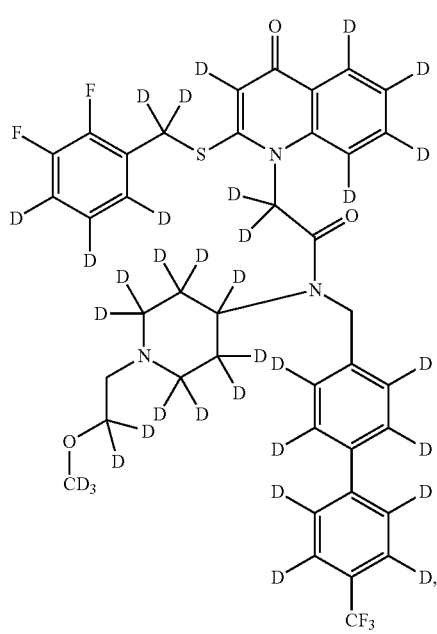
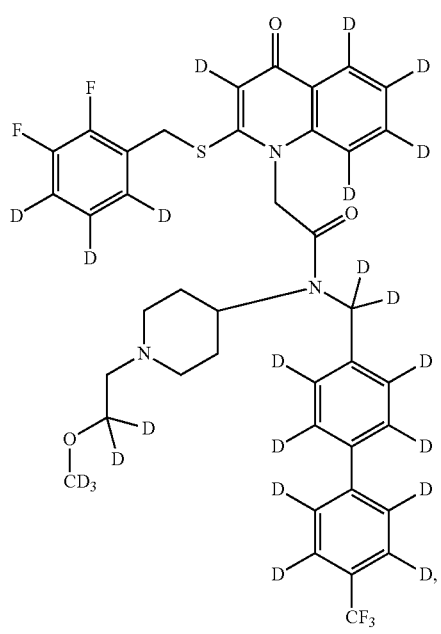

129
-continued
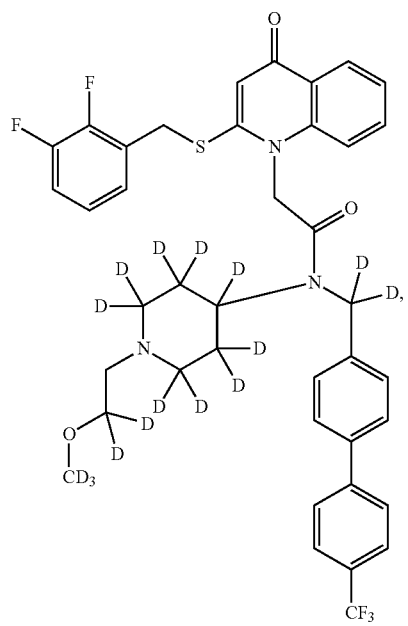
130
-continued
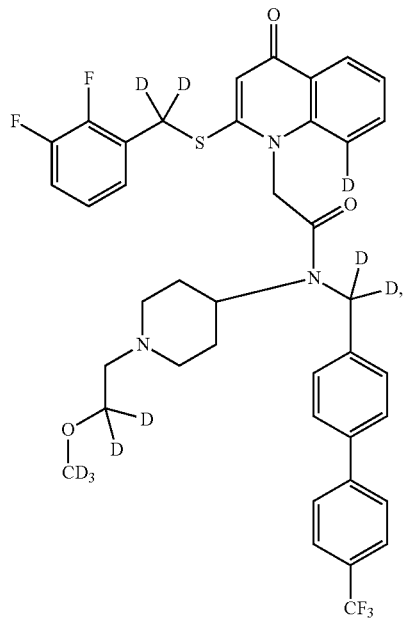
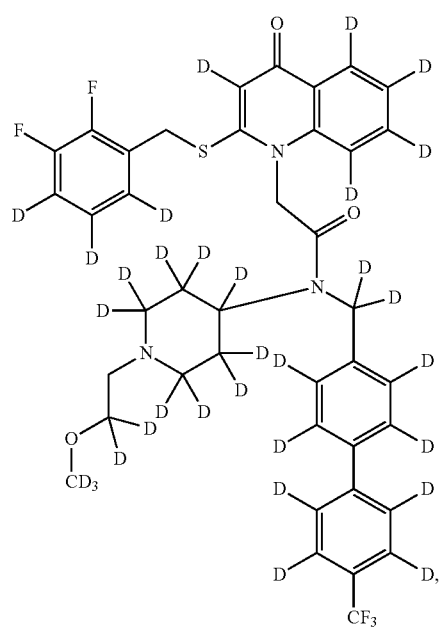
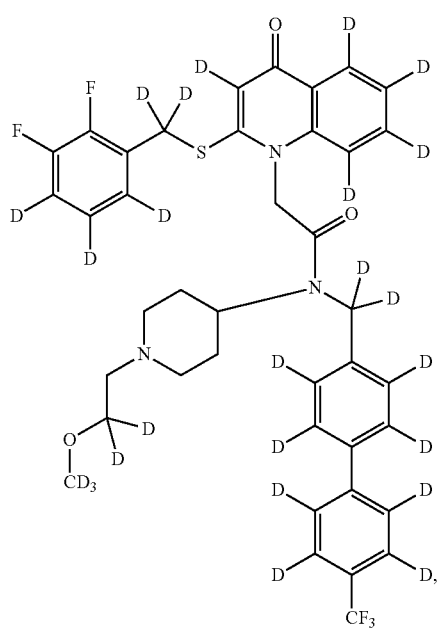

131
-continued
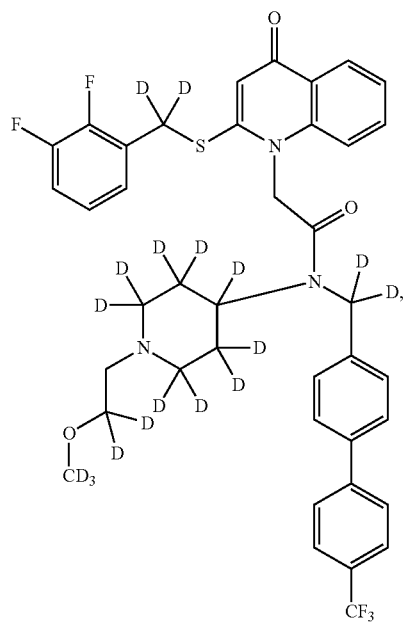
132
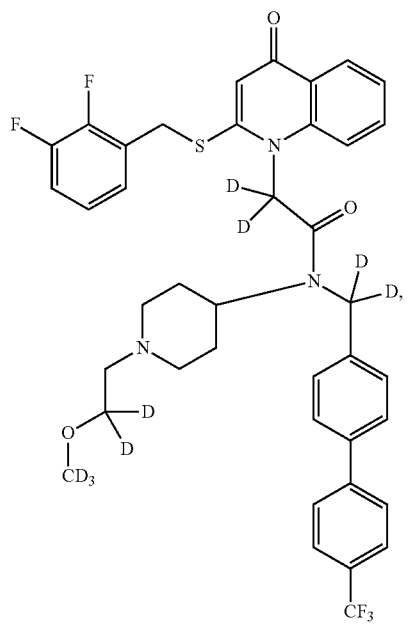
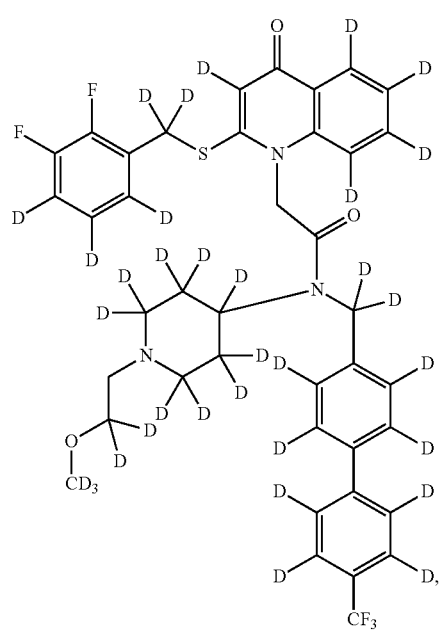
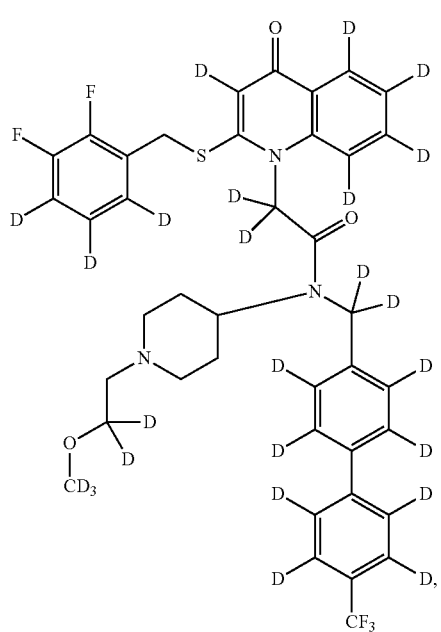

133
-continued
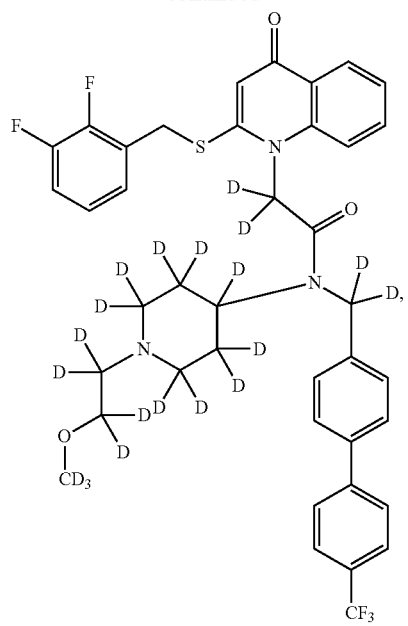
134
-continued
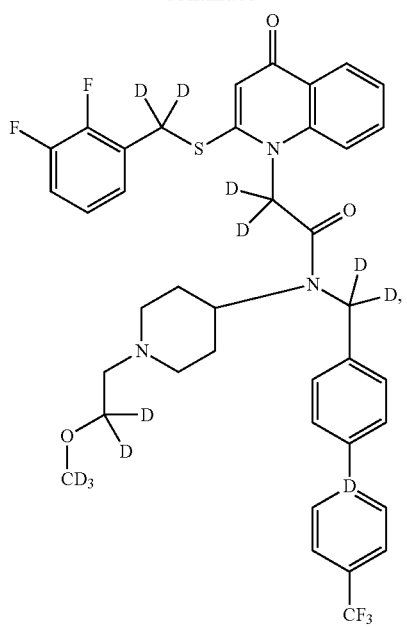
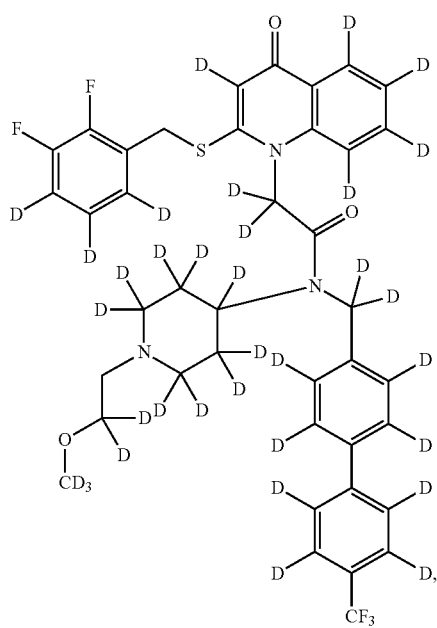
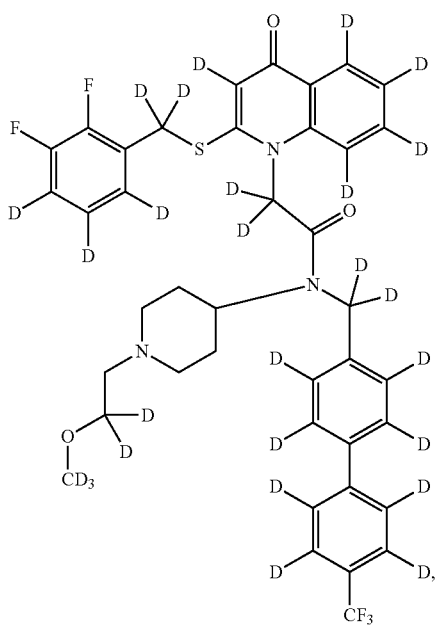

135
-continued
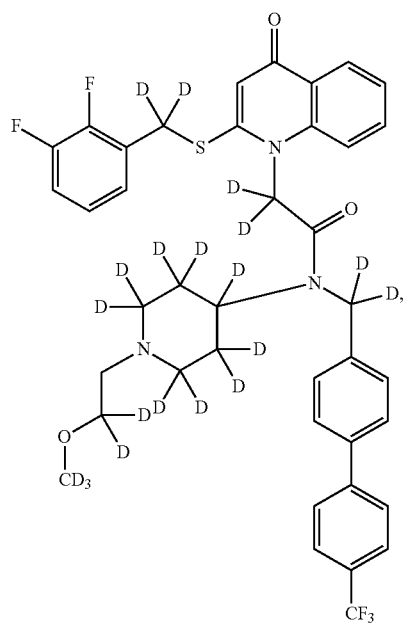
136
-continued
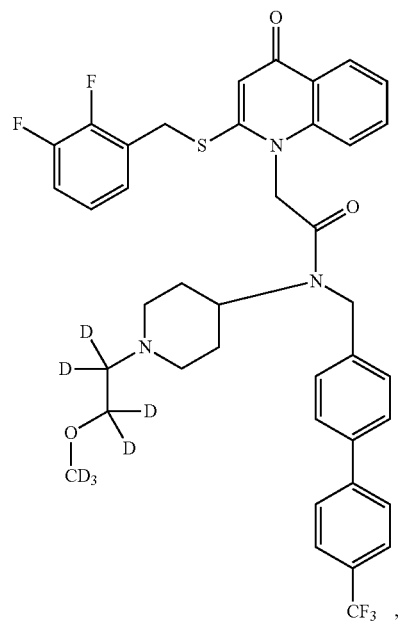
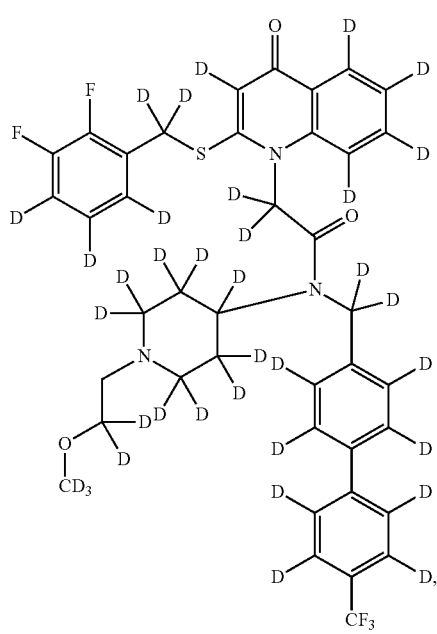
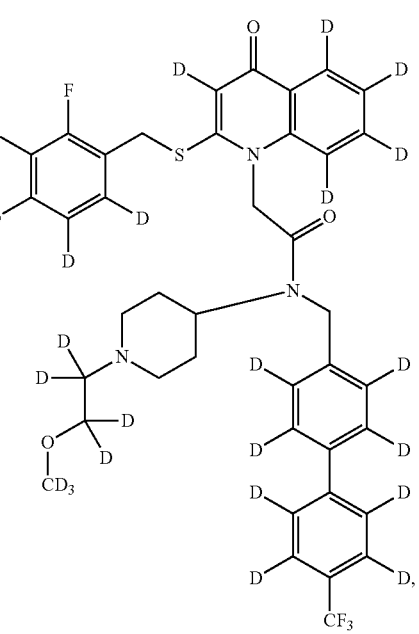

137
-continued
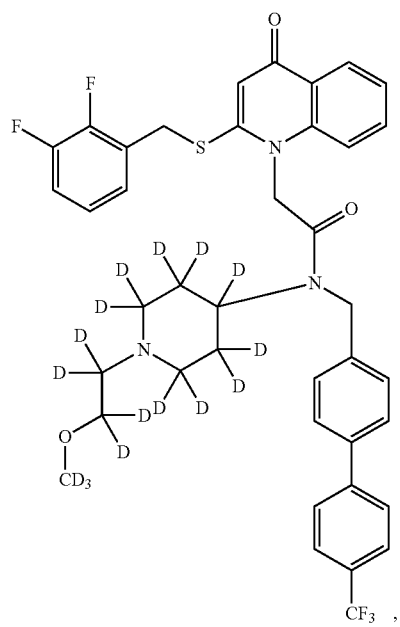
138
-continued
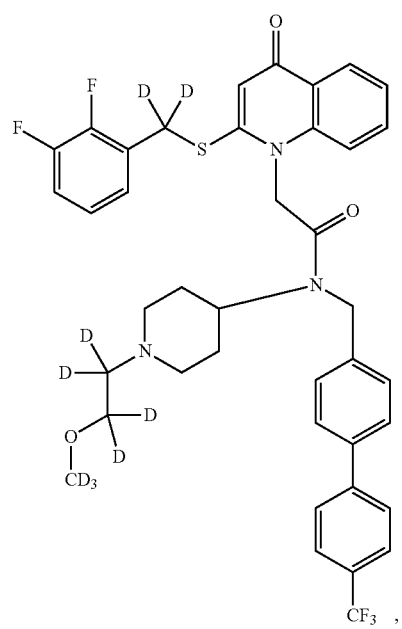
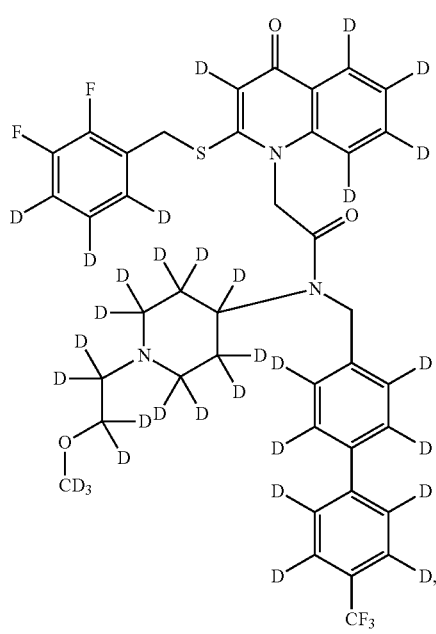
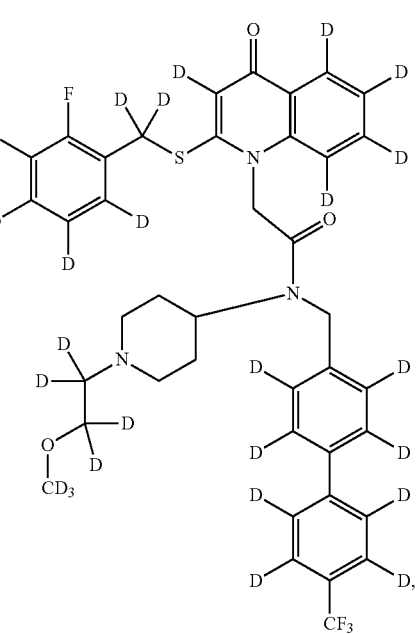

139
-continued
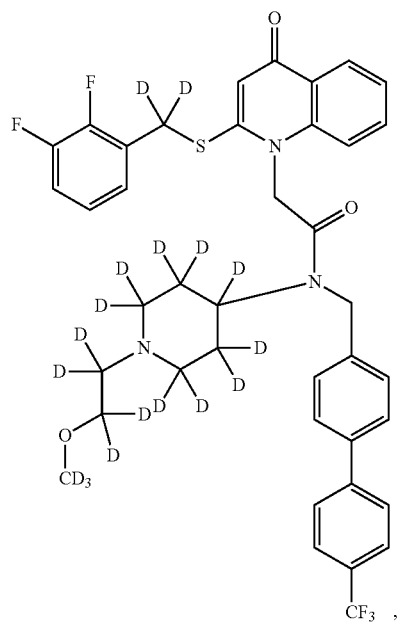
140
-continued
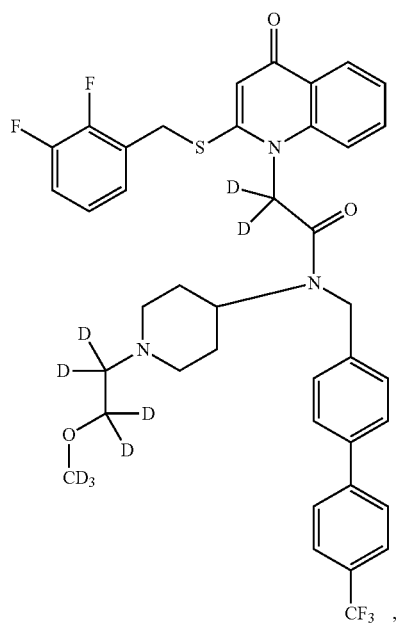
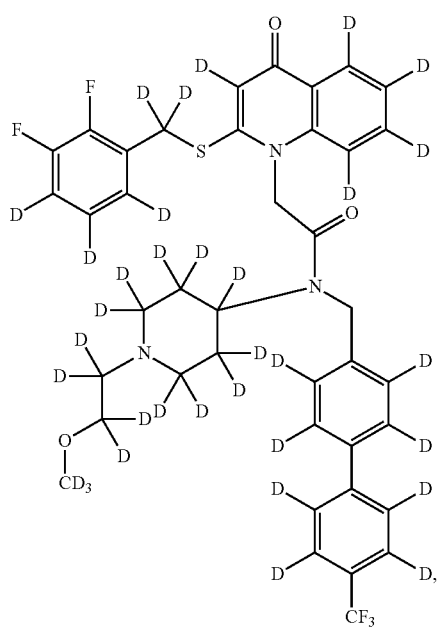
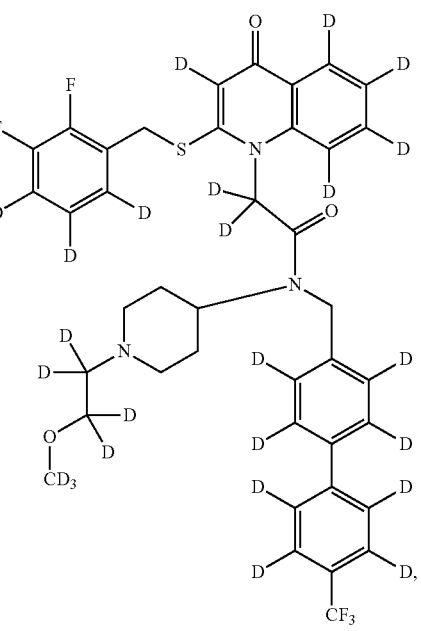

141
-continued
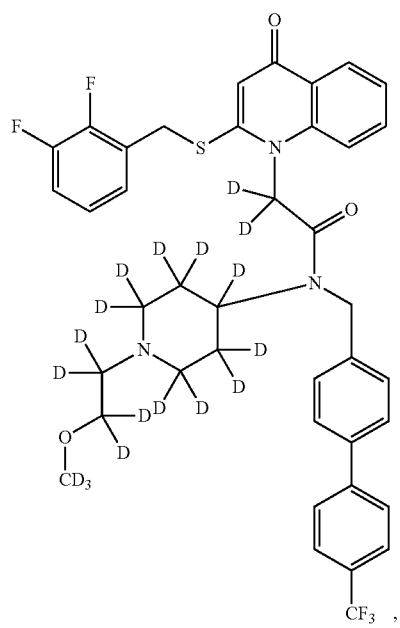
142
-continued
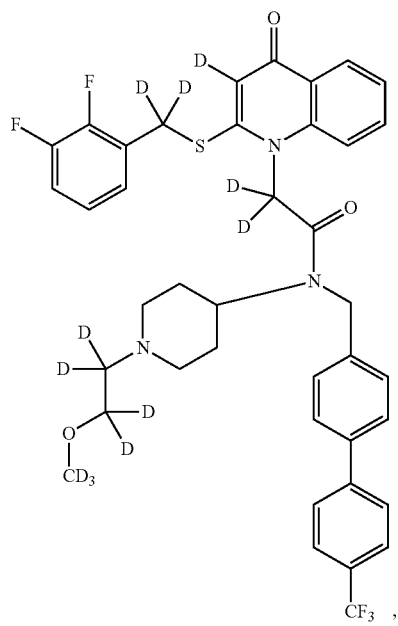
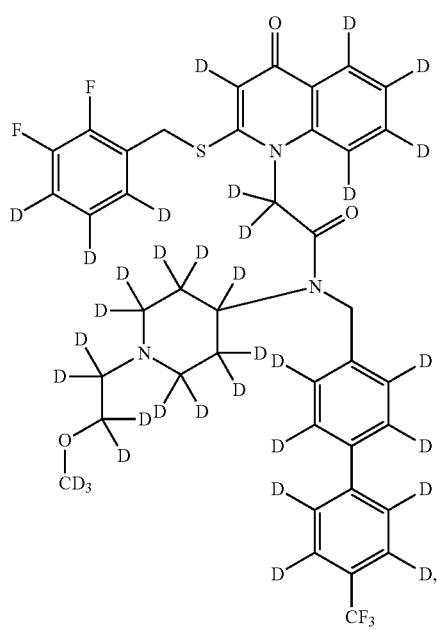
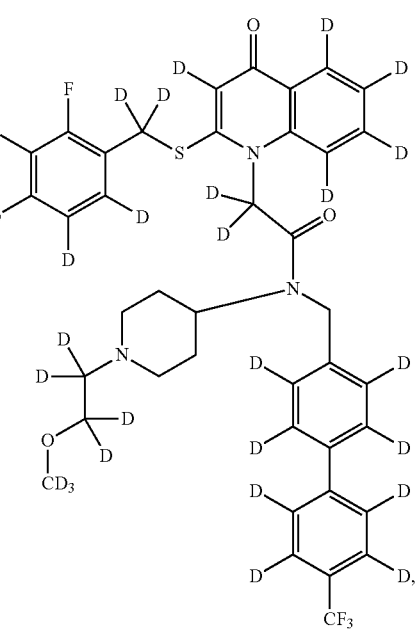

143
-continued
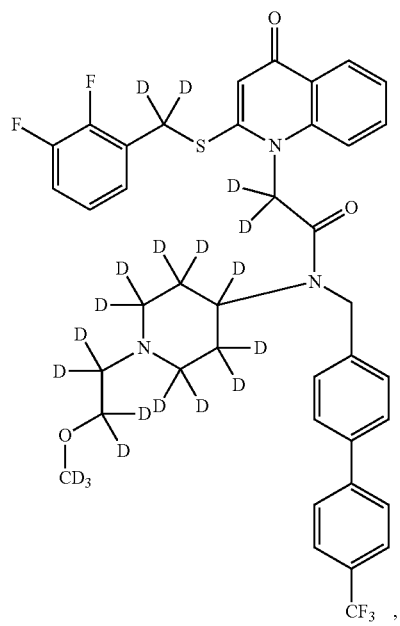
144
-continued
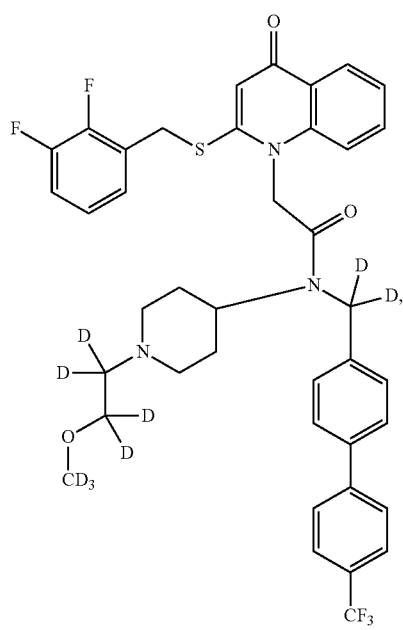
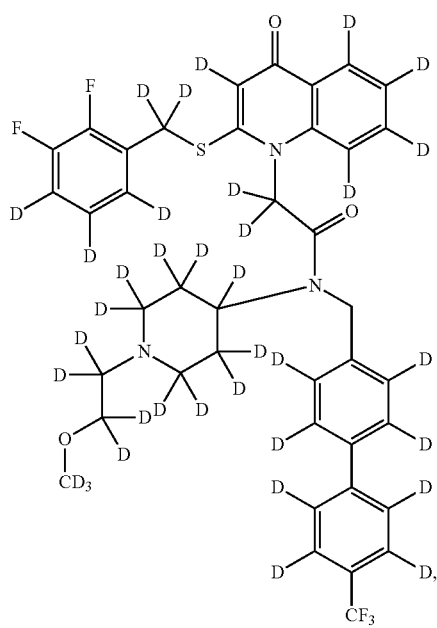
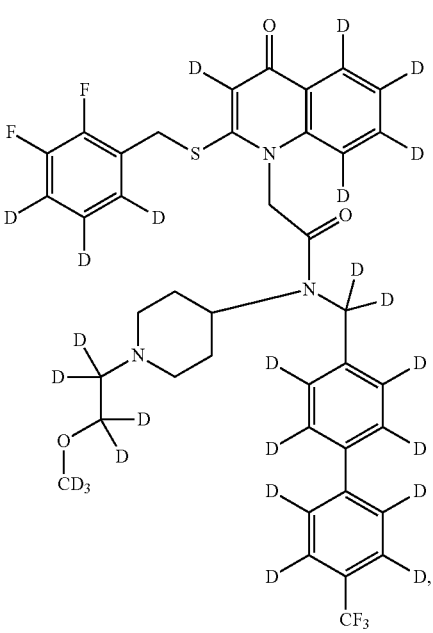

145
-continued
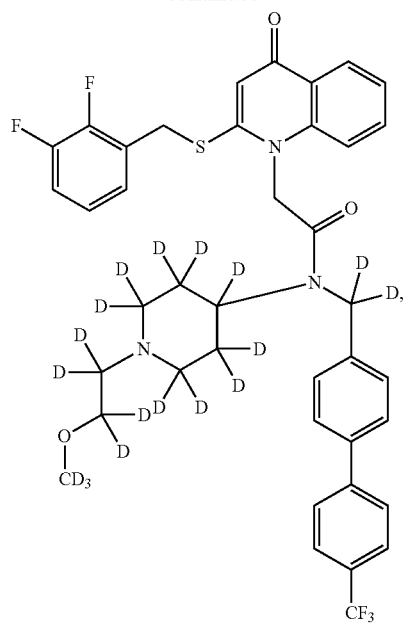
146
-continued
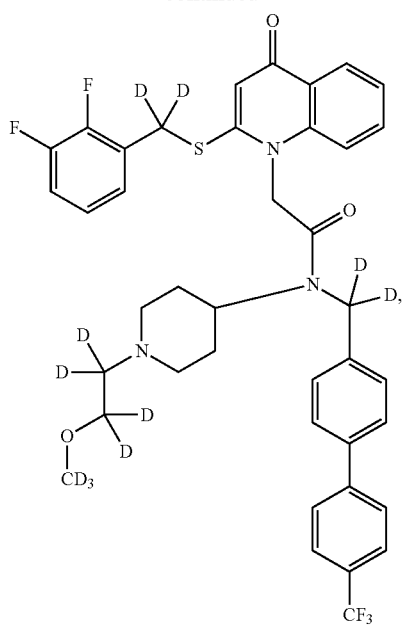
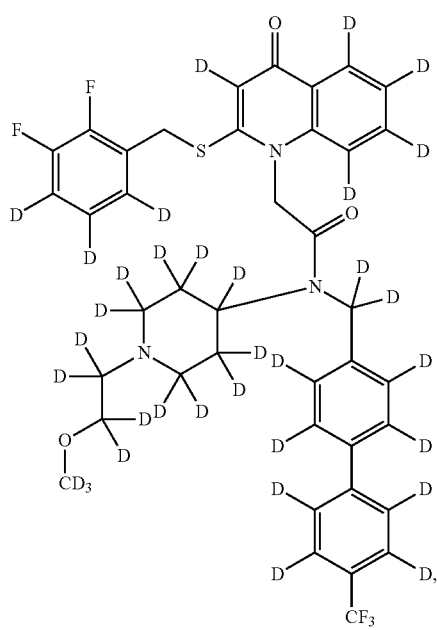
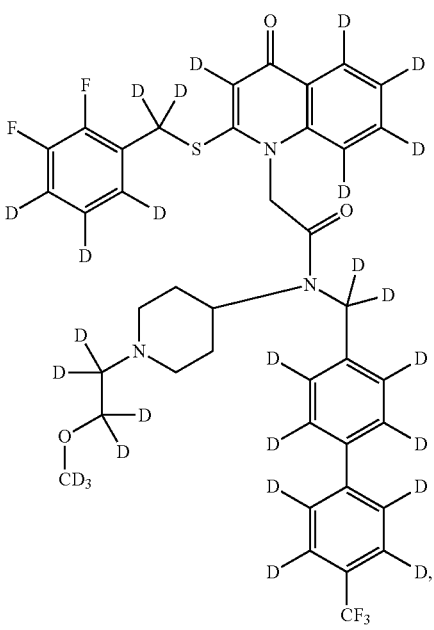

147
-continued
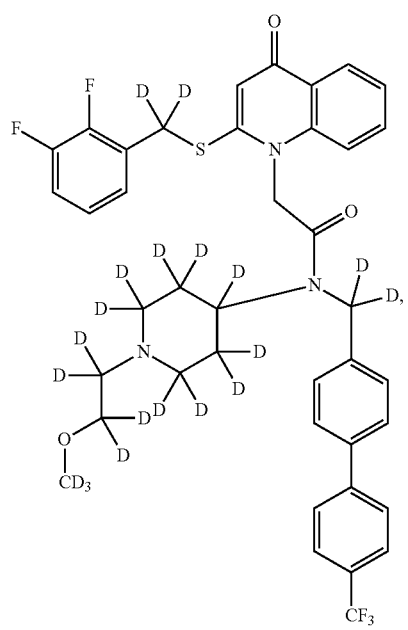
148
-continued
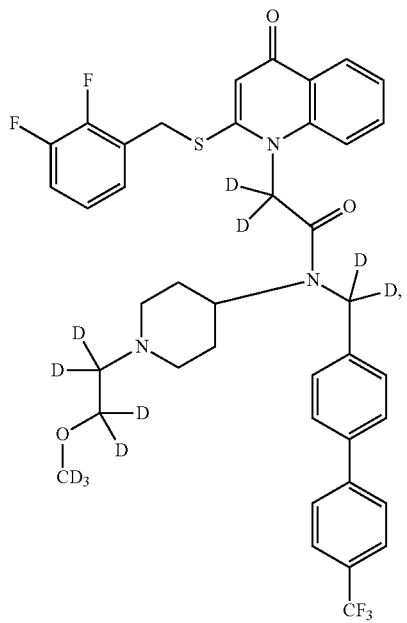
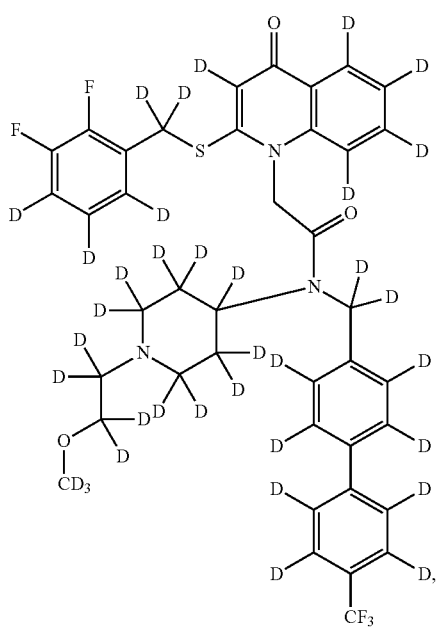
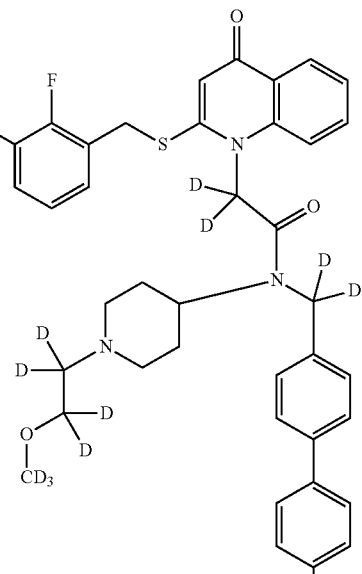

149
-continued
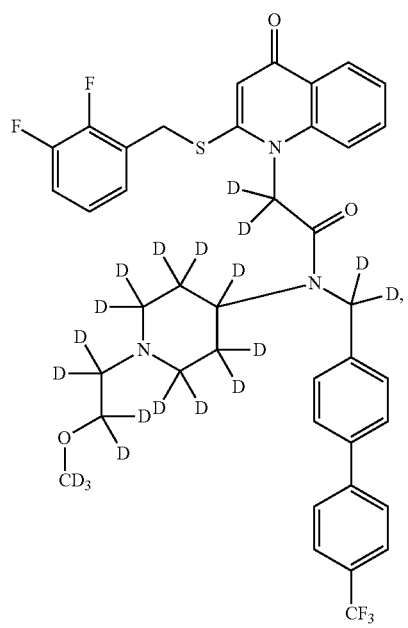
150
-continued
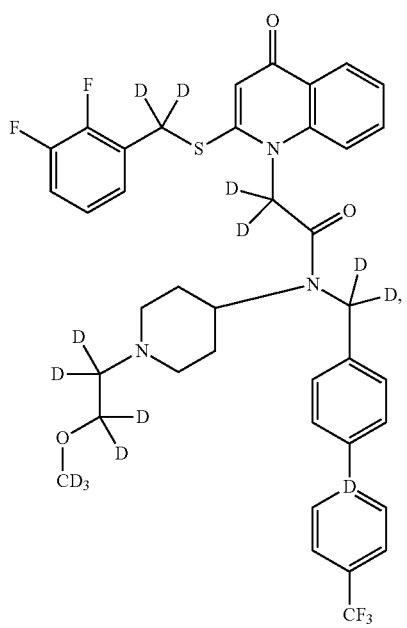
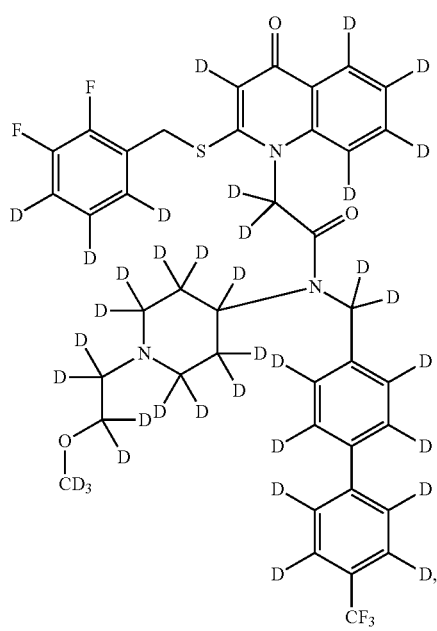
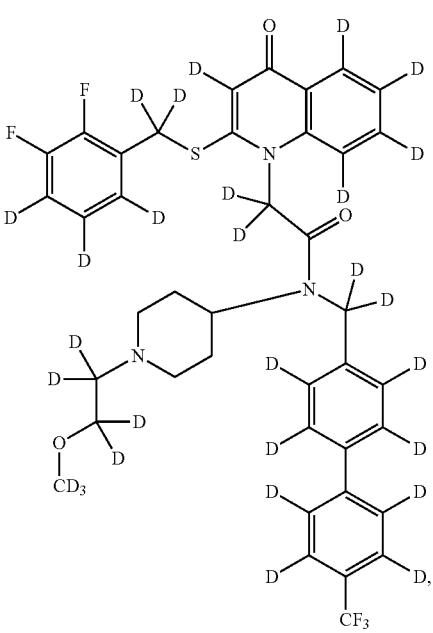

151
-continued
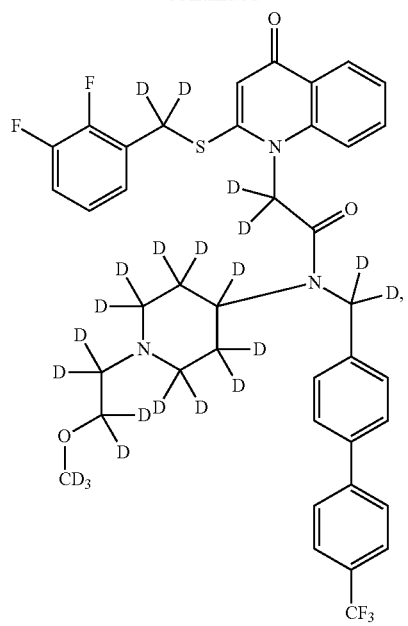
152
-continued
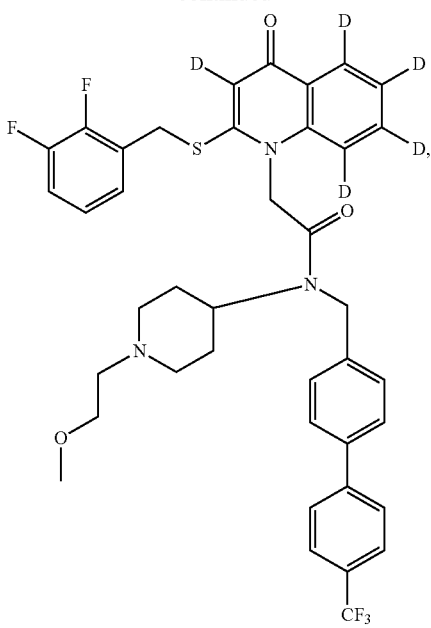
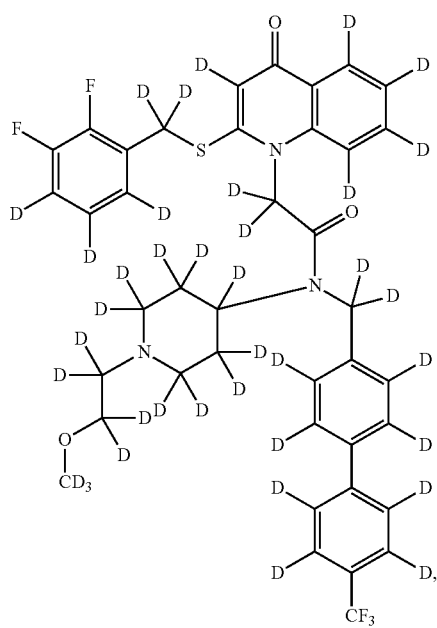
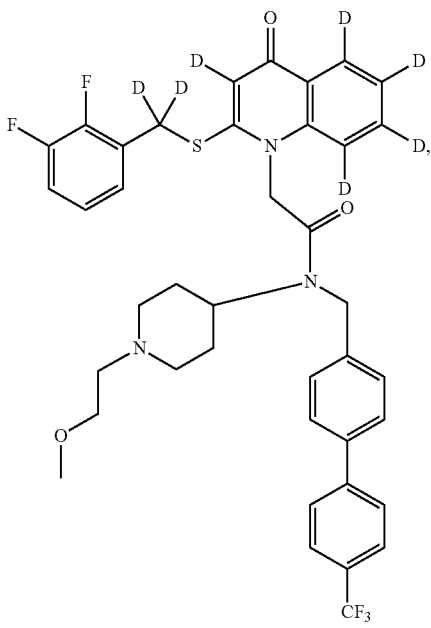

153
-continued
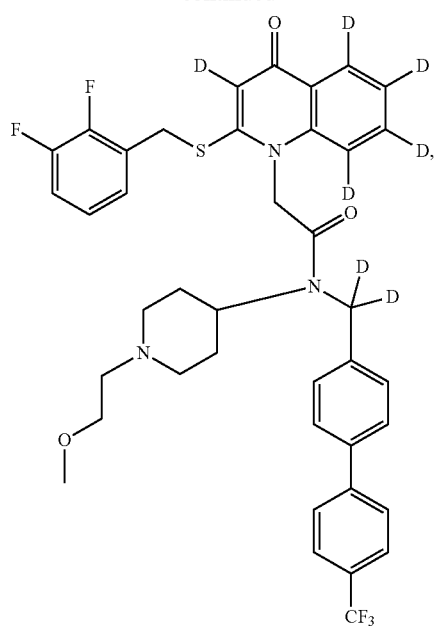
154
-continued
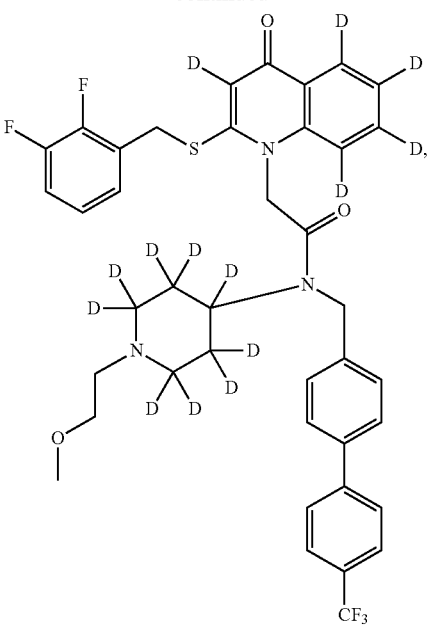
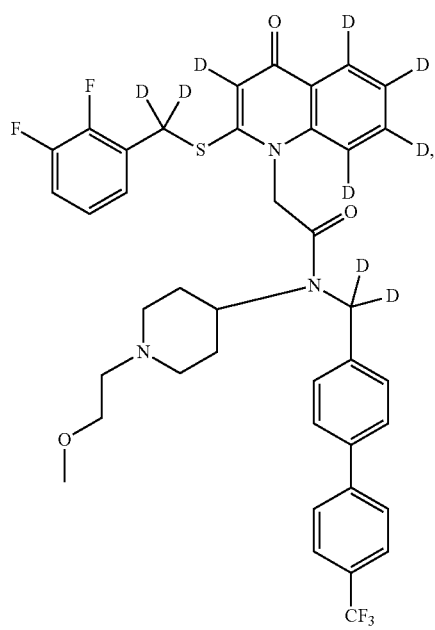
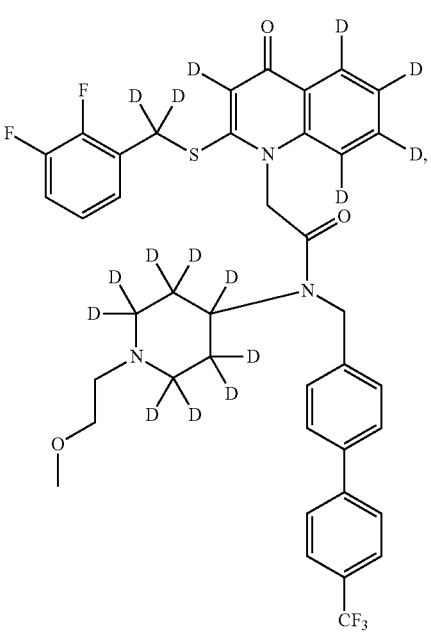

155
-continued
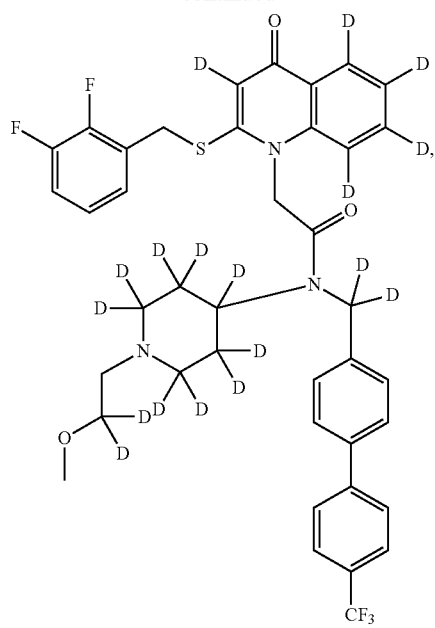
156
-continued
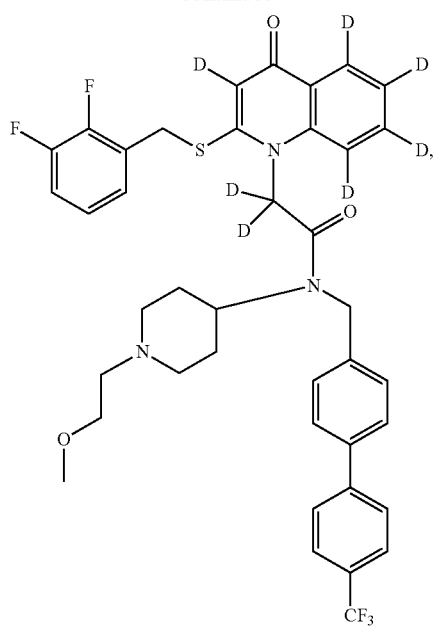
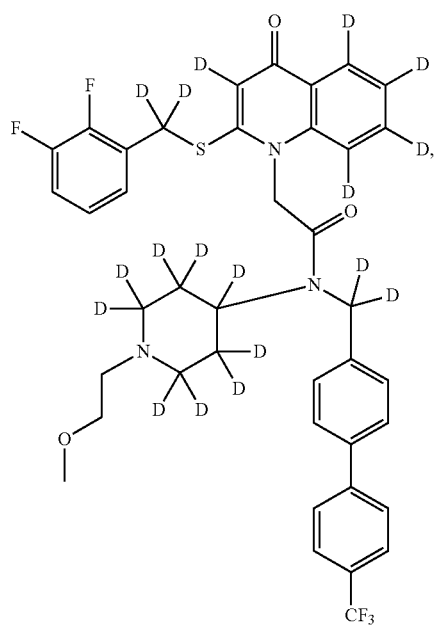

157
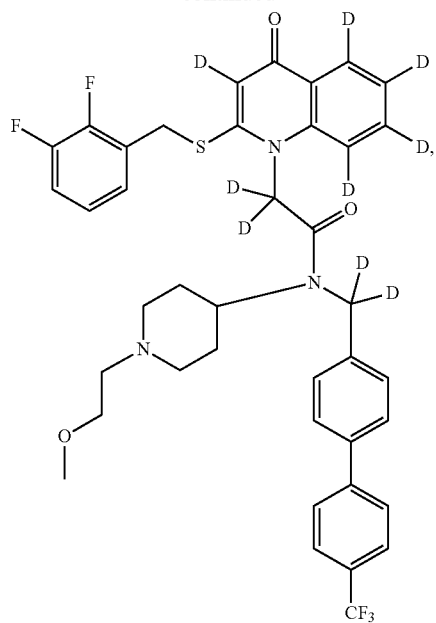
158
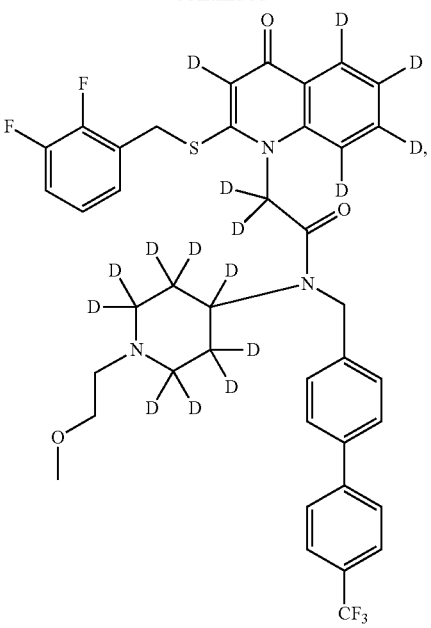

159
-continued
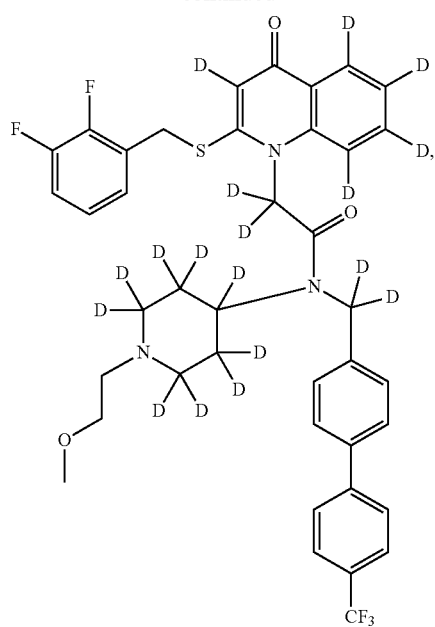
160
-continued
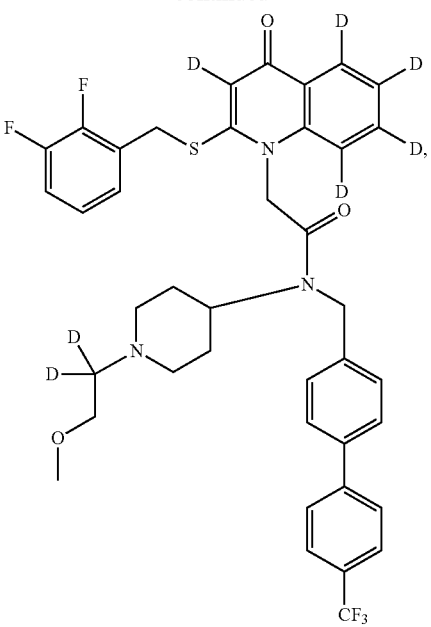
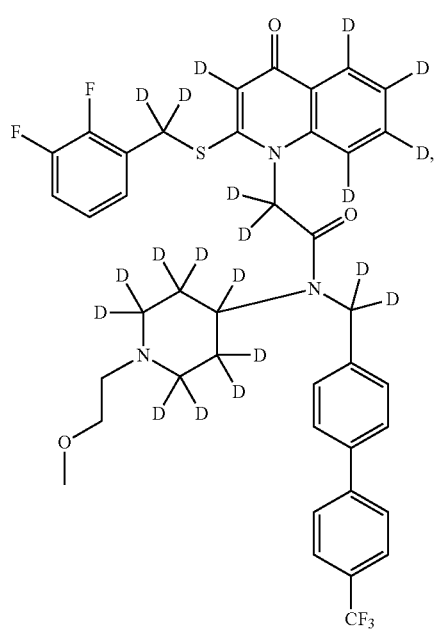
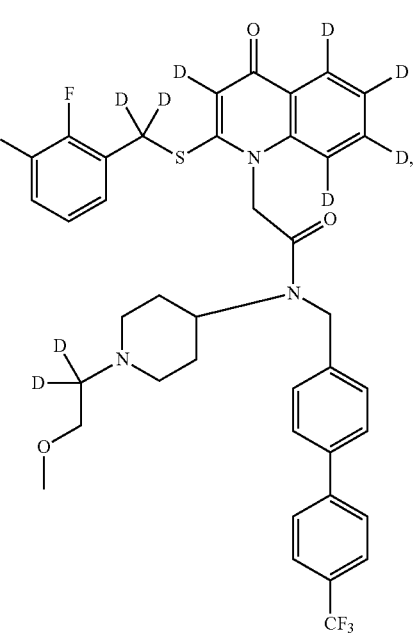

161
-continued
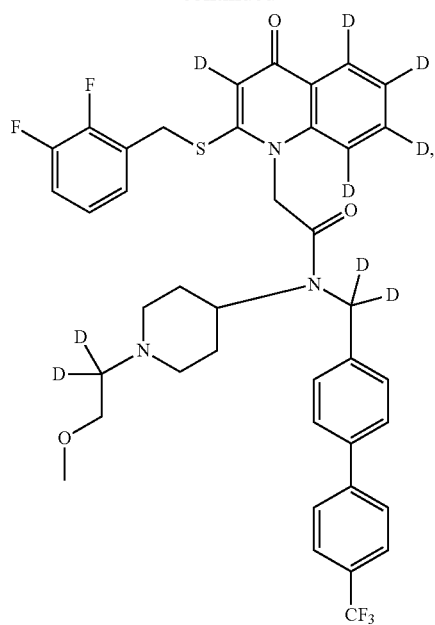
162
-continued
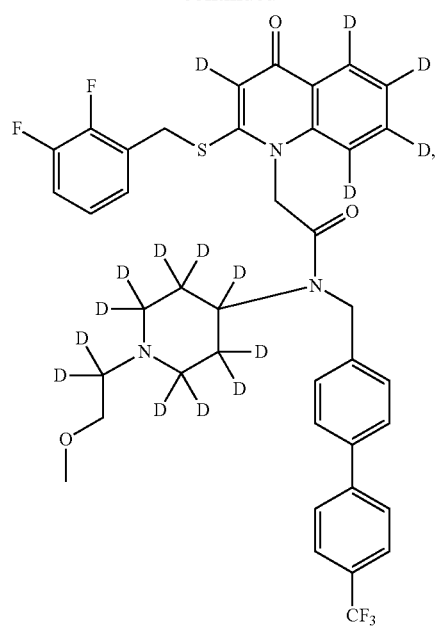
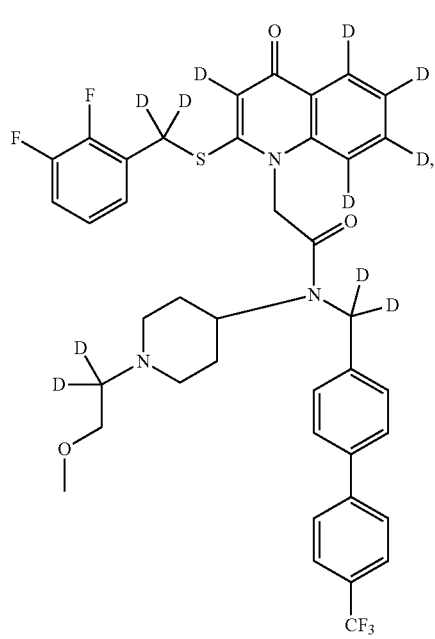
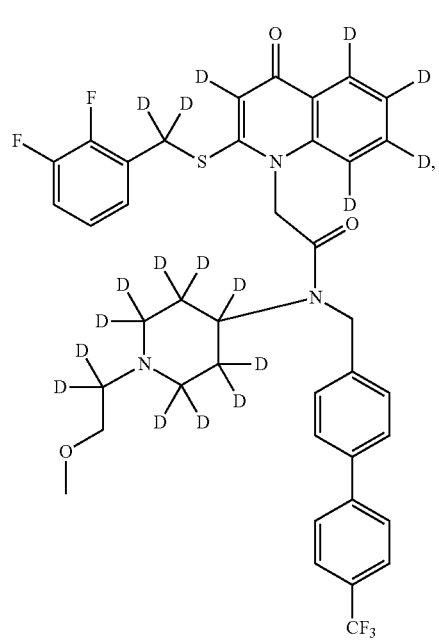

163
-continued
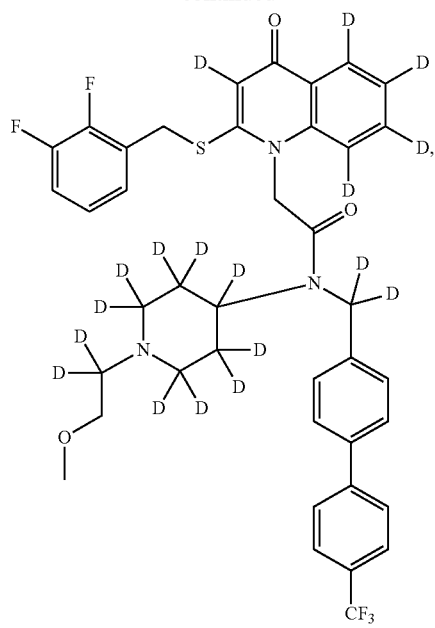
164
-continued
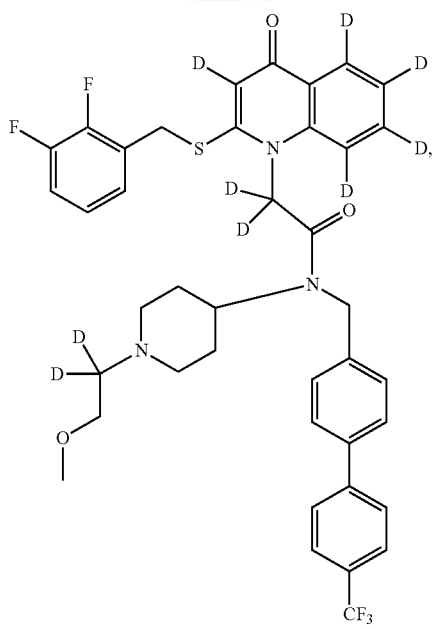

165
-continued
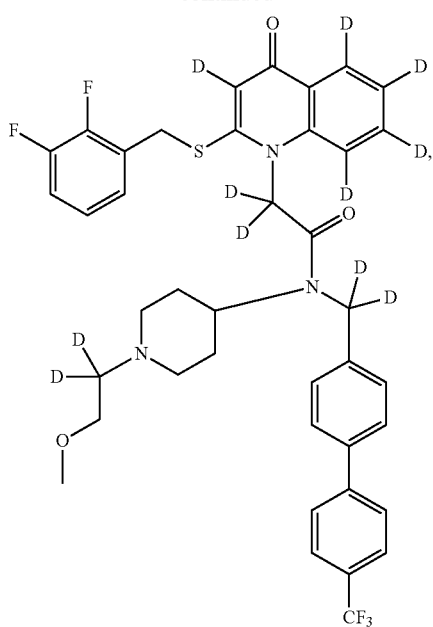
166
-continued
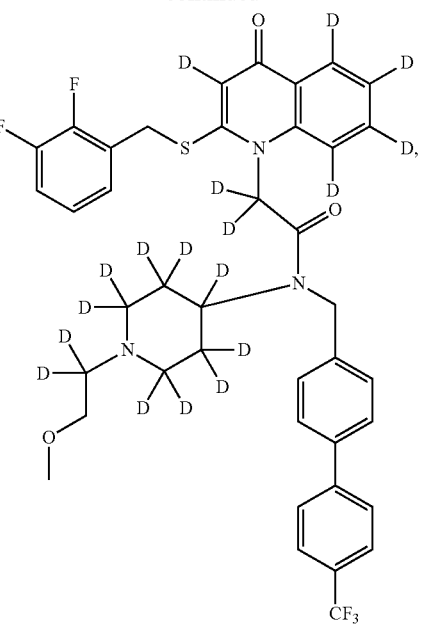
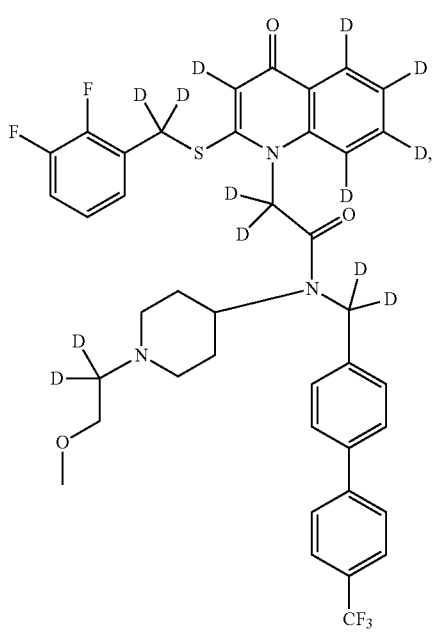

167
-continued
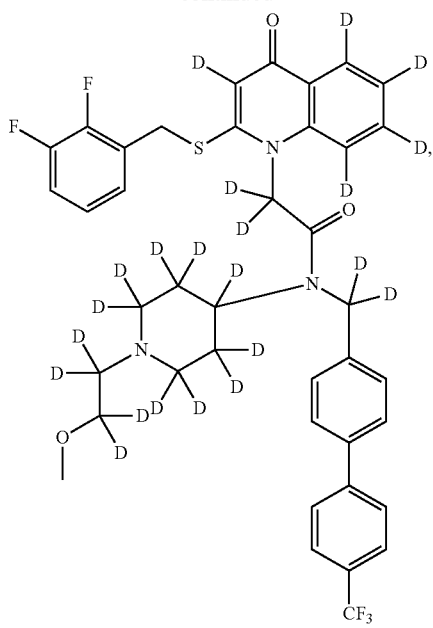
168
-continued
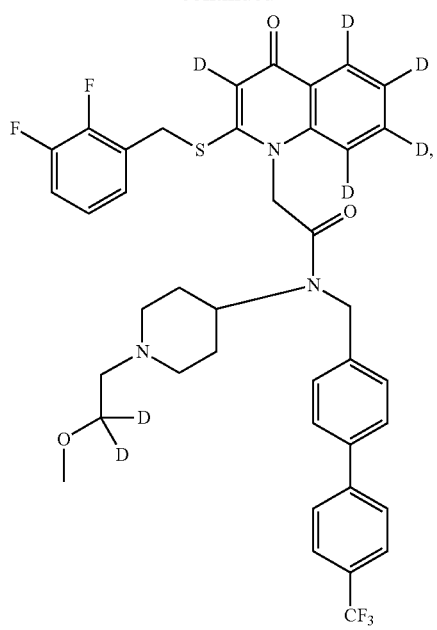
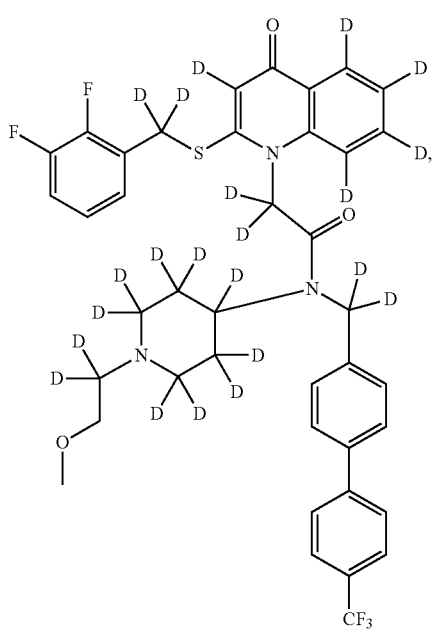
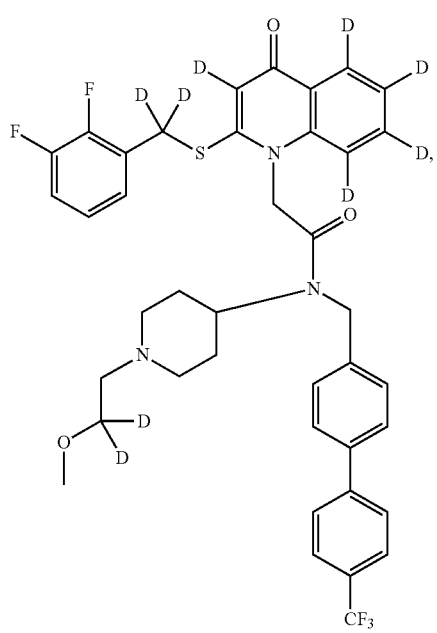

169
-continued
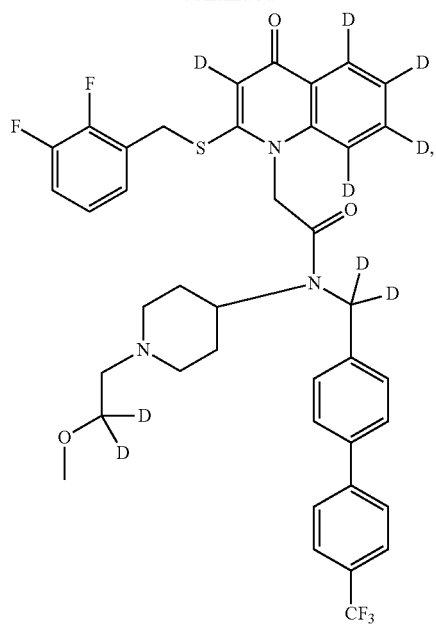
170
-continued
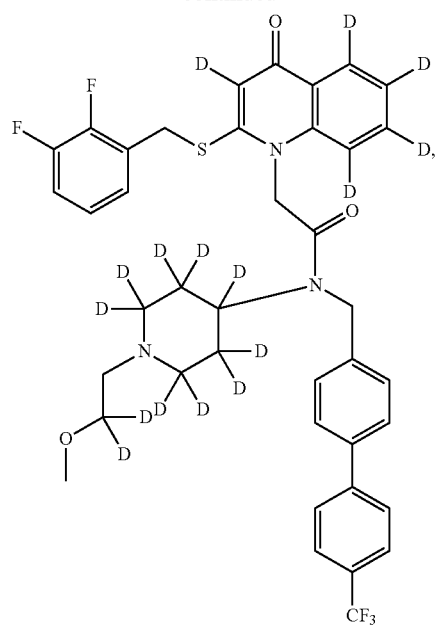
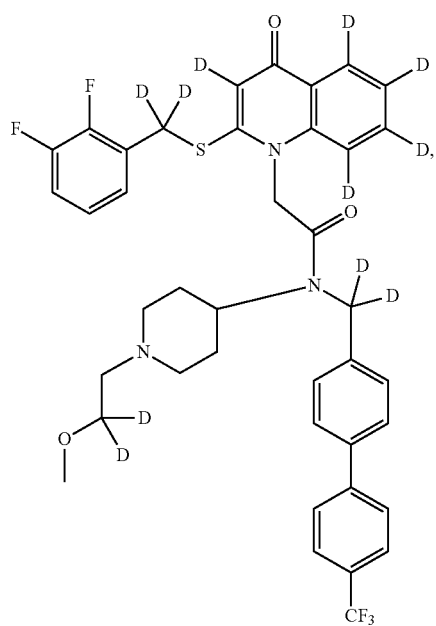
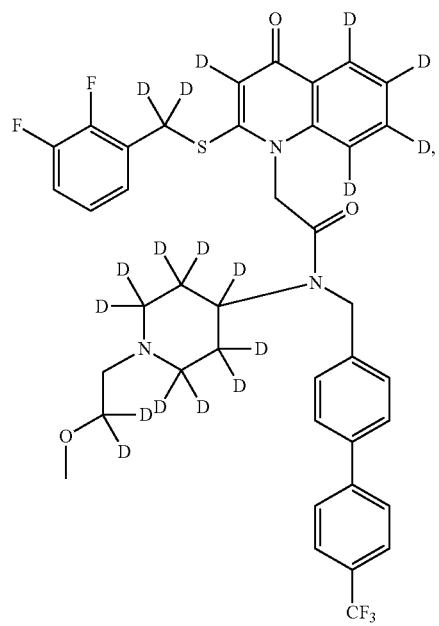

171
-continued
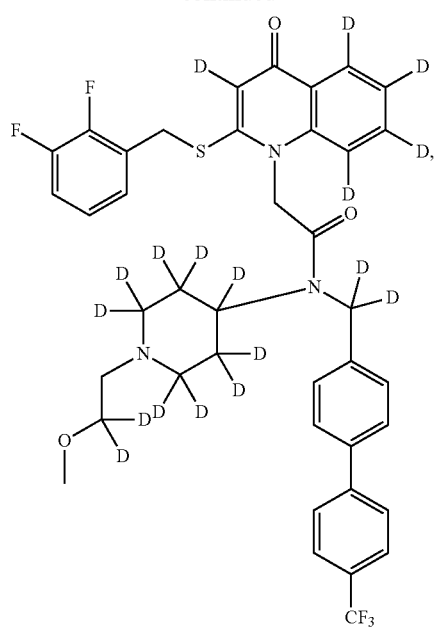
172
-continued
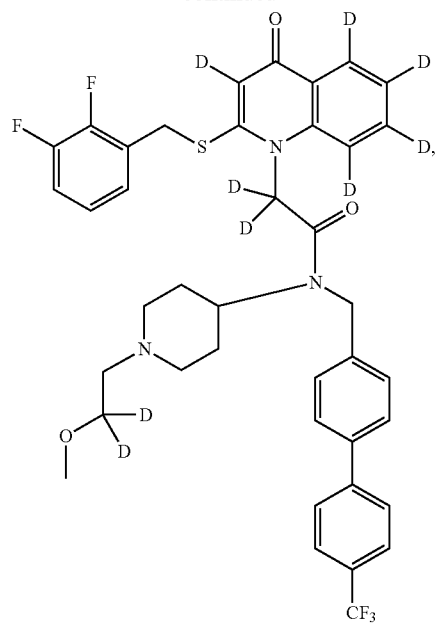
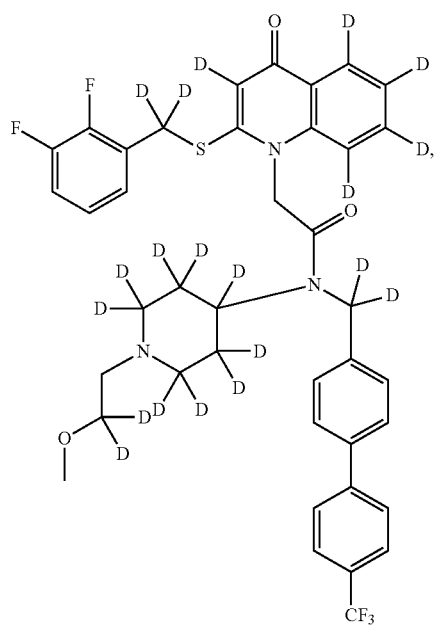
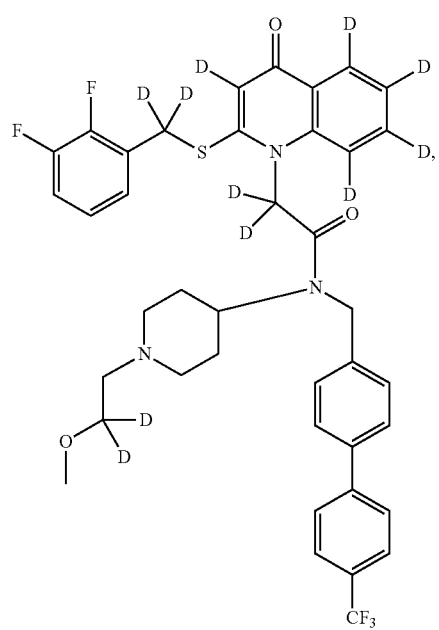

173
-continued
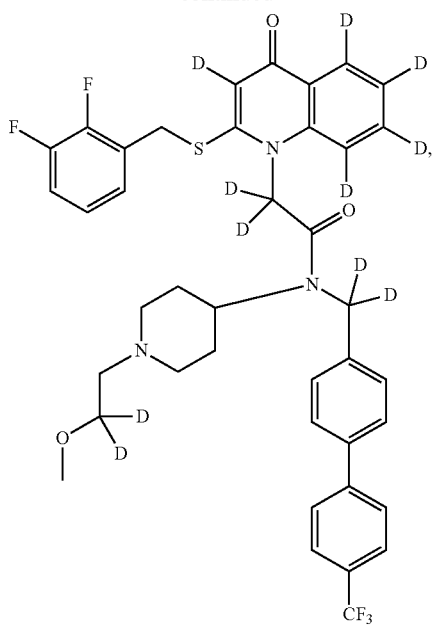
174
-continued
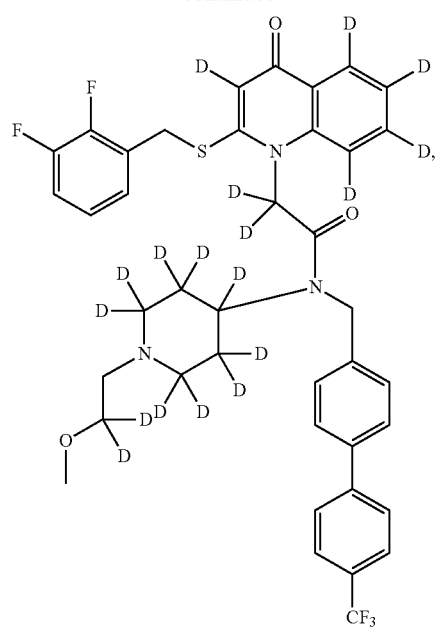
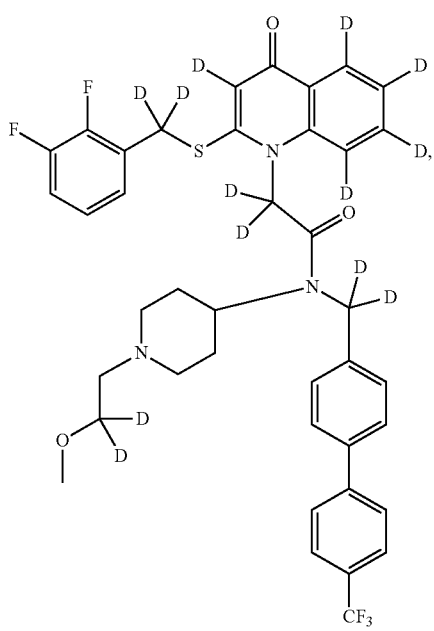
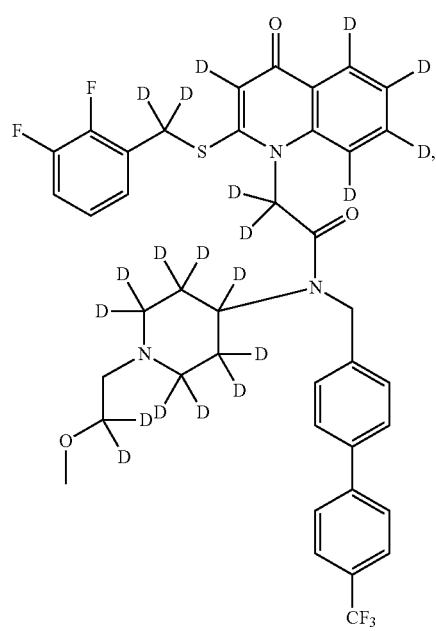

175
-continued
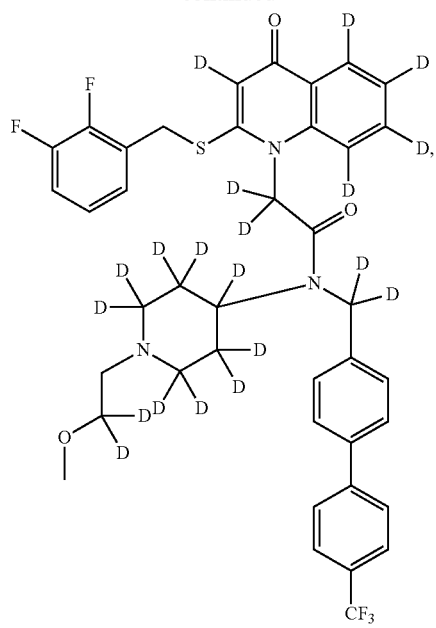
176
-continued
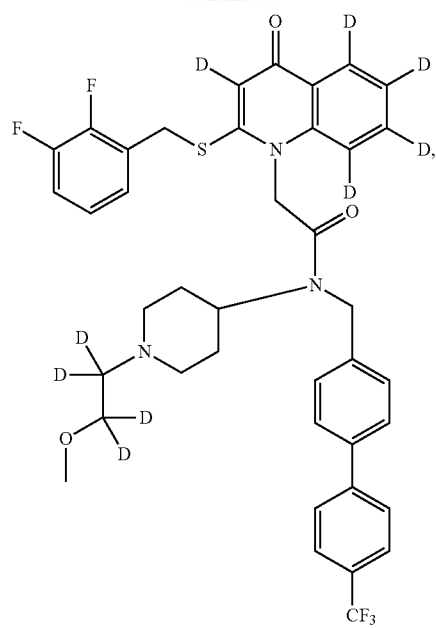
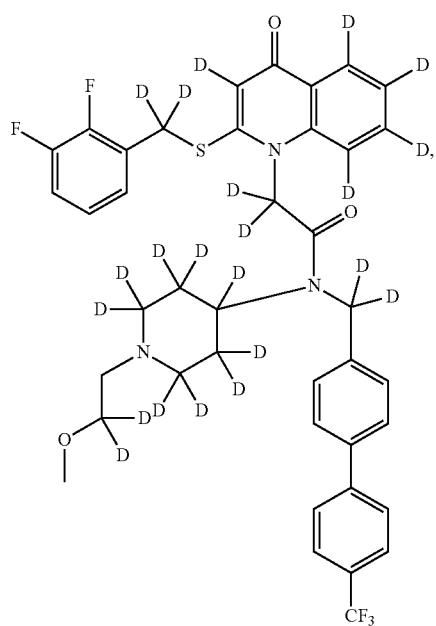
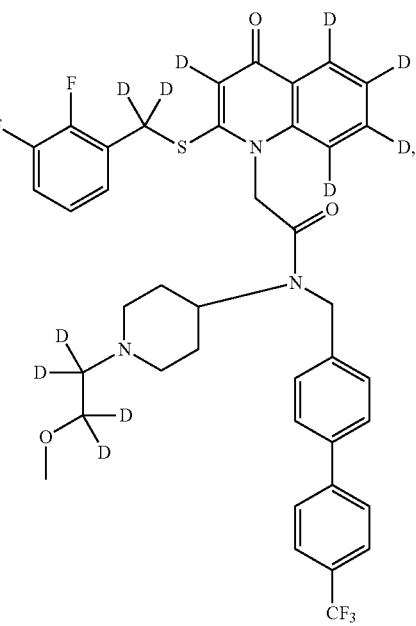

177
-continued
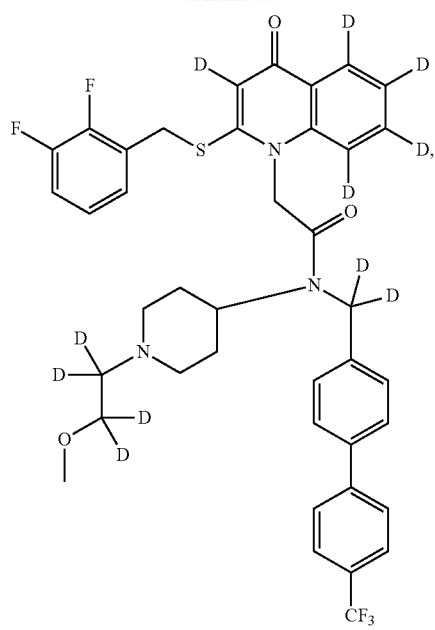
178
-continued
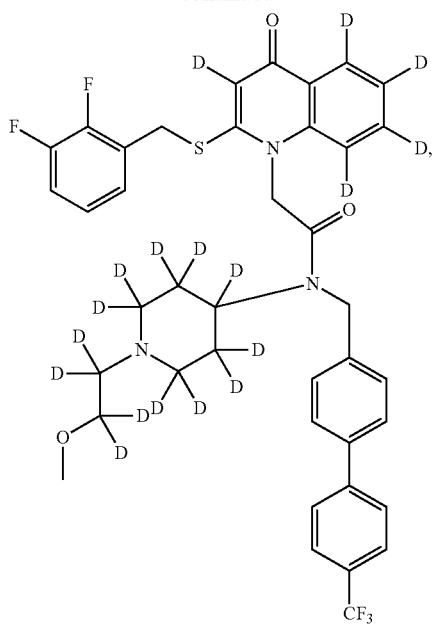
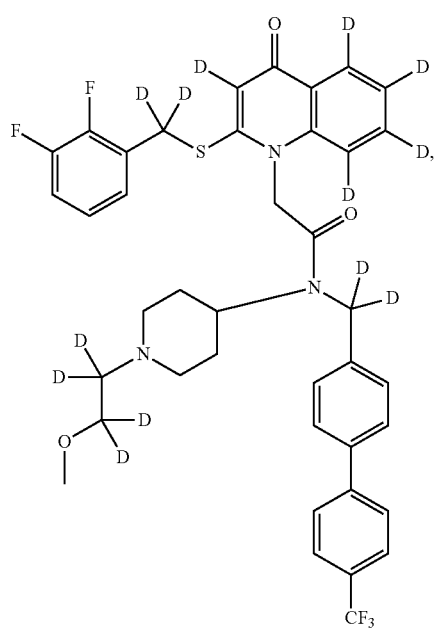
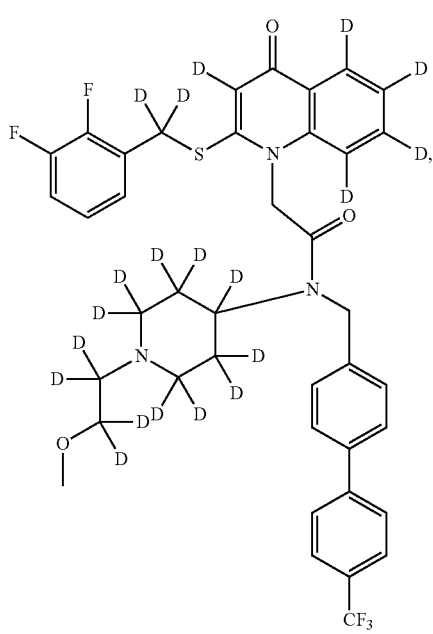

179
-continued
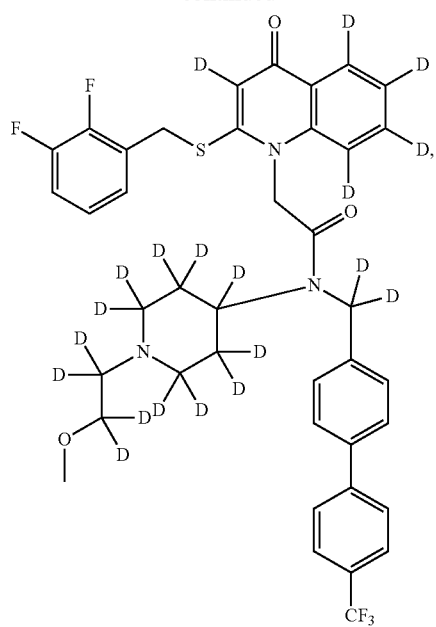
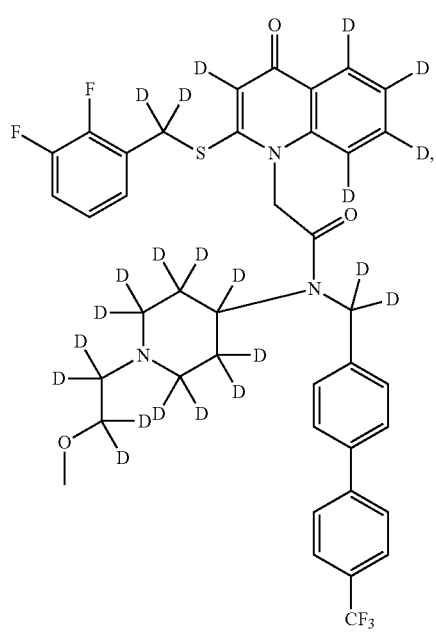
180
-continued
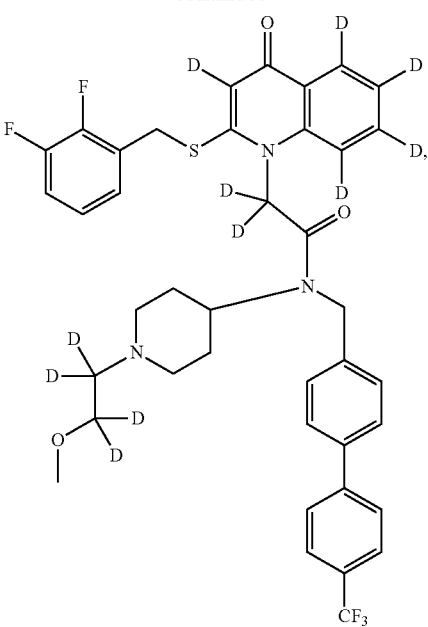

181
-continued
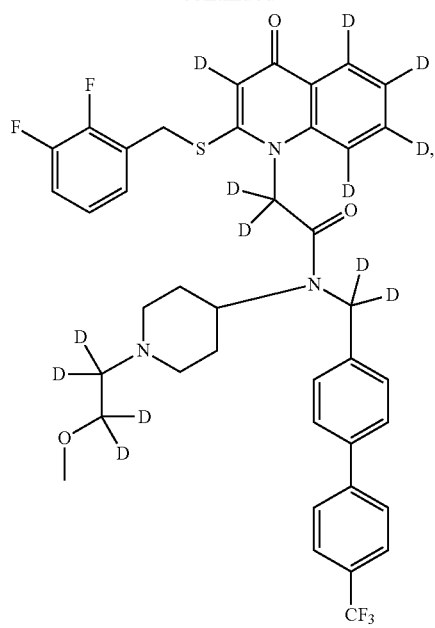
182
-continued
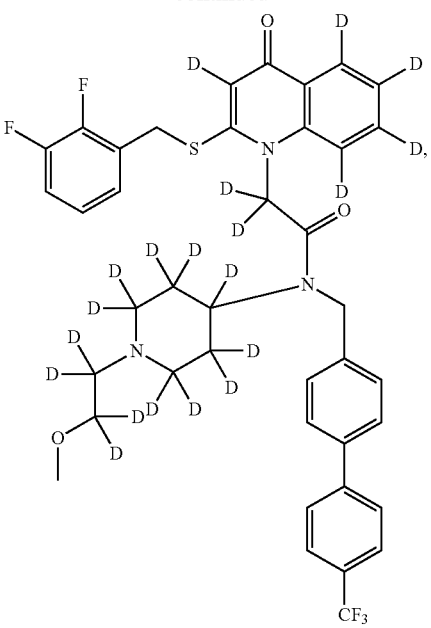
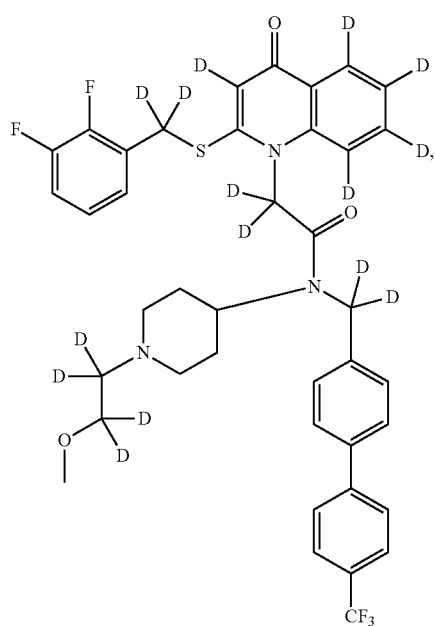
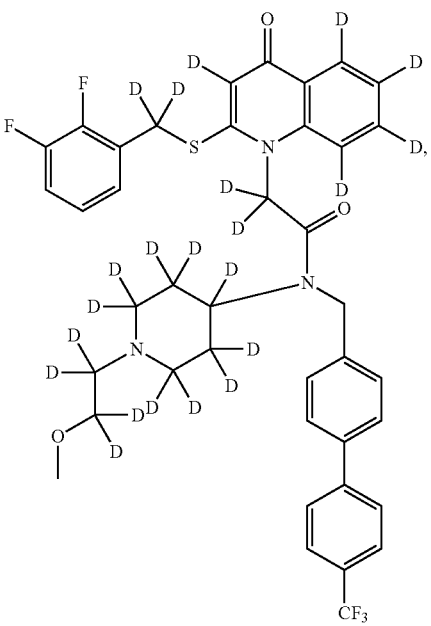

183
-continued
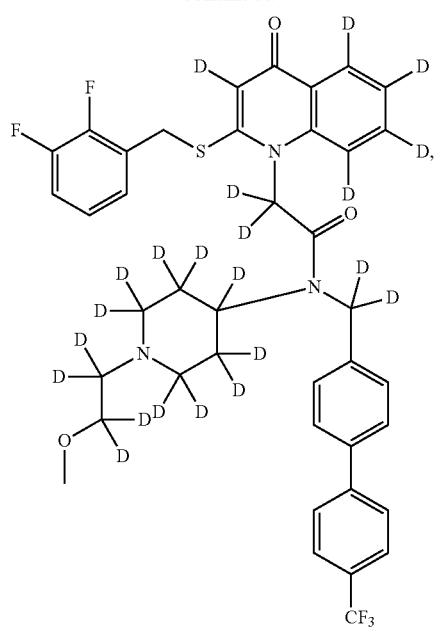
184
-continued
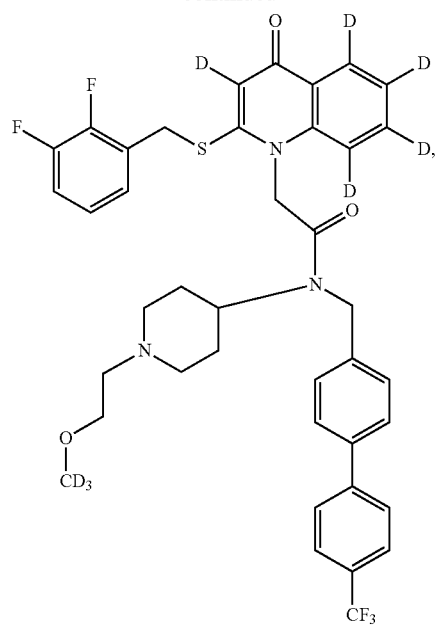
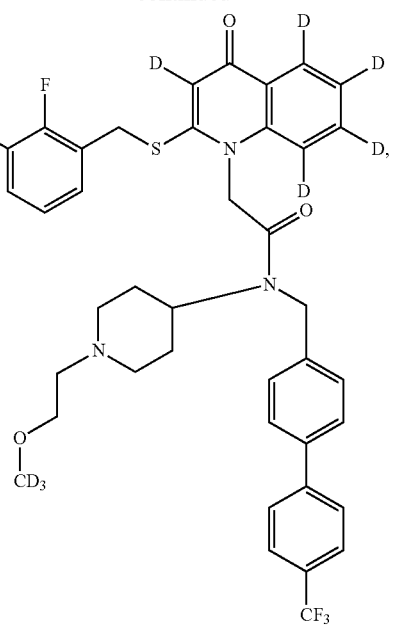

185
-continued
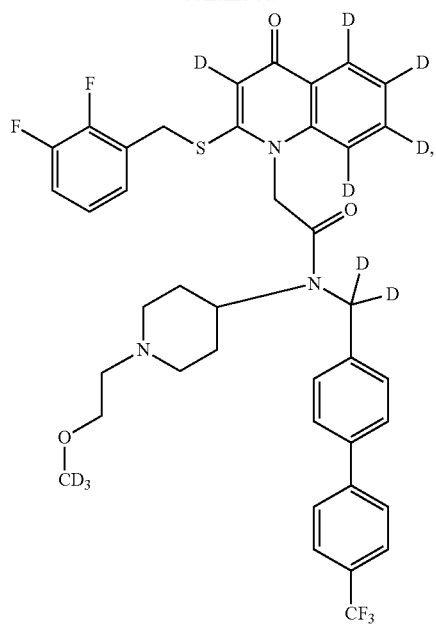
186
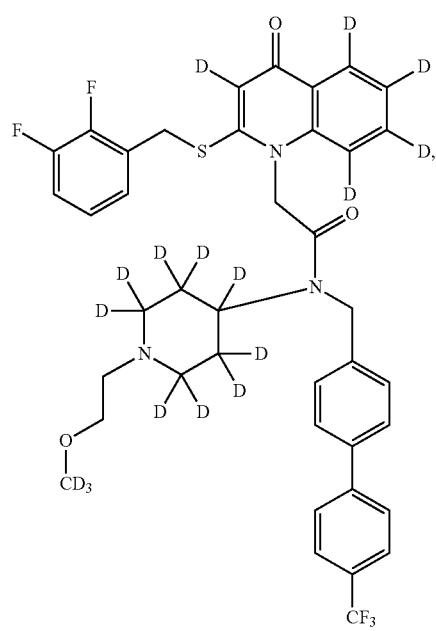
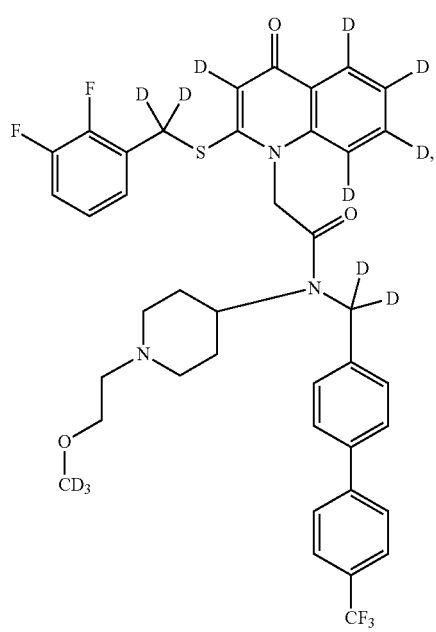
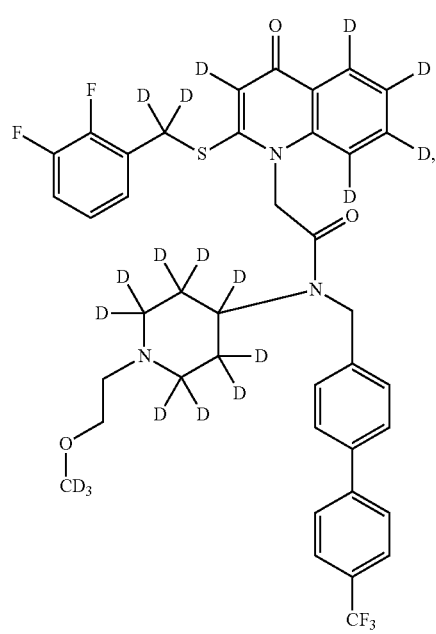

187
-continued
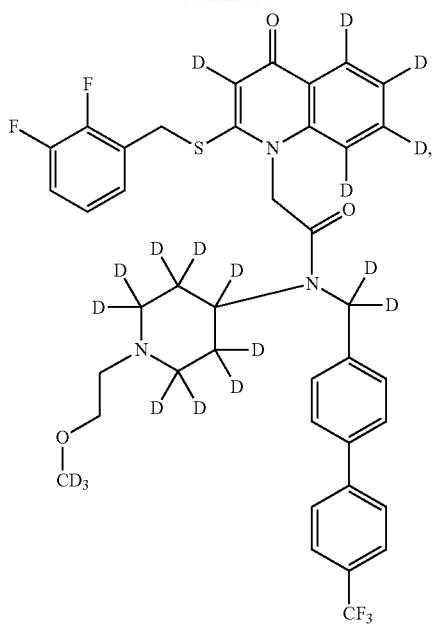
188
-continued
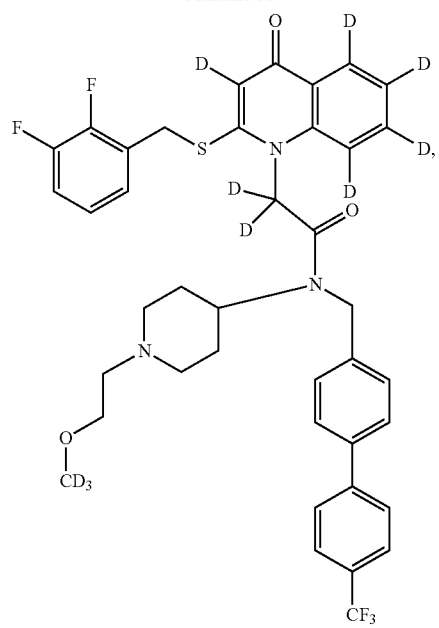
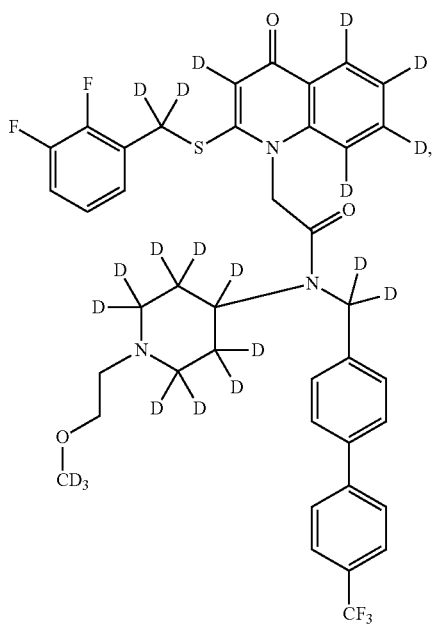
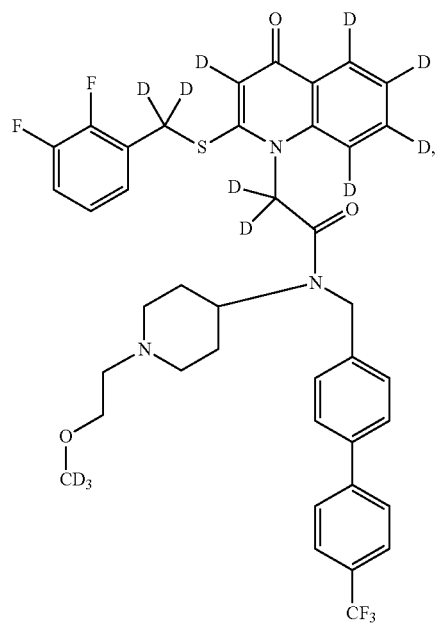

189
-continued
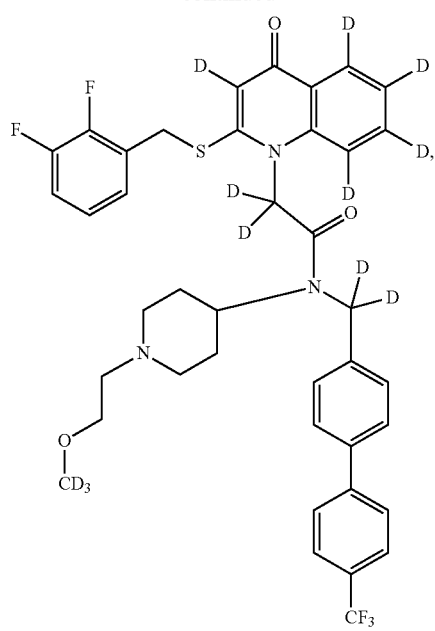
190
-continued
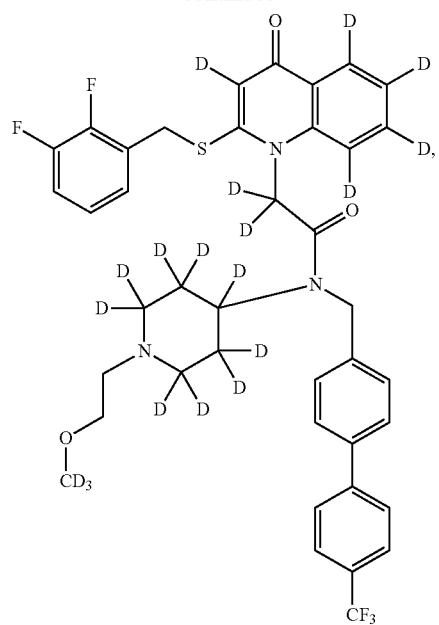
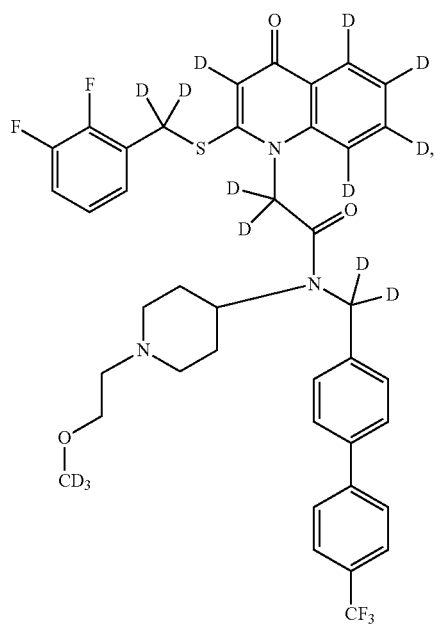
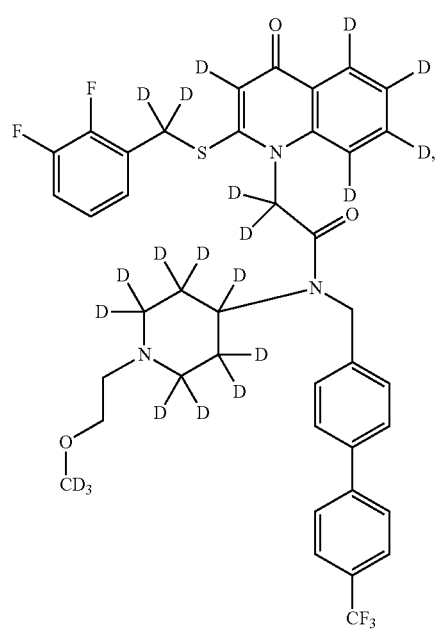

191
-continued
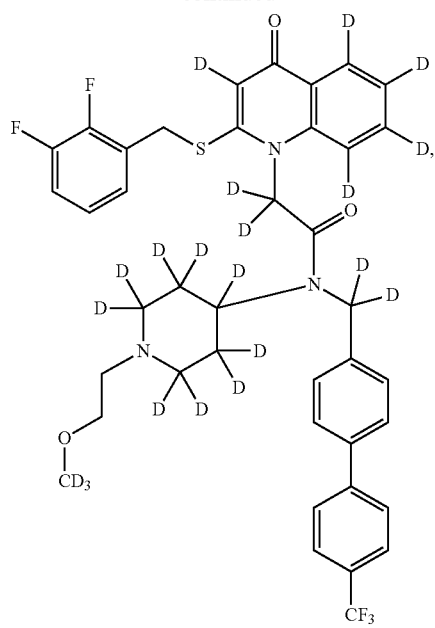
192
-continued
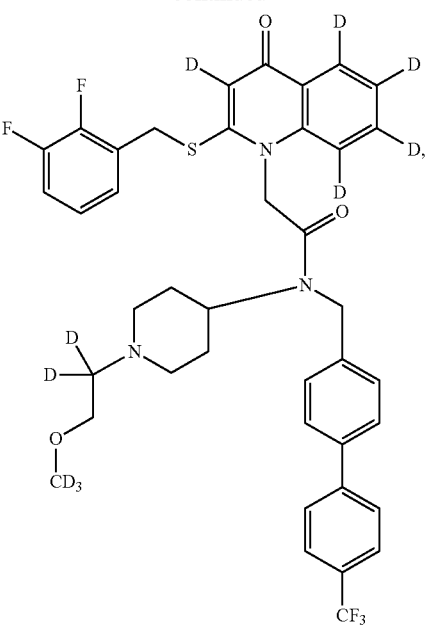
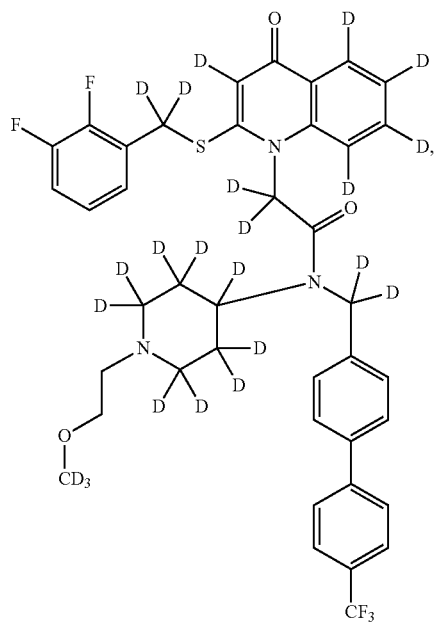
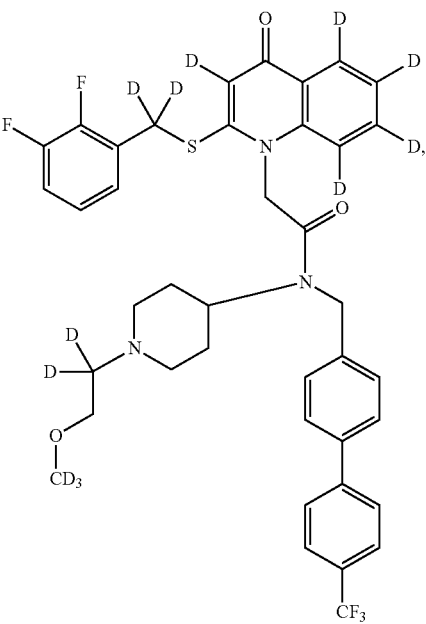

193
-continued
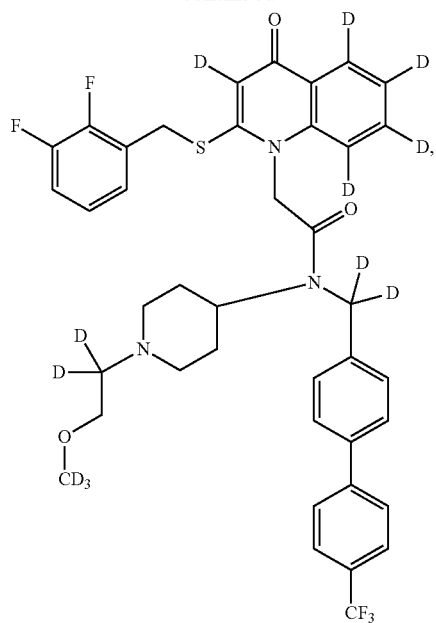
194
-continued
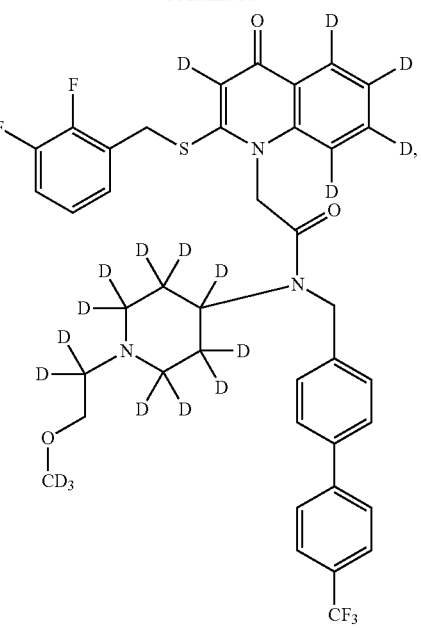
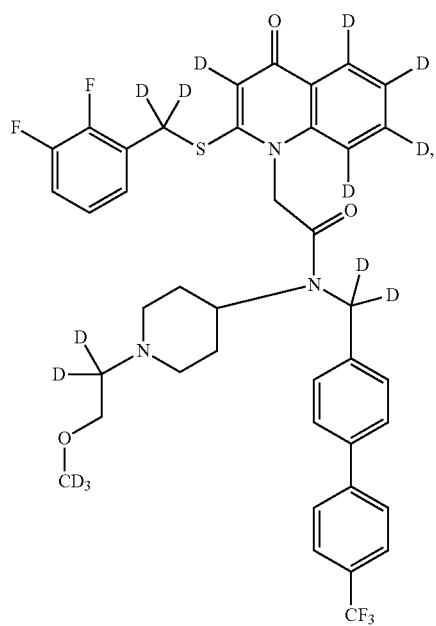
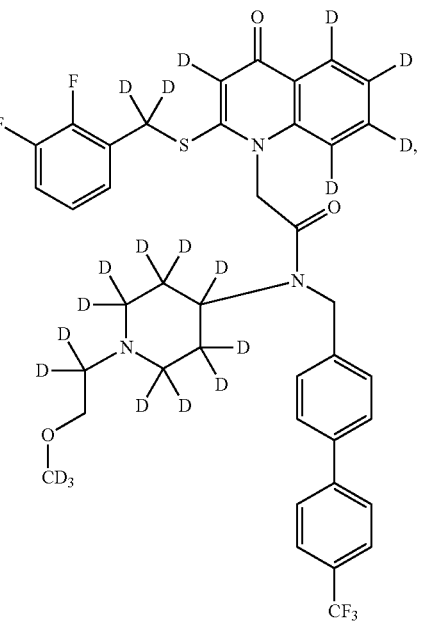

195
-continued
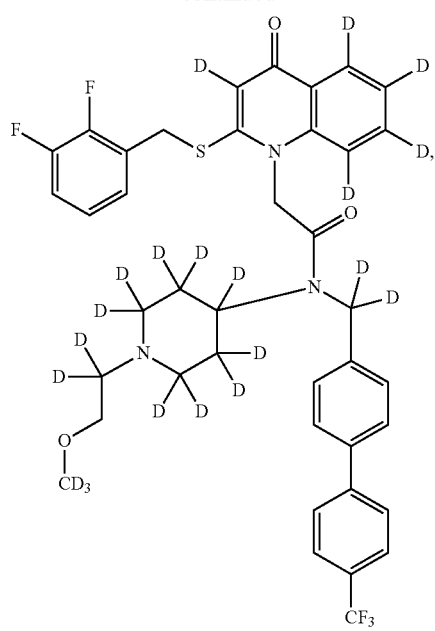
196
-continued
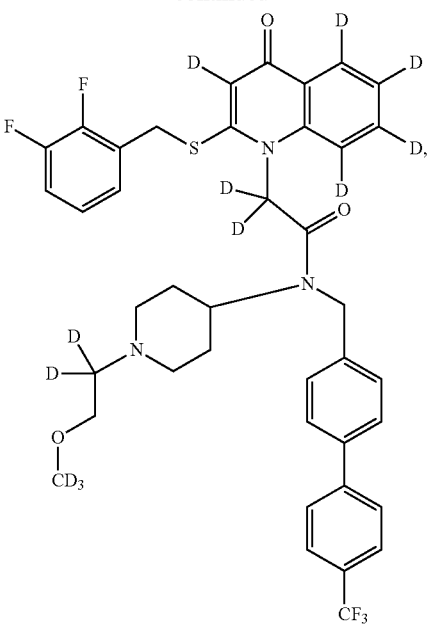
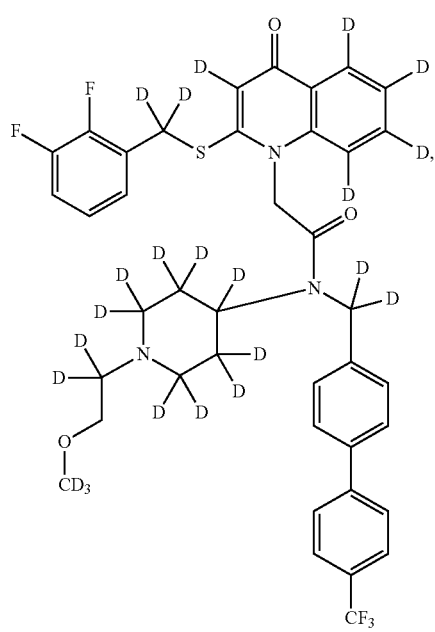

197
-continued
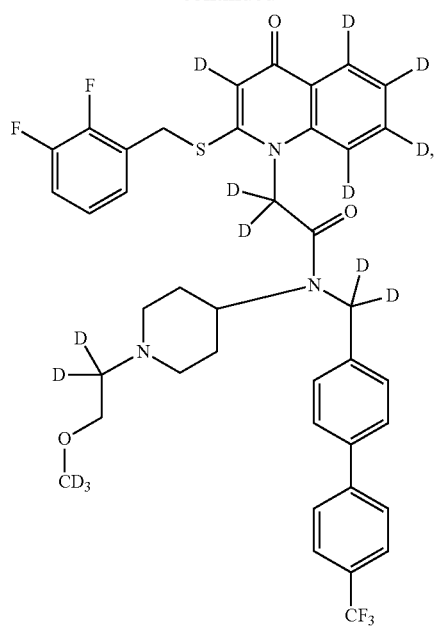
198
-continued
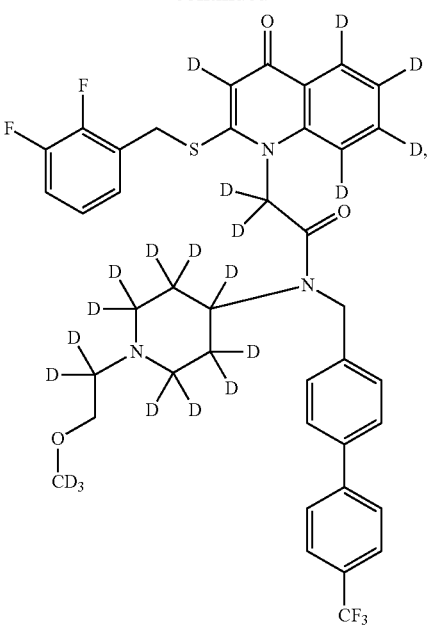
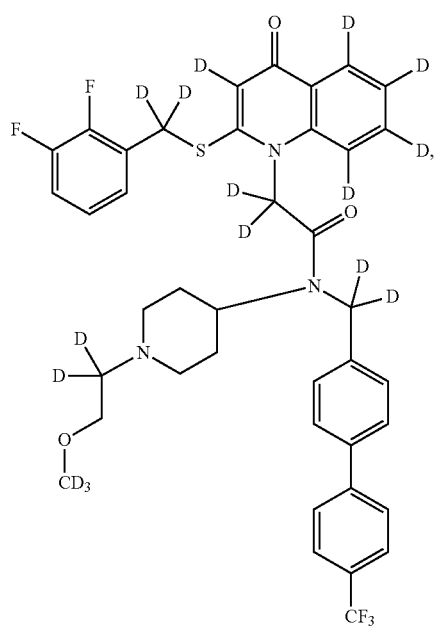
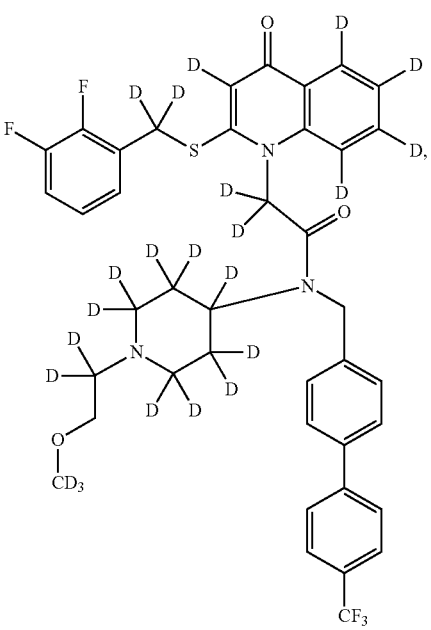

199
-continued
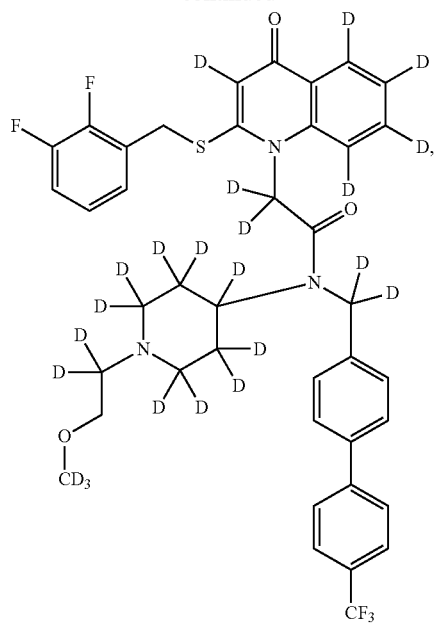
200
-continued
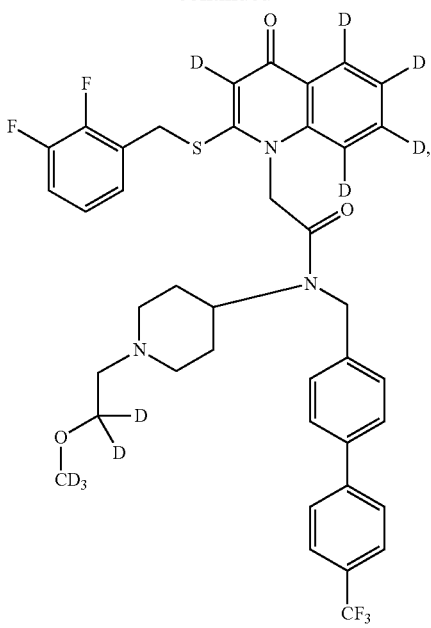
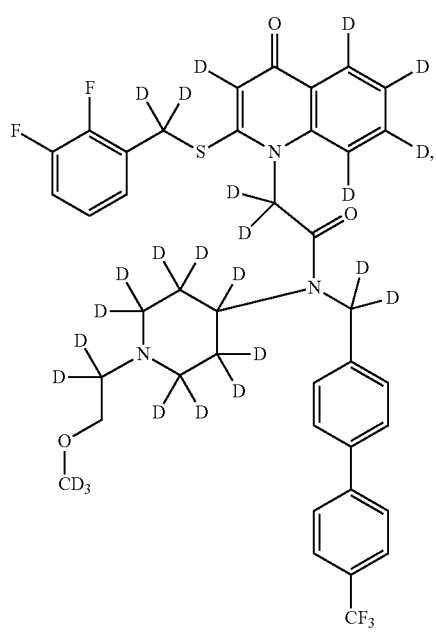
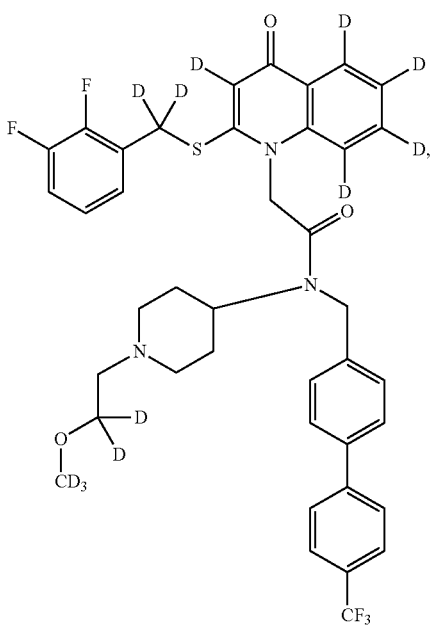

201
-continued
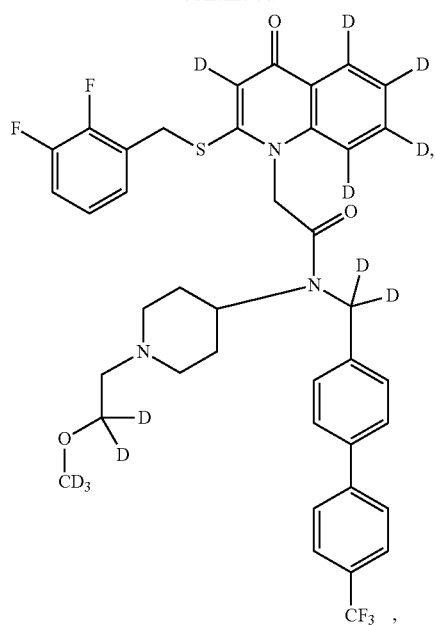
202
-continued
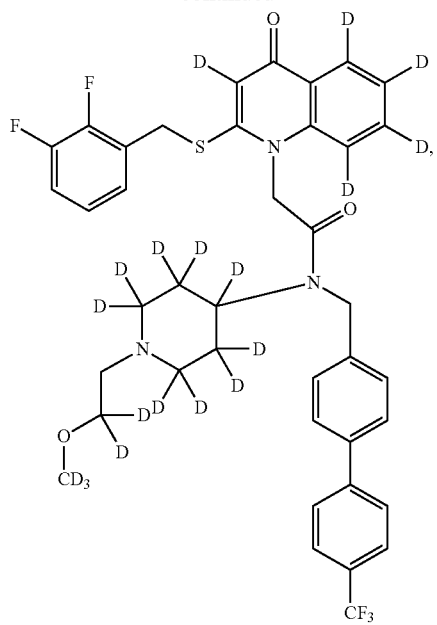
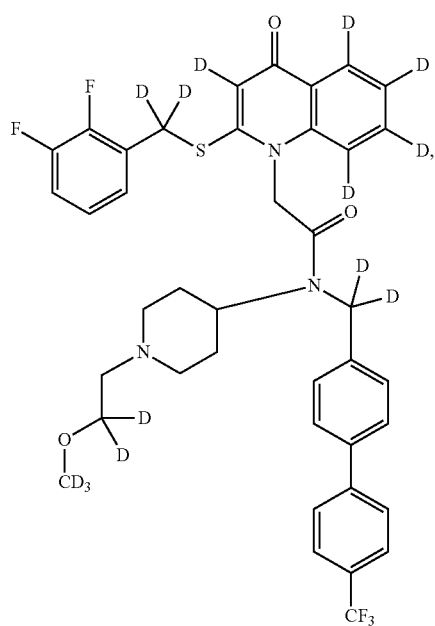
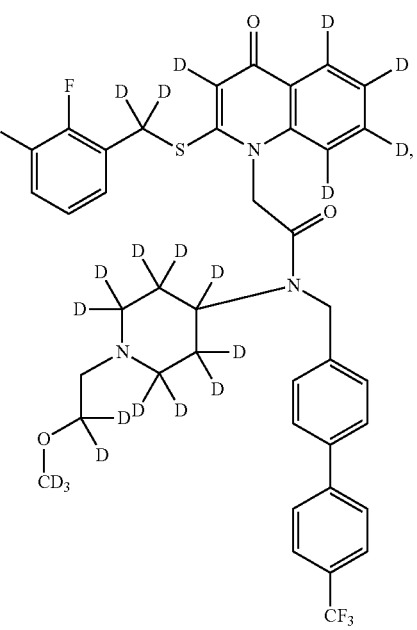

203
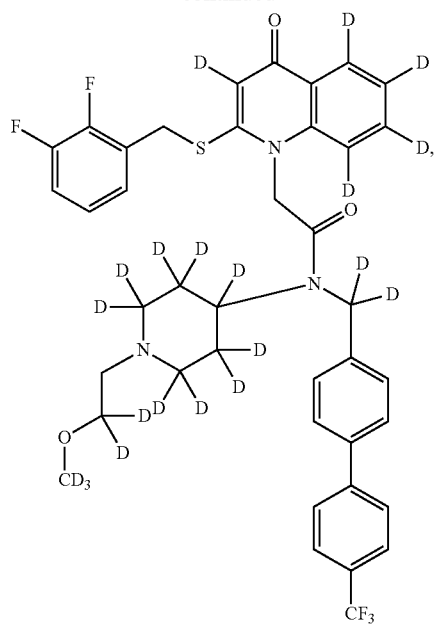
204
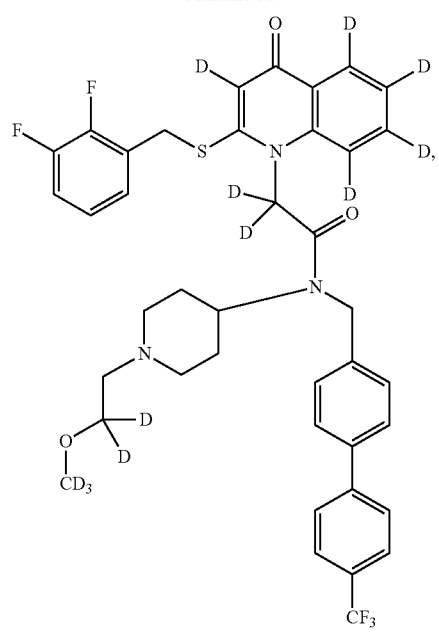
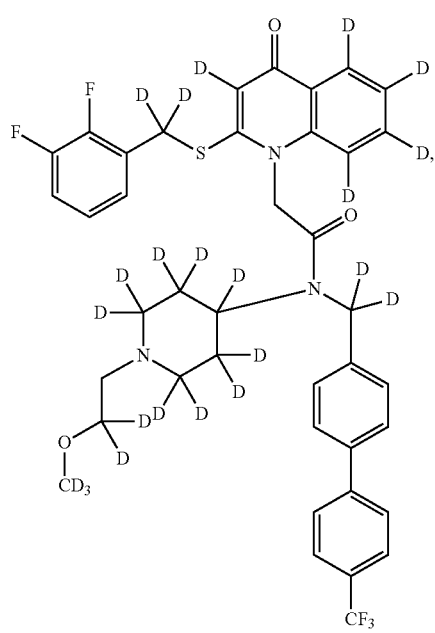

205
-continued
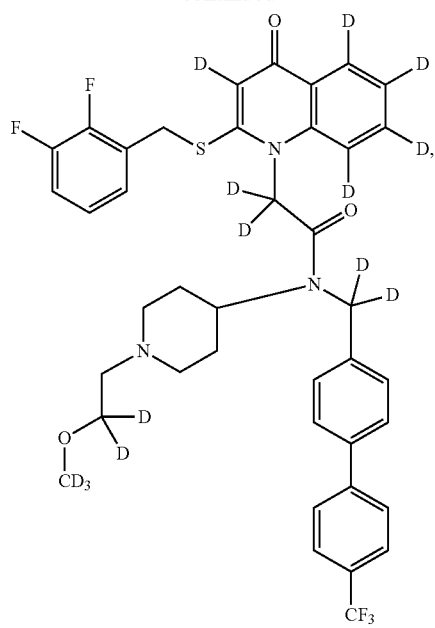
206
-continued
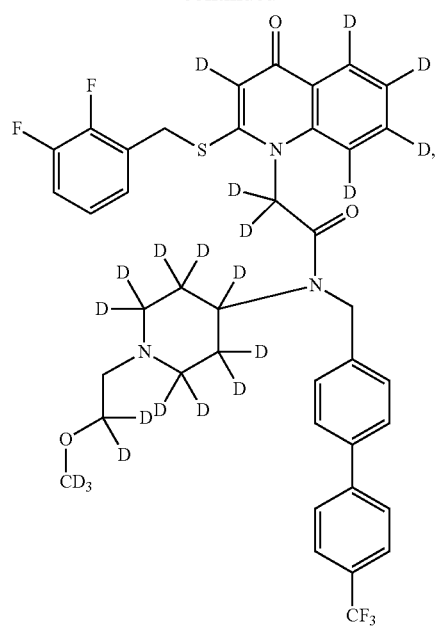
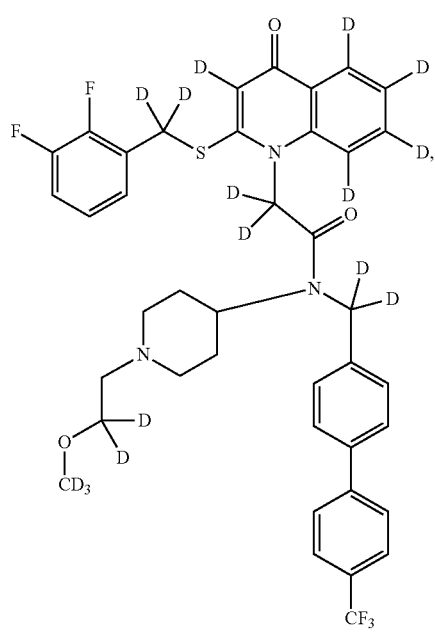

207
-continued
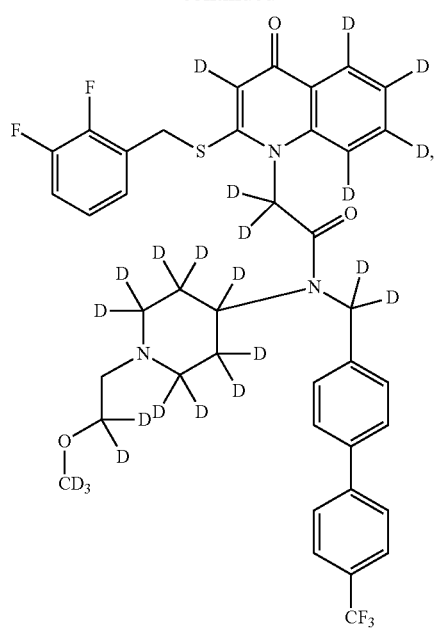
208
-continued
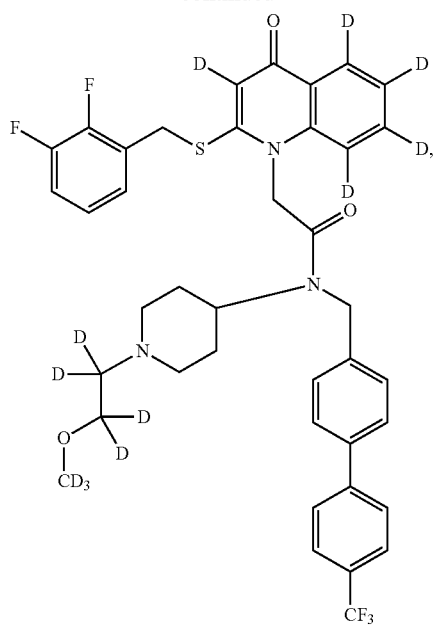

209
-continued
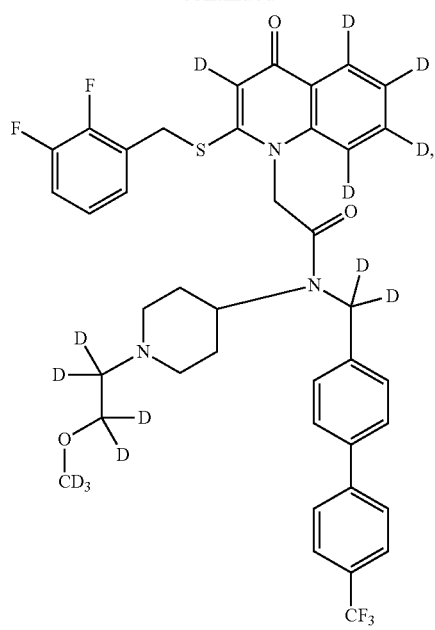
210
-continued
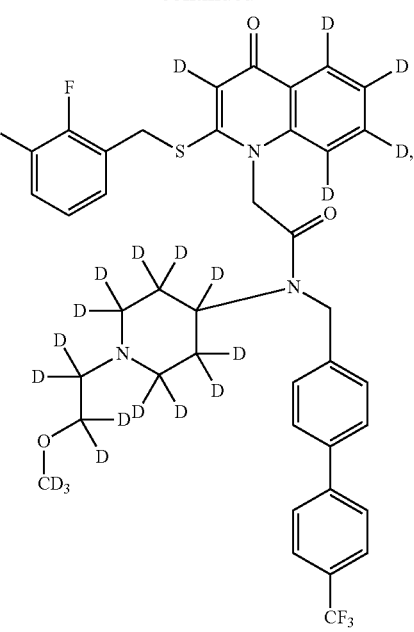
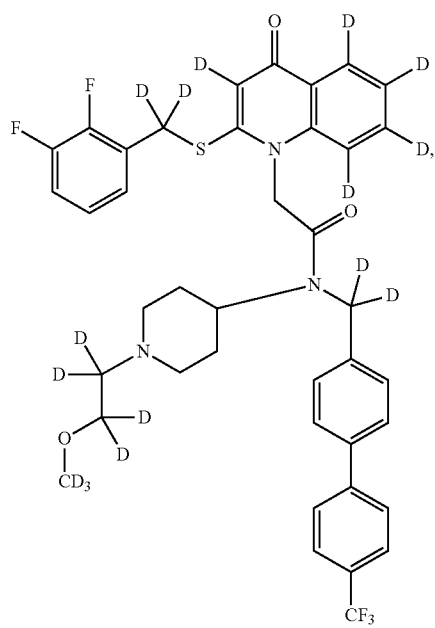
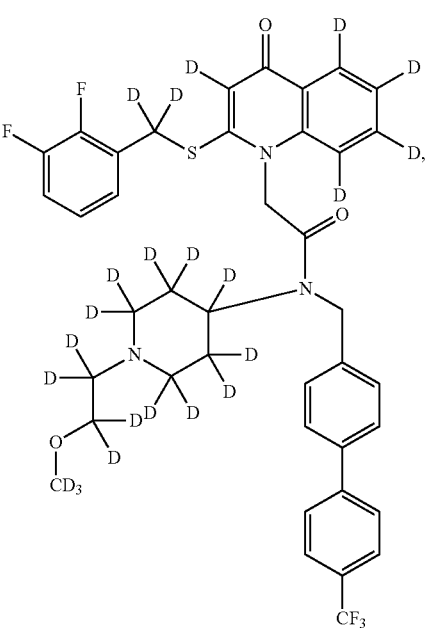

211
-continued
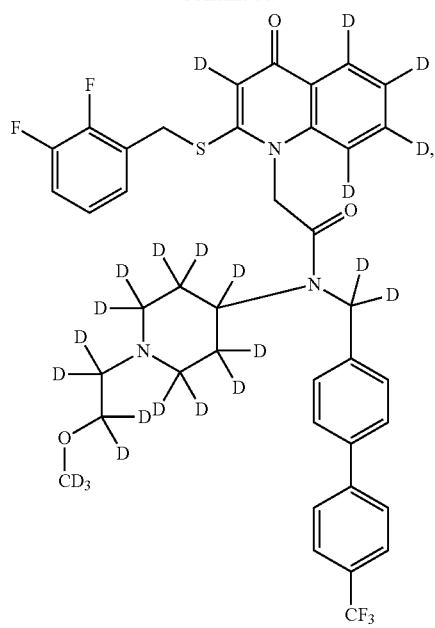
212
-continued
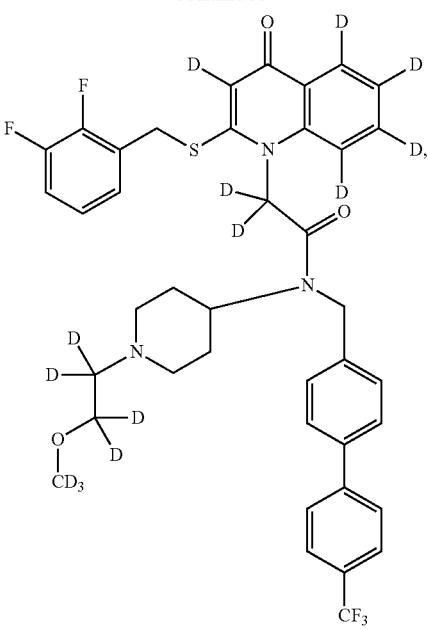
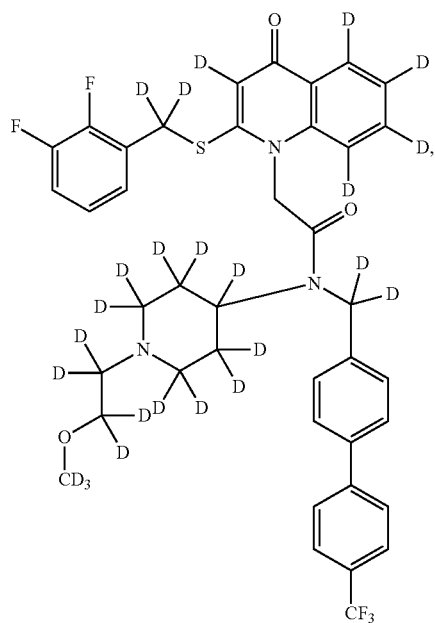
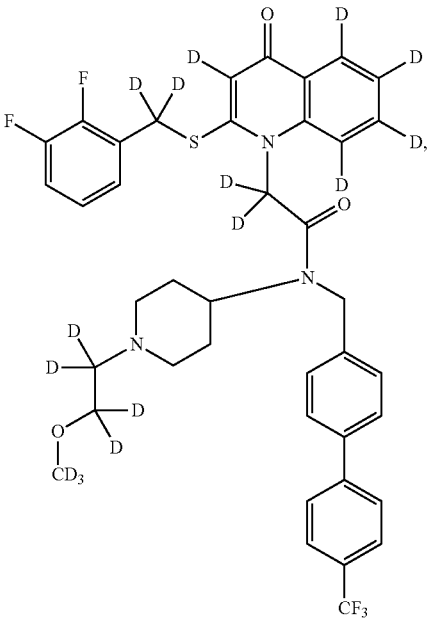

213
-continued
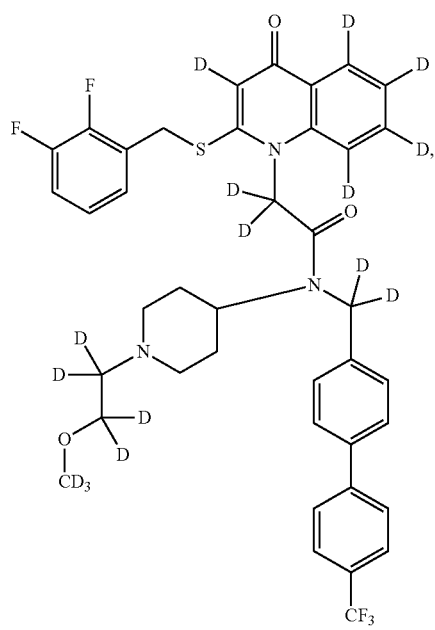
214
-continued
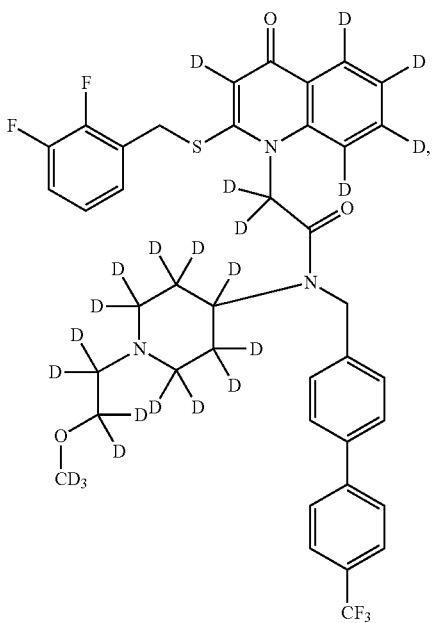

-continued

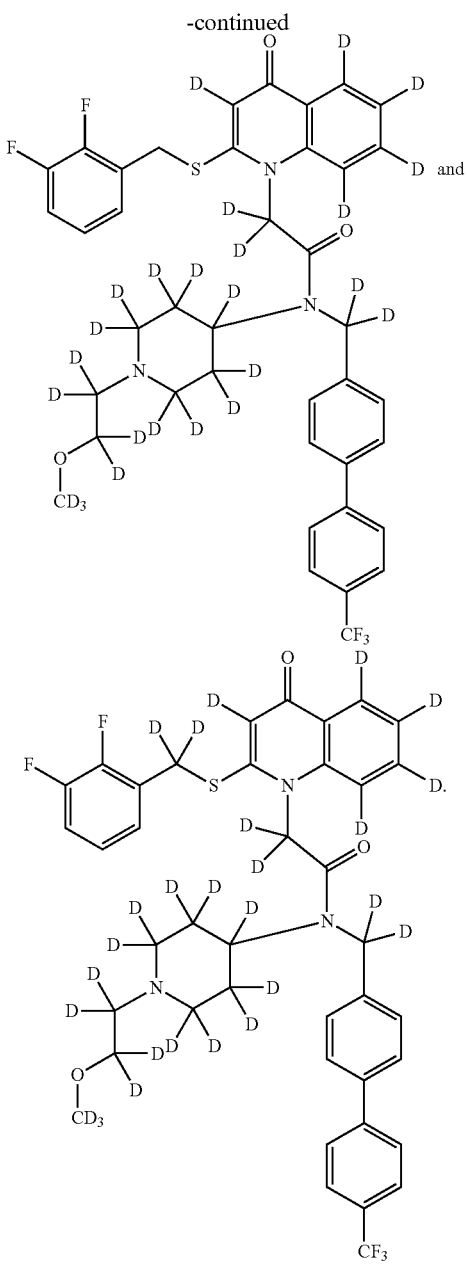

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In Vitro Liver Microsomal Stability Assay

Liver microsomal stability assays are conducted at 1 mg per mL liver microsome protein with an NADPH-generating system in 2% sodium bicarbonate (2.2 mM NADPH, 25.6 mM glucose 6-phosphate, 6 units per mL glucose 6-phosphate dehydrogenase and 3.3 mM magnesium chloride). Test compounds are prepared as solutions in 20% acetonitrile-water and added to the assay mixture (final assay concentration 5 microgram per mL) and incubated at 37° C.

Final concentration of acetonitrile in the assay should be <1%. Aliquots (50 μL) are taken out at times 0, 15, 30, 45, and 60 minutes, and diluted with ice cold acetonitrile (200 μL) to stop the reactions. Samples are centrifuged at 12,000 RPM for 10 minutes to precipitate proteins. Supernatants are transferred to microcentrifuge tubes and stored for LC/MS/MS analysis of the degradation half-life of the test compounds.

In Vitro Metabolism Using Human Cytochrome $P_{450}$ Enzymes

The cytochrome $P_{450}$ enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound as disclosed herein, the corresponding non-isotopically enriched compound or standard or control in 100 millimolar potassium phosphate (pH 7.4) is incubated at 37° C. for 20 minutes. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 minutes. The supernatant is analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}C$]-(S)-mephenytoin |
| CYP2C8 | Paclitaxel |
| CYP2C9 | Diclofenac |
| CYP2C19 | [$^{13}C$]-(S)-mephenytoin |
| CYP2D6 | (+/−)-Bufuralol |
| CYP2E1 | Chlorzoxazone |
| CYP3A4 | Testosterone |
| CYP4A | [$^{13}C$]-Lauric acid |

Monoamine Oxidase A Inhibition and Oxidative Turnover

The procedure is carried out using the methods described by Weyler et al., *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM sodium phosphate buffer, pH 7.2, containing 0.2% Triton X-100 (monoamine oxidase assay buffer), plus 1 mM kynuramine, and the desired amount of enzyme in 1 mL total volume.

Monooamine Oxidase B Inhibition and Oxidative Turnover

The procedure is carried out as described in Uebelhack et al., *Pharmacopsychiatry* 1998, 31(5), 187-192, which is hereby incorporated by reference in its entirety.

Lipoprotein-Associated Phospholipase A2 Selectivity Assay

The procedure is carried out as described in Wilensky et al., *Nature Medicine* 2008, 14(10), 1059-66, which is hereby incorporated by reference in its entirety.

Arterial Lp-PLA2 Abundance

The procedure is carried out as described in Wilensky et al., *Nature Medicine* 2008, 14(10), 1059-66, which is hereby incorporated by reference in its entirety.

Influence of Lipoprotein-Associated Phospholipase A2 Inhibitors on Coronary Artery Gene Expression The procedure is carried out as described in Wilensky et al., *Nature Medicine* 2008, 14(10), 1059-66, which is hereby incorporated by reference in its entirety.

Complex Coronary Lesion Development Assay

The procedure is carried out as described in Wilensky et al., *Nature Medicine* 2008, 14(10), 1059-66, which is hereby incorporated by reference in its entirety.

Screen for Lp-PLA2 Inhibition

The procedure is carried out as described in WO 2002030904, which is hereby incorporated by reference in its entirety.

Lp-PLA2 Assay

The procedure is carried out as described in Mohler et al., *J. Am. Coll. Cardiol* 2008, 51(17), 1632-41, which is hereby incorporated by reference in its entirety.

From the foregoing description, one skilled in the art can ascertain the essential characteristics of this invention, and without departing from the spirit and scope thereof, can make various changes and modifications of the invention to adapt it to various usages and conditions.

What is claimed is:

1. A method of treating a lipoprotein-associated phospholipase A2-mediated disorder comprising administering to a subject in need thereof a therapeutically effective amount of a compound of structural Formula I:

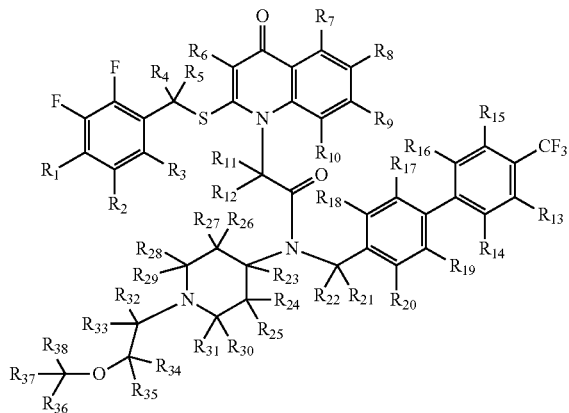

(I)

or a pharmaceutically acceptable salt thereof, wherein:
  $R_1$-$R_{38}$ are independently selected from the group consisting of hydrogen and deuterium; and
  at least one of $R_1$-$R_{38}$ is deuterium;
  resulting in at least one effect selected from the group consisting of:
  a. decreased inter-individual variation in plasma levels of said compound or a metabolite thereof as compared to the non-isotopically enriched compound;
  b. increased average plasma levels of said compound per dosage unit thereof as compared to the non-isotopically enriched compound;
  c. decreased average plasma levels of at least one metabolite of said compound per dosage unit thereof as compared to the non-isotopically enriched compound;
  d. increased average plasma levels of at least one metabolite of said compound per dosage unit thereof as compared to the non-isotopically enriched compound; and
  e. an improved clinical effect during the treatment in said subject per dosage unit thereof as compared to the non-isotopically enriched compound.

2. The method as recited in claim 1, further resulting in at least two effects selected from the group consisting of:
  a. decreased inter-individual variation in plasma levels of said compound or a metabolite thereof as compared to the non-isotopically enriched compound;
  b. increased average plasma levels of said compound per dosage unit thereof as compared to the non-isotopically enriched compound;
  c. decreased average plasma levels of at least one metabolite of said compound per dosage unit thereof as compared to the non-isotopically enriched compound;
  d. increased average plasma levels of at least one metabolite of said compound per dosage unit thereof as compared to the non-isotopically enriched compound; and
  e. an improved clinical effect during the treatment in said subject per dosage unit thereof as compared to the non-isotopically enriched compound.

3. The method as recited in claim 1 wherein said disorder is selected from the group consisting of coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, and asthma.

4. The method as recited in claim 1 wherein said compound has a structural formula selected from the group consisting of:

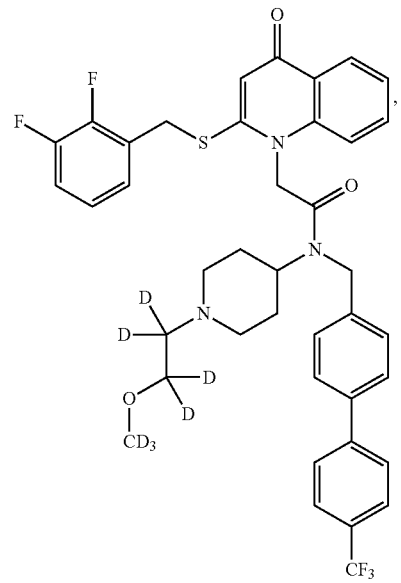

219
-continued
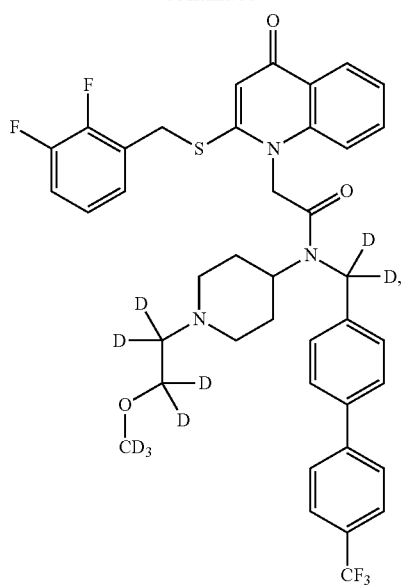
220
-continued
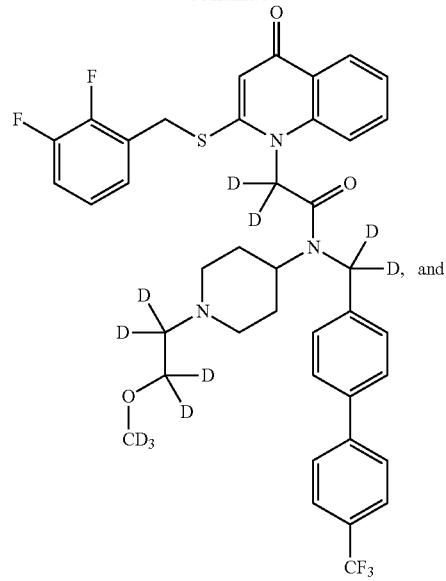
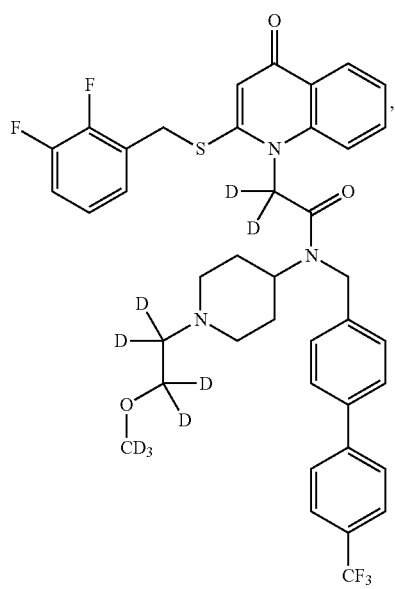
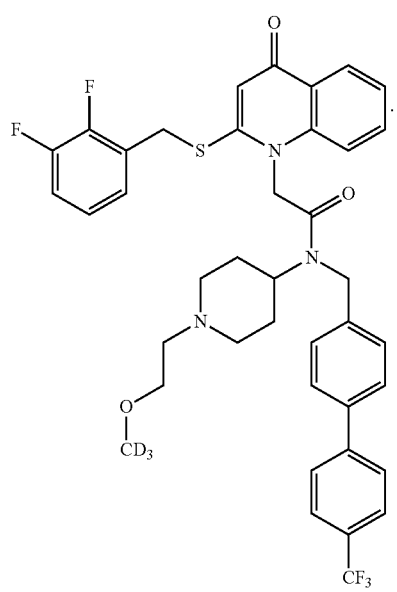
5. A method of treating a lipoprotein-associated phospholipase A2-mediated disorder comprising administering to a subject in need thereof a therapeutically effective amount of a compound of structural Formula I:

(I)

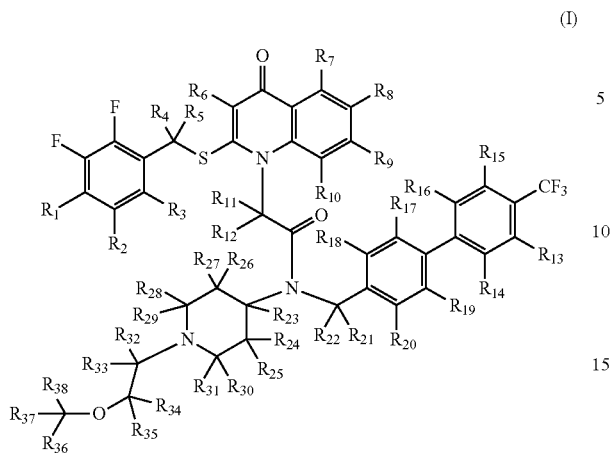

or a pharmaceutically acceptable salt thereof, wherein:
$R_1$-$R_{38}$ are independently selected from the group consisting of hydrogen and deuterium; and
at least one of $R_1$-$R_{38}$ is deuterium;
wherein the method effects a decreased metabolism of the compound per dosage unit thereof by at least one polymorphically-expressed cytochrome $P_{450}$ isoform in the subject, as compared to the corresponding non-isotopically enriched compound.

6. The method as recited in claim 5, wherein the cytochrome $P_{450}$ isoform is selected from the group consisting of CYP2C8, CYP2C9, CYP2C19, and CYP2D6.

7. The method as recited in claim 5 wherein said disorder is selected from the group consisting of coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, and asthma.

8. The method as recited in claim 5 wherein said compound has a structural formula selected from the group consisting of:

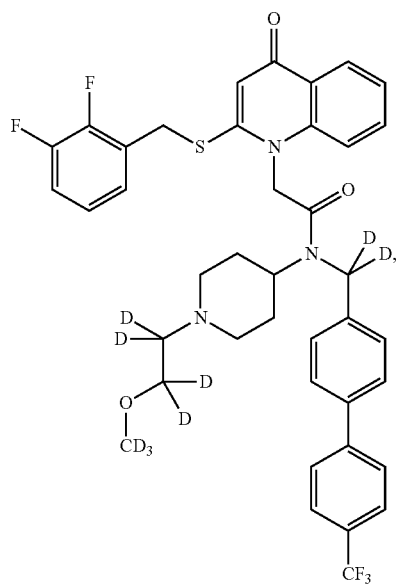

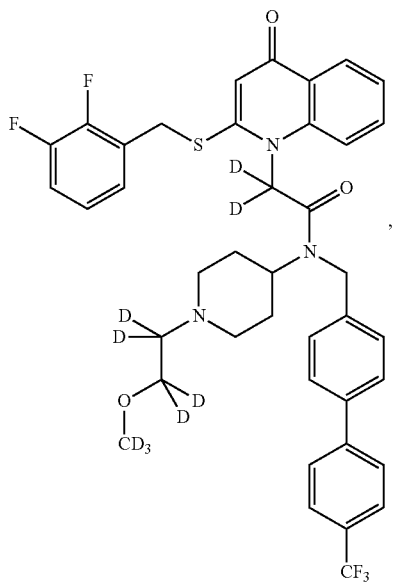

223
-continued

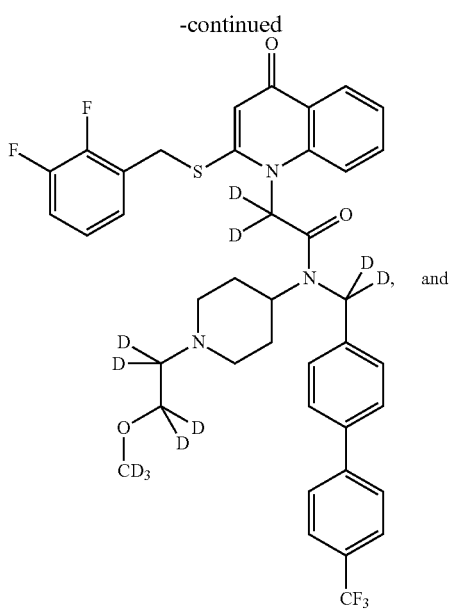

and

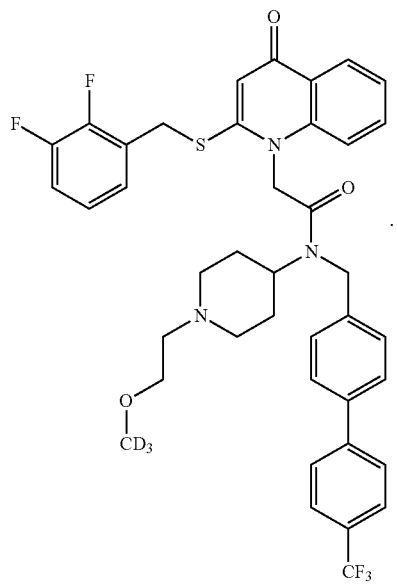

9. A method of treating a lipoprotein-associated phospholipase A2-mediated disorder comprising administering to a subject in need thereof a therapeutically effective amount of a compound of structural Formula I:

224

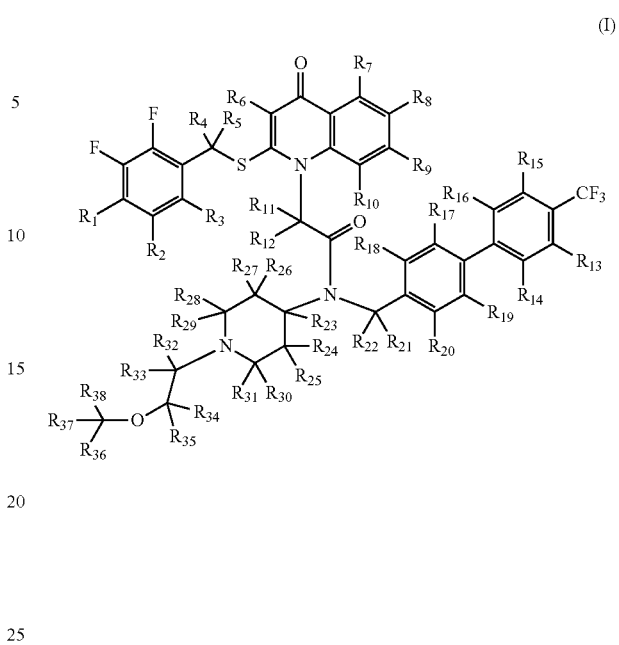

(I)

or a pharmaceutically acceptable salt thereof, wherein:
$R_1$-$R_{38}$ are independently selected from the group consisting of hydrogen and deuterium; and
at least one of $R_1$-$R_{38}$ is deuterium;
wherein said compound is characterized by decreased inhibition of at least one cytochrome $P_{450}$ or monoamine oxidase isoform in said subject per dosage unit thereof as compared to the non-isotopically enriched compound.

10. The method as recited in claim 9, wherein said cytochrome $P_{450}$ or monoamine oxidase isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, $MAO_A$, and $MAO_B$.

11. The method as recited in claim 9 wherein said disorder is selected from the group consisting of coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, and asthma.

12. The method as recited in claim 9 wherein said compound has a structural formula selected from the group consisting of:

225
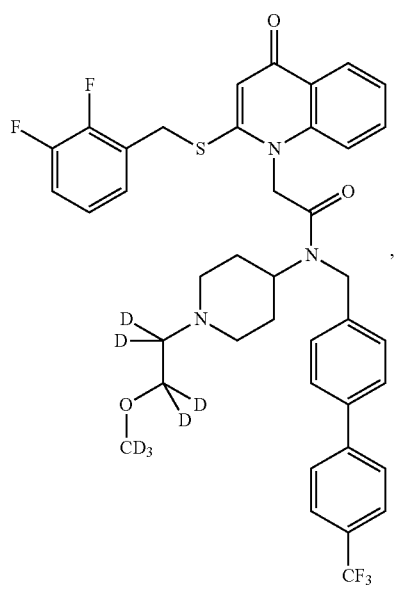
226
-continued
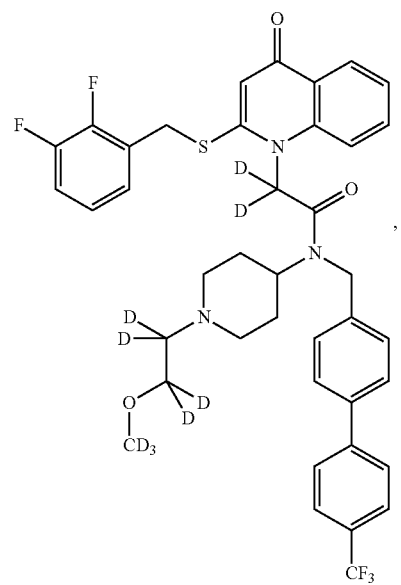
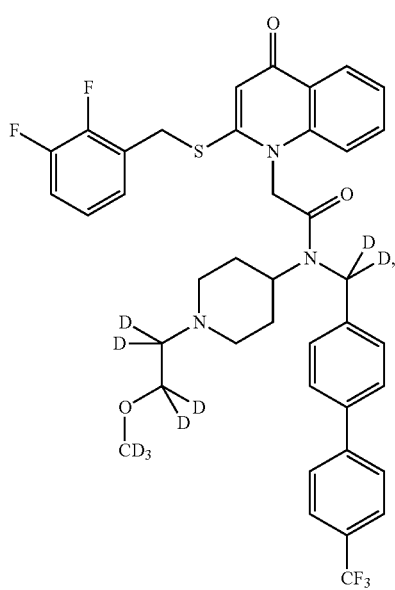
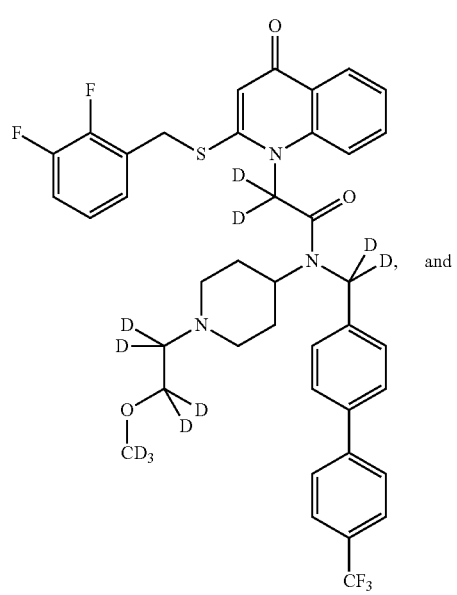 and

-continued

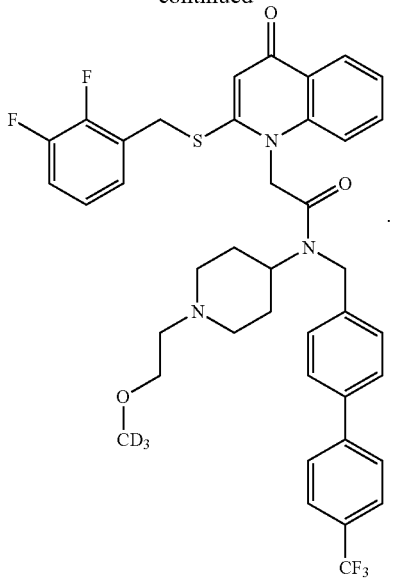

13. A method of treating a lipoprotein-associated phospholipase A2-mediated disorder comprising administering to a subject in need thereof a therapeutically effective amount of a compound of structural Formula I:

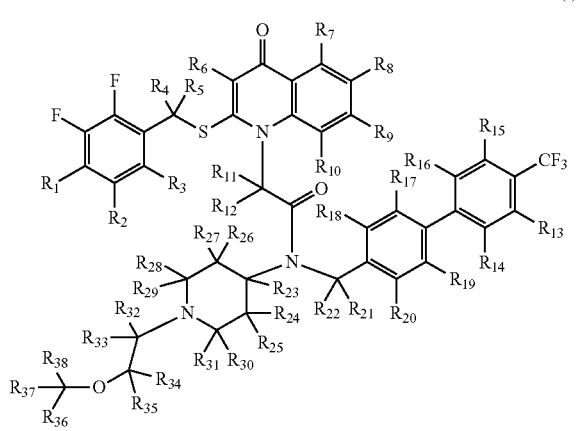
(I)

or a pharmaceutically acceptable salt thereof, wherein:
$R_1$-$R_{38}$ are independently selected from the group consisting of hydrogen and deuterium; and
at least one of $R_1$-$R_{38}$ is deuterium;

wherein the method reduces a deleterious change in a diagnostic hepatobiliary function endpoint, as compared to the corresponding non-isotopically enriched compound.

14. The method as recited in claim 13, wherein the diagnostic hepatobiliary function endpoint is selected from the group consisting of alanine aminotransferase ("ALT"), serum glutamic-pyruvic transaminase ("SGPT"), aspartate aminotransferase ("AST," "SGOT"), ALT/AST ratios, serum aldolase, alkaline phosphatase ("ALP"), ammonia levels, bilirubin, gamma-glutamyl transpeptidase ("GGTP," "γ-GTP," "GGT"), leucine aminopeptidase ("LAP"), liver biopsy, liver ultrasonography, liver nuclear scan, 5'-nucleotidase, and blood protein.

15. The method as recited in claim 13 wherein said disorder is selected from the group consisting of coronary disorders, primary and secondary coronary disorders, acute coronary disorders, atherosclerosis, peripheral vascular atherosclerosis, cerebrovascular atherosclerosis, rheumatoid arthritis, diabetes, stroke, myocardial infarction, reperfusion injury, acute and chronic inflammation, psoriasis, and asthma.

16. The method as recited in claim 13 wherein said compound has a structural formula selected from the group consisting of:

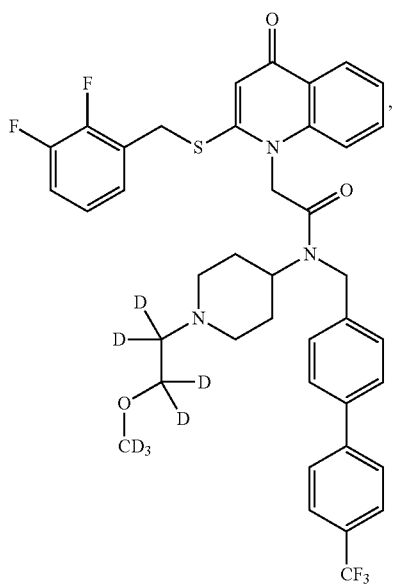

229
-continued
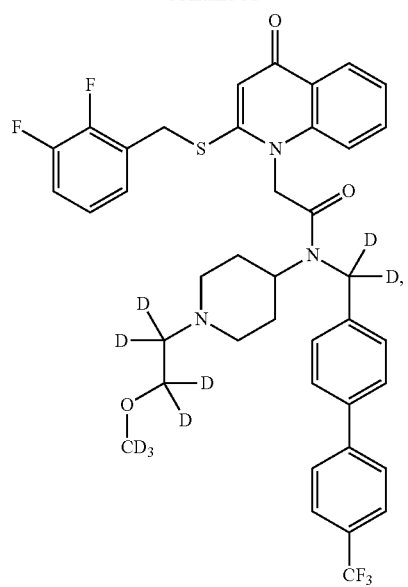
230
-continued
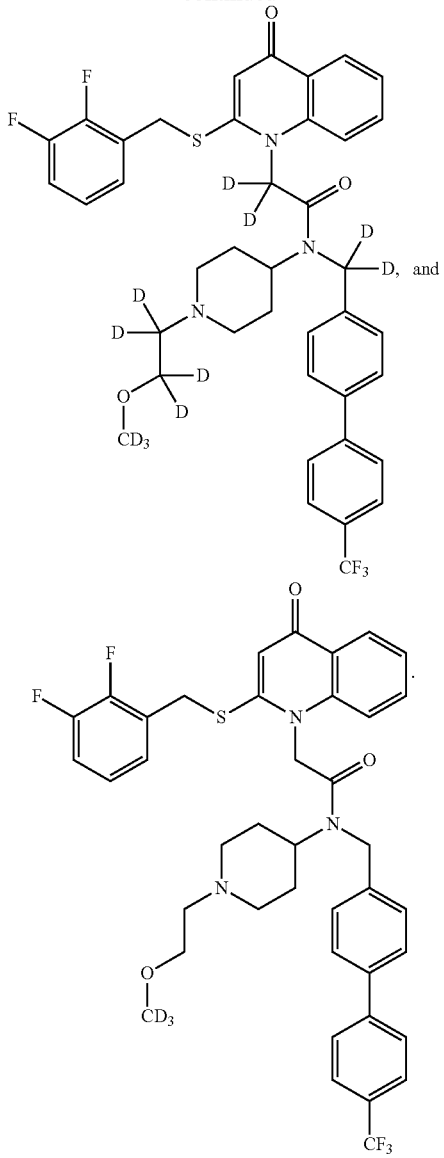
* * * * *